(12) United States Patent
Sugimoto et al.

(10) Patent No.: US 7,901,794 B2
(45) Date of Patent: Mar. 8, 2011

(54) MATERIAL FOR LIGHT-EMITTING ELEMENT AND LIGHT EMITTING ELEMENT

(75) Inventors: Kazunori Sugimoto, Otsu (JP); Seiichiro Murase, Otsu (JP); Daisuke Kitazawa, Otsu (JP); Kazumasa Nagao, Otsu (JP); Takafumi Ogawa, Otsu (JP); Tsuyoshi Tominaga, Otsu (JP)

(73) Assignee: Toray Industries, Inc., Tokyo (JP)

( * ) Notice: Subject to any disclaimer, the term of this patent is extended or adjusted under 35 U.S.C. 154(b) by 451 days.

(21) Appl. No.: 11/817,143

(22) PCT Filed: Feb. 23, 2006

(86) PCT No.: PCT/JP2006/303254
§ 371 (c)(1),
(2), (4) Date: Aug. 24, 2007

(87) PCT Pub. No.: WO2006/090772
PCT Pub. Date: Aug. 31, 2006

(65) Prior Publication Data
US 2009/0066245 A1    Mar. 12, 2009

(30) Foreign Application Priority Data
Feb. 25, 2005 (JP) .................. 2005-050282

(51) Int. Cl.
*H01J 40/16* (2006.01)
(52) U.S. Cl. .................. 428/690; 313/540; 548/235
(58) Field of Classification Search ................ None
See application file for complete search history.

(56) References Cited

U.S. PATENT DOCUMENTS
2004/0023480 A1    2/2004   Dennison
2004/0234809 A1   11/2004   Chen et al.

FOREIGN PATENT DOCUMENTS
| GB | 1143505 | * | 2/1969 |
| GB | 1143505 | A | 2/1969 |
| JP | 10-340786 | | 12/1998 |
| JP | 10 340786 | A | 12/1998 |
| JP | 2003-109761 | * | 4/2003 |
| JP | 2003 109761 | A | 4/2003 |
| JP | 2004-263178 | | 9/2004 |
| JP | 2004-349245 | * | 12/2004 |
| WO | 2004-072053 | | 8/2004 |
| WO | 2004/072053 | A1 | 8/2004 |

OTHER PUBLICATIONS

Supplementary European Search Report in related application EP 06 71 4394 mailed Jan. 21, 2010.

* cited by examiner

*Primary Examiner* — D. Lawrence Tarazano
*Assistant Examiner* — Gregory Clark
(74) *Attorney, Agent, or Firm* — Pillsbury Winthrop Shaw Pittman LLP

(57) ABSTRACT

The present invention is a light-emitting device material characterized by containing a pyrene compound represented by the following general formula (1):

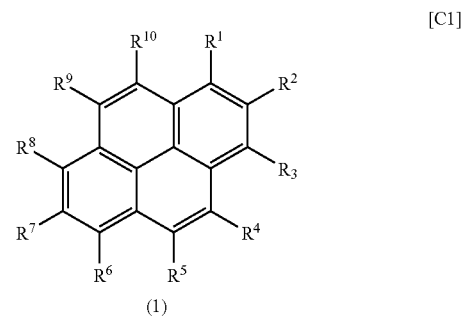

wherein R1 to R10 are specific functional groups, provided that at least one of the R1 to R10 is a substituent represented by the following general formula (2):

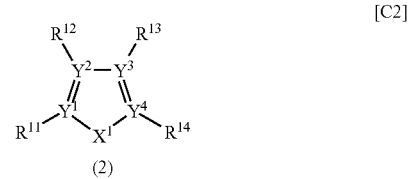

wherein R11 to R14 are specific functional groups, provided that any one of the R11 to R14 is used for a single bond with a pyrene skeleton; X1 is a group represented by the following general formula (3):

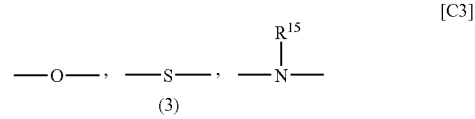

wherein R15 is a specific functional group; and
Y1 to Y4 is selected from among a nitrogen atom and a carbon atom, provided that at least one of the Y1 to Y4 is a nitrogen atom and at least one thereof is a carbon atom, and no substituents exist on the nitrogen atom in the case of the nitrogen atom.

This material provides a light-emitting device having high luminous efficiency and excellent durability.

12 Claims, No Drawings

MATERIAL FOR LIGHT-EMITTING ELEMENT AND LIGHT EMITTING ELEMENT

CROSS-REFERENCE TO PRIOR APPLICATION

This is a U.S. National Phase Application under 35 U.S.C. §371 of International Patent Application No. PCT/JP2006/303254 filed Feb. 23, 2006, which claims the benefit of Japanese Application No. 2005-050282, filed Feb. 25, 2005 all of which are incorporated by reference herein. The International Application was published in Japanese on Aug. 13, 2006 as WO 2006/090772 A1 under PCT Article 21(2).

TECHNICAL FIELD

The present invention relates to a pyrene compound useful as a fluorescent dye and a charge transporting material, and to a light-emitting device using this material, which is utilizable in the fields such as display device, flat-panel display, backlight, illumination, interior, mark, signboard, electrophotographic apparatus and light signal generator.

BACKGROUND ART

In recent years, the studies of an organic thin-film LED (LED: light emitting device) have actively been conducted such that an electron injected from a cathode and a hole injected from an anode recombine in an organic compound held between both of the cathode and the anode. This LED is characterized by thin type, high brightness under low drive voltages and multicolor light emission through selection of light-emitting materials, thereby attracting notice.

These studies have been conducted by many research institutions since it was revealed by C. W. Tang et al. of Kodak Company that an organic thin-film LED emitted light with high brightness. The typical structure of an organic thin-film LED presented by a study group of the Kodak Company is such that a diamine compound for hole transporting, tris(8-quinolinolate)aluminum (III) as a luminescent layer and Mg:Ag as a cathode are sequentially layered on an ITO glass substrate, which LED allows green light emission of 1000 cd/m2 at a driving voltage of approximately 10 V (refer to Nonpatent Literature 1).

The use of various fluorescent materials for a luminescent layer allows an organic thin-film LED to obtain diverse luminescent colors, so that the studies of practical application to displays are actively carried out. Among light-emitting materials of the three primary colors, the studies of green light-emitting materials are the most advanced, and the earnest studies in red light-emitting materials and blue light-emitting materials are presently made toward performance improvement.

One of the largest problems in an organic thin-film LED is to improve durability of the device. In particular, with regard to blue, few blue light-emitting materials provide a device having excellent durability and high reliability. For example, a technique is disclosed in which a styrylamine derivative (refer to Patent Literature 1) and a perylene derivative (refer to Patent Literature 2) are used as a blue dopant material. Also, a technique is disclosed in which a pyrene compound is used for a blue light-emitting device. Blue light-emitting devices using various pyrene compounds (refer to Patent Literatures 3 to 5) are reported; however, any of them has insufficient durability.

(Nonpatent Literature 1)
Applied Physics Letters (USA) 1987, Vol. 51, No. 12, pages 913 to 915

(Patent Literature 1)
Japanese Unexamined Patent Publication No. 5-17765 (claim 1)
(Patent Literature 2)
Japanese Unexamined Patent Publication No. 2003-86380 (claim 3)
(Patent Literature 3)
Japanese Unexamined Patent Publication No. 2001-118682 (claim 1)
(Patent Literature 4)
Japanese Unexamined Patent Publication No. 2004-75567 (claims 1 to 4)
(Patent Literature 5)
International Publication No. 2004/096945 Pamphlet (Claims)

DISCLOSURE OF THE INVENTION

Problems to be Solved by the Invention

As described above, a blue light-emitting device having high luminous efficiency and excellent durability has not been provided in conventional organic thin-film LEDs. Then, the present invention is intended to solve problems in the prior art and to provide a light-emitting device material allowing a blue light-emitting device having high luminous efficiency and excellent durability, and a light-emitting device using this material.

Means for Solving the Problem

The present invention provides a light-emitting device material containing a pyrene compound represented by the general formula (1):

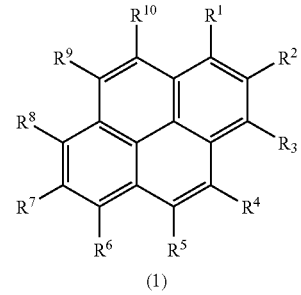

wherein R1 to R10 each may be the same or different and are selected from among hydrogen, alkyl group, cycloalkyl group, heterocyclic group, alkenyl group, cycloalkenyl group, alkynyl group, alkoxy group, alkylthio group, arylether group, arylthioether group, aryl group, heteroaryl group, halogen, cyano group, carbonyl group, carboxyl group, oxycarbonyl group, carbamoyl group, amino group and phosphine oxide group, and the R1 to R10 may form a ring with adjacent substituents, provided that at least one of the R1 to R10 is a substituent represented by the following general formula (2):

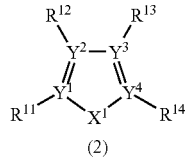

wherein R11 to R14 each may be the same or different and are selected from among hydrogen, alkyl group, cycloalkyl group, heterocyclic group, alkenyl group, cycloalkenyl group, alkynyl group, alkoxy group, alkylthio group, arylether group, arylthioether group, aryl group, heteroaryl group, halogen, cyano group, carbonyl group, carboxyl group, oxycarbonyl group, carbamoyl group, amino group and phosphine oxide group, and a ring with a carbon number of 4 to 6 may be formed between R11 and R12, R12 and R13, or R13 and R14, provided that any one of the R11 to R14 is used for a single bond with a pyrene skeleton of the general formula (1); X1 is a group represented by the following general formula (3):

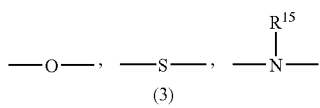

(3)  [C3]

wherein R15 is selected from among hydrogen, alkyl group, cycloalkyl group, heterocyclic group, alkenyl group, cycloalkenyl group, alkynyl group, aryl group, heteroaryl group, cyano group, carbonyl group, carboxyl group, oxycarbonyl group and carbamoyl group; and Y1 to Y4 is selected from among a nitrogen atom and a carbon atom, provided that at least one of the Y1 to Y4 is a nitrogen atom and at least one thereof is a carbon atom, and no substituents exist on the nitrogen atom in the case of the nitrogen atom.

The present invention is a light-emitting device characterized in that at least a luminescent layer exists between an anode and a cathode to emit light by electric energy, and by containing a light-emitting device material represented by the general formula (1).

EFFECT OF THE INVENTION

The present invention can provide a light-emitting device material utilizable for a light-emitting device and high in luminous efficiency. In addition, according to the present invention, the use of the above-mentioned light-emitting device material allows a light-emitting device excellent in durability.

BEST MODE FOR CARRYING OUT OF THE INVENTION

A pyrene compound represented by the general formula (1) in the present invention is described in detail.

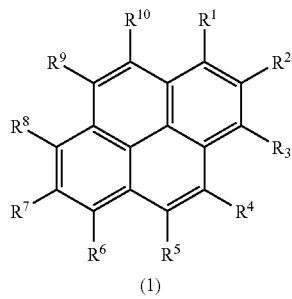

(1)  [C4]

R1 to R10 each may be the same or different and are selected from among hydrogen, alkyl group, cycloalkyl group, heterocyclic group, alkenyl group, cycloalkenyl group, alkynyl group, alkoxy group, alkylthio group, arylether group, arylthioether group, aryl group, heteroaryl group, halogen, cyano group, carbonyl group, carboxyl group, oxycarbonyl group, carbamoyl group, amino group and phosphine oxide group. The R1 to R10 may form a ring with adjacent substituents, provided that at least one of the R1 to R10 is a substituent represented by the following general formula (2).

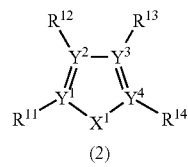

(2)  [C5]

R11 to R14 each may be the same or different and are selected from among hydrogen, alkyl group, cycloalkyl group, heterocyclic group, alkenyl group, cycloalkenyl group, alkynyl group, alkoxy group, alkylthio group, arylether group, arylthioether group, aryl group, heteroaryl group, halogen, cyano group, carbonyl group, carboxyl group, oxycarbonyl group, carbamoyl group, amino group and phosphine oxide group. A ring with a carbon number of 4 to 6 may be formed between R11 and R12, R12 and R13, or R13 and R14, provided that any one of the R11 to R14 is used for a single bond with a pyrene skeleton. X1 is a group represented by the following general formula (3) and Y1 to Y4 is selected from among a nitrogen atom and a carbon atom, provided that at least one of the Y1 to Y4 is a nitrogen atom and at least one thereof is a carbon atom, and no substituents exist on the nitrogen atom in the case of the nitrogen atom.

$$—O—, \quad —S—, \quad —\underset{\underset{R^{15}}{|}}{N}—$$

(3)  [C6]

R15 is selected from among hydrogen, alkyl group, cycloalkyl group, heterocyclic group, alkenyl group, cycloalkenyl group, alkynyl group, aryl group, heteroaryl group, cyano group, carbonyl group, carboxyl group, oxycarbonyl group and carbamoyl group.

Among these substituents, an alkyl group denotes saturated aliphatic hydrocarbon groups such as a methyl group, ethyl group, n-propyl group, isopropyl group, n-butyl group, sec-butyl group and tert-butyl group, which alkyl group may have a substituent or not. An added substituent in the case of being substituted is not particularly limited, for example, including an alkyl group, aryl group and heteroaryl group; this point is common to the following description also. The carbon number of an alkyl group is not particularly limited, being in a range of typically 1 or more to 20 or less, preferably 1 or more to 8 or less in view of availability and costs.

A cycloalkyl group denotes saturated alicyclic hydrocarbon groups such as cyclopropyl, cyclohexyl, norbornyl and adamantyl, which cycloalkyl group may have a substituent or not. The carbon number of an alkyl group portion is not particularly limited, being in a range of typically 3 or more to 20 or less.

A heterocyclic group denotes alicyclic rings having an atom except carbon in a ring, such as a pyran ring, piperidine ring and cyclic amide, which heterocyclic group may have a substituent or not. The carbon number of a heterocyclic group is not particularly limited, being in a range of typically 2 or more to 20 or less.

An alkenyl group denotes unsaturated aliphatic hydrocarbon groups containing a double bond, such as a vinyl group, allyl group and butadienyl group, which alkenyl group may have a substituent or not. The carbon number of an alkenyl group is not particularly limited, being in a range of typically 2 to 20 both inclusive.

A cycloalkenyl group denotes unsaturated alicyclic hydrocarbon groups containing a double bond, such as a cyclopentenyl group, cyclopentadienyl group and cyclohexenyl group, which cycloalkenyl group may have a substituent or not.

An alkynyl group denotes an unsaturated aliphatic hydrocarbon group containing a triple bond, such as an ethinyl group, which alkynyl group may have a substituent or not. The carbon number of an alkynyl group is not particularly limited, being in a range of typically 2 to 20 both inclusive.

An alkoxy group denotes functional groups in which aliphatic hydrocarbon groups are bonded through an ether bond, such as a methoxy group, ethoxy group and propoxy group, which aliphatic hydrocarbon groups may have a substituent or not. The carbon number of an alkoxy group is not particularly limited, being in a range of typically 1 or more to 20 or less.

An alkylthio group is such that an oxygen atom of an ether bond of an alkoxy group is substituted with a sulfur atom. A hydrocarbon group of an alkylthio group may have a substituent or not. The carbon number of an alkylthio group is not particularly limited, being in a range of typically 1 or more less 20 or less.

An arylether group denotes a functional group in which aromatic hydrocarbon groups are bonded through an ether bond, such as a phenoxy group, which aromatic hydrocarbon groups may have a substituent or not. The carbon number of an arylether group is not particularly limited, being in a range of typically 6 or more to 40 or less.

An arylthioether group is such that an oxygen atom of an ether bond of an arylether group is substituted with a sulfur atom. Aromatic hydrocarbon groups in an arylthioether group may have a substituent or not. The carbon number of an arylthioether group is not particularly limited, being in a range of typically 6 to 40 both inclusive.

An aryl group denotes aromatic hydrocarbon groups such as a phenyl group, naphtyl group, biphenyl group, phenanthryl group, terphenyl group and pyrenyl group. An aryl group may have a substituent or not. The carbon number of an aryl group is not particularly limited, being in a range of typically 6 to 40 both inclusive.

A heteroaryl group denotes aromatic groups having an atom except carbon in a ring, such as a furanyl group, thiophenyl group, oxazolyl group, pyridyl group, quinolinyl group and carbazolyl group, which heteroaryl group may have a substituent or not. The carbon number of a heteroaryl group is not particularly limited, being in a range of typically 2 to 30 both inclusive.

A halogen atom denotes fluorine, chlorine, bromine and iodine.

A carbonyl group, carboxyl group, oxycarbonyl group, carbamoyl group, amino group and phosphine oxide group may have a substituent or not, for example, which includes an alkyl group, cycloalkyl group, aryl group and heteroaryl group, and these substituents may further be substituted.

A ring formed between adjacent groups is such that any two adjacent substituents (for example, R1 and R2) selected from among R1 to R10 bond to each other to form a conjugated or unconjugated condensed ring, according to the above-mentioned general formula (1). These condensed rings may contain nitrogen, oxygen and sulfur atoms in an endocyclic structure, or be further condensed with another ring; but yet it is preferable that excellent heat resistance is obtained when atoms composing these condensed rings are only carbon atoms and hydrogen atoms, and therefore is preferable.

A pyrene compound represented by the general formula (1) of the present invention has high luminous efficiency and excellent heat resistance by reason of having a pyrene skeleton and an azole skeleton as an electron-accepting heterocyclic ring in a molecule. Here, a single bond in substitution for the R1 to R14 between carbon bonding to any one of R1 to R10 of the general formula (1) and Y1 to Y4 bonding to any one of R11 to R14 of the general formula (2) preferably substitutes for R1, R3, R6, R8 and R11 to R14 as the substituents between carbon bonding to any one of R1, R3, R6 and R8, and Y1 to Y4 bonding to anyone of R11 to R14, in view of availability of raw materials, ease of synthesis and capability of high-efficiency light emission.

A bond is formed between each of the substituents of R11 and R12, R12 and R13, or R13 and R14 in the general formula (2); then, a ring with a carbon number of 4 to 6 is preferably formed by reason of allowing high luminous efficiency and excellent heat resistance.

In addition, a pyrene compound represented by the general formula (4) is preferably formed in view of availability of raw materials and ease of synthesis, and allowing high-efficiency light emission and excellent heat resistance.

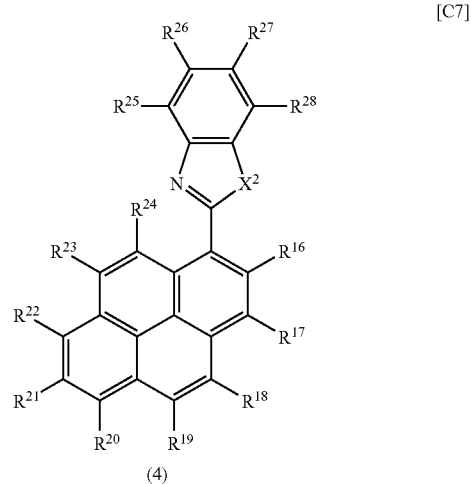

[C7]

(4)

R16 to R24 each may be the same or different and are selected from among hydrogen, alkyl group, cycloalkyl group, heterocyclic group, alkenyl group, cycloalkenyl group, alkynyl group, alkoxy group, alkylthio group, arylether group, arylthioether group, aryl group, heteroaryl group, halogen, cyano group, carbonyl group, carboxyl group, oxycarbonyl group, carbamoyl group, amino group, phosphine oxide group and condensed ring formed between adjacent groups. R25 to R28 each may be the same or different and are selected from among hydrogen, alkyl group, cycloalkyl group, heterocyclic group, alkenyl group, cycloalkenyl group, alkynyl group, alkoxy group, alkylthio group, arylether group, arylthioether group, aryl group, heteroaryl group, halogen, cyano group, carbonyl group, carboxyl group, oxycarbonyl group, carbamoyl group, amino group and phosphine oxide group. X2 is selected from among groups represented by the following general formula (5).

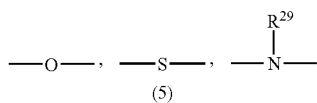

(5)

R29 is selected from among hydrogen, alkyl group, cycloalkyl group, heterocyclic group, alkenyl group, cycloalkenyl group, alkynyl group, aryl group, heteroaryl group, cyano group, carbonyl group, carboxyl group, oxycarbonyl group and carbamoyl group.

With regard to a pyrene compound represented by the general formula (1) of the present invention, at least one of R1 to R10 is preferably an aryl group or heteroaryl group by reason of restraining interaction between pyrene compounds to allow high-efficiency light emission. At least one of R1, R3, R6 and R8 is preferably an aryl group or heteroaryl group in view of ease of synthesis and the effect of restraining interaction between pyrene compounds. R1 and R6 are more preferably an aryl group or heteroaryl group by reason of improving the effect of restraining interaction between pyrene compounds.

A pyrene compound represented by the general formula (1) as described above is not particularly limited; specific examples thereof include the following.

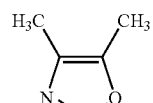

[1]

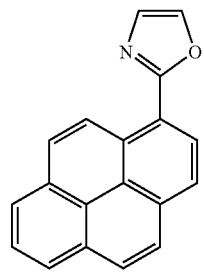

[2]

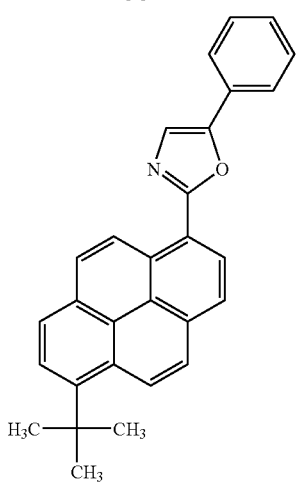

[3]

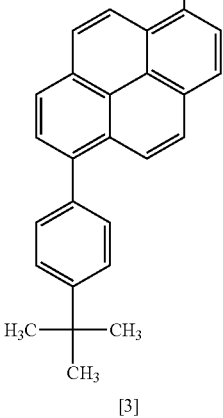

[4]

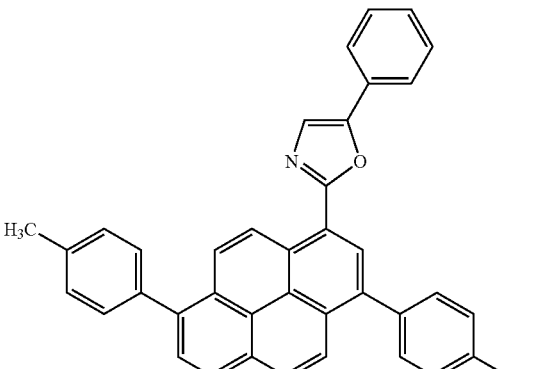

[5]

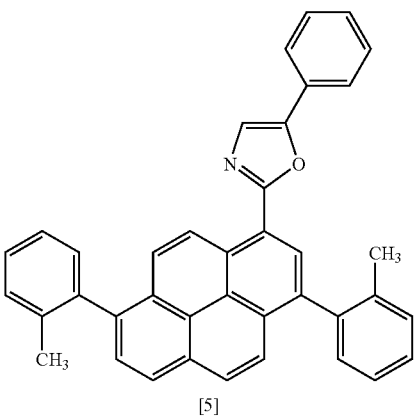

-continued
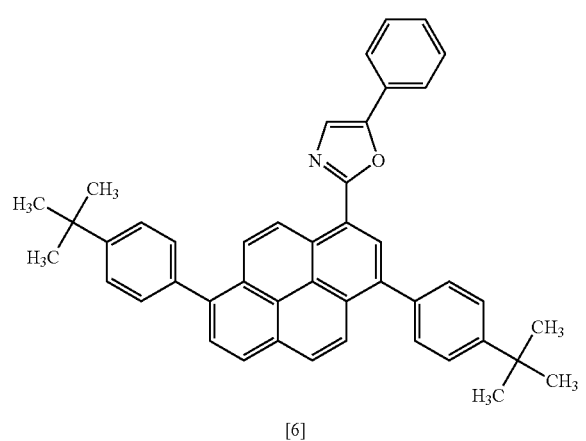
[6]
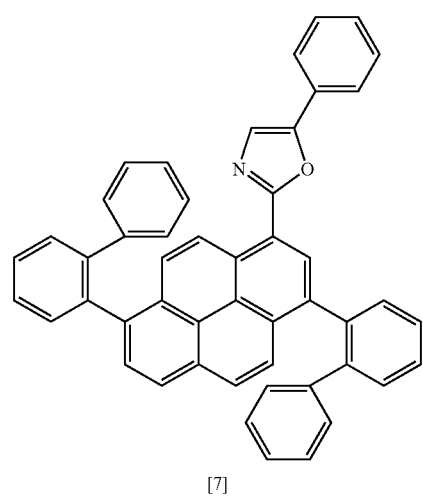
[7]
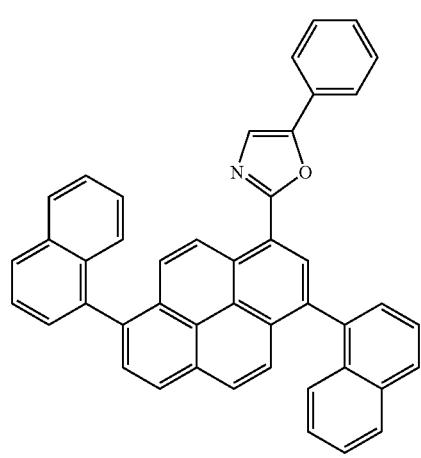
[8]
-continued
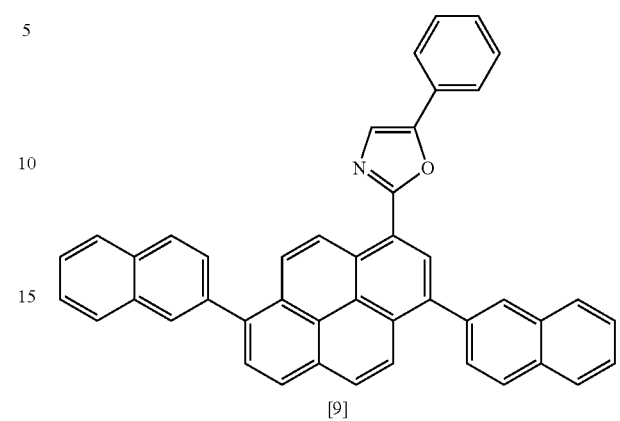
[9]
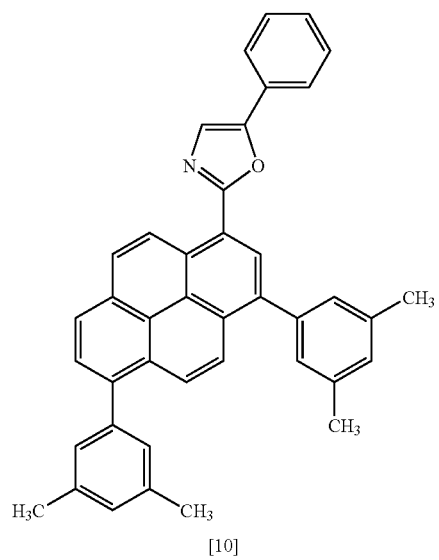
[10]
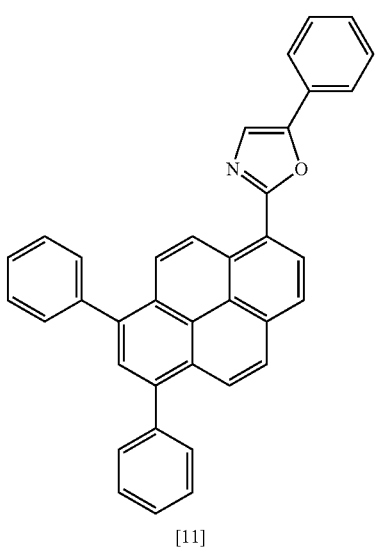
[11]

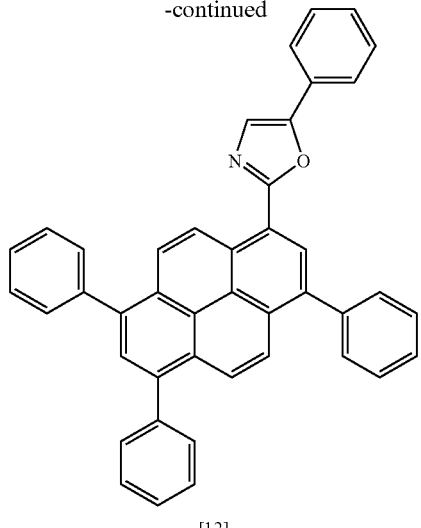
[12]
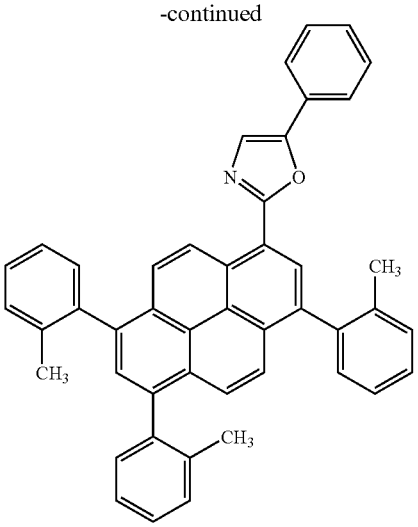
[15]
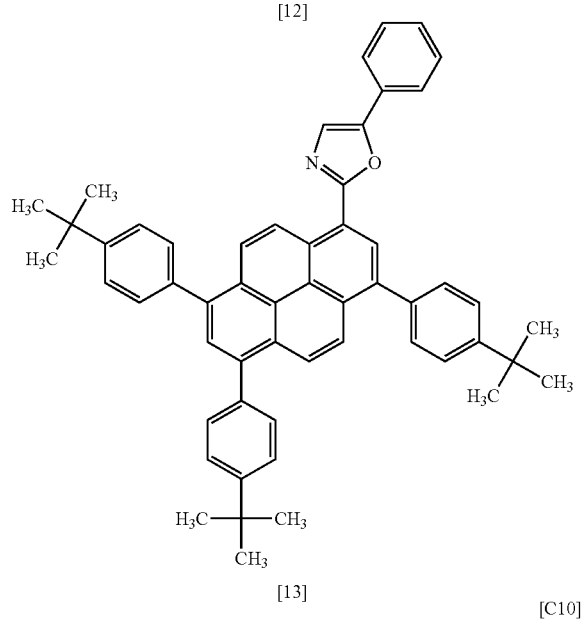
[13]
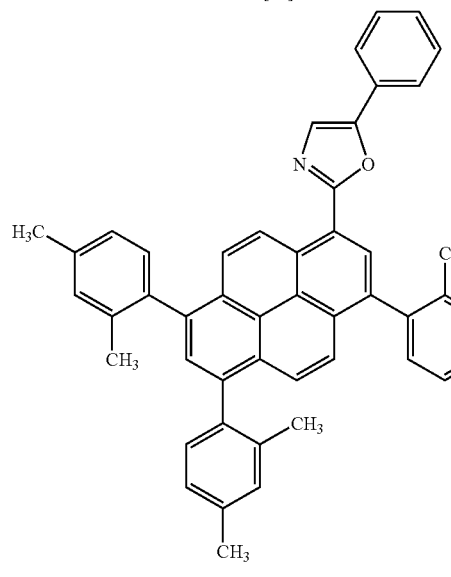
[16]
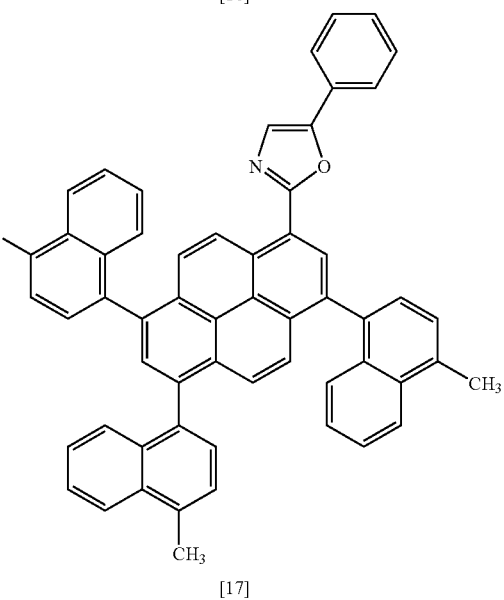
[14]
[17]

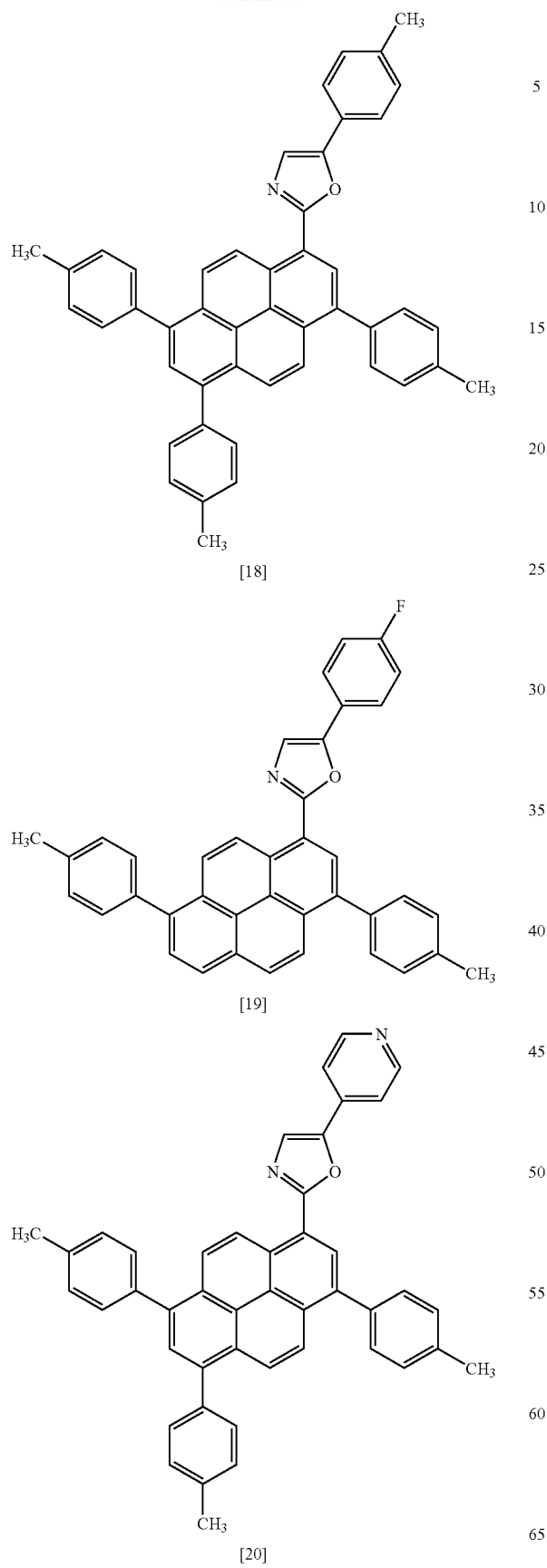
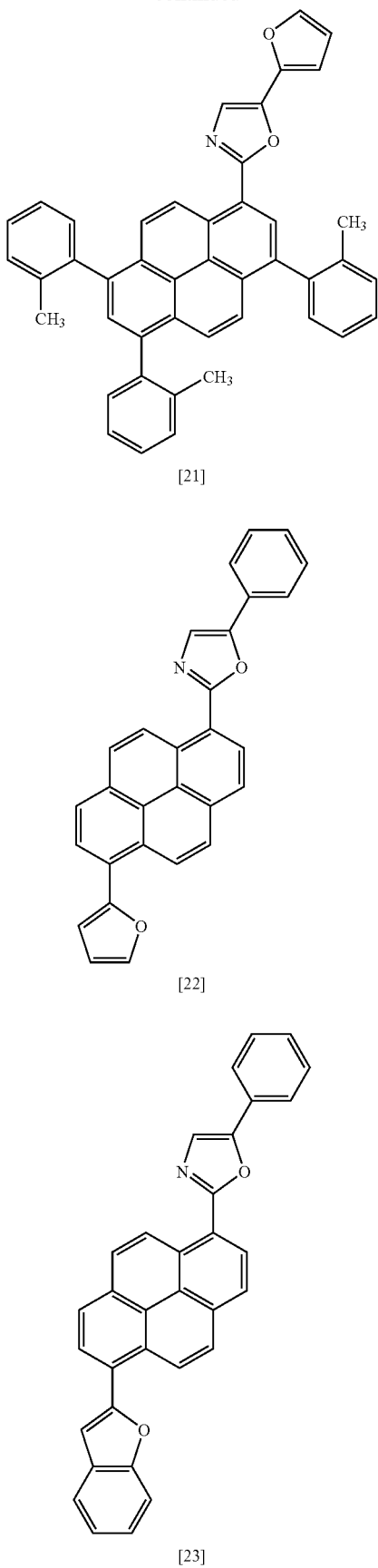

[C11]
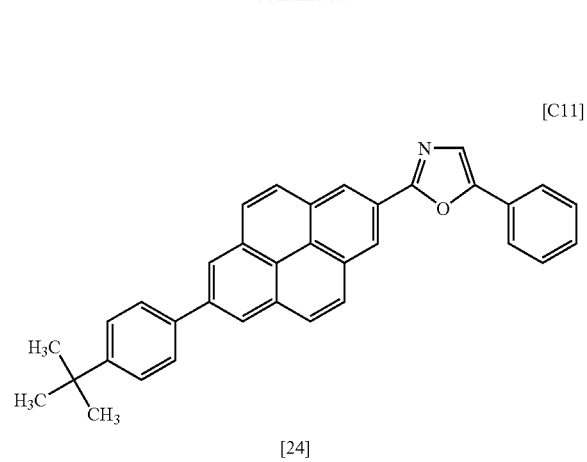
[24]
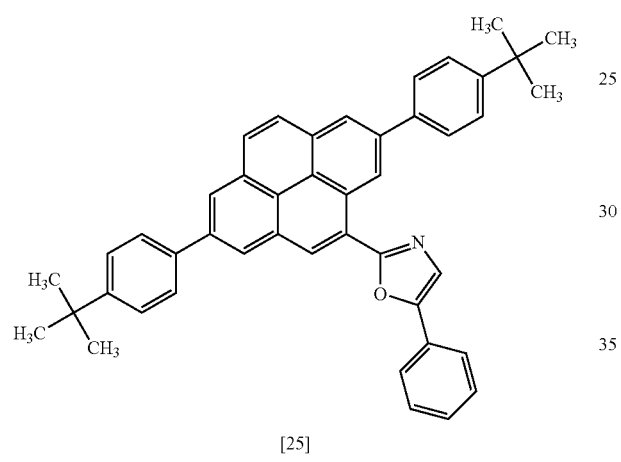
[25]
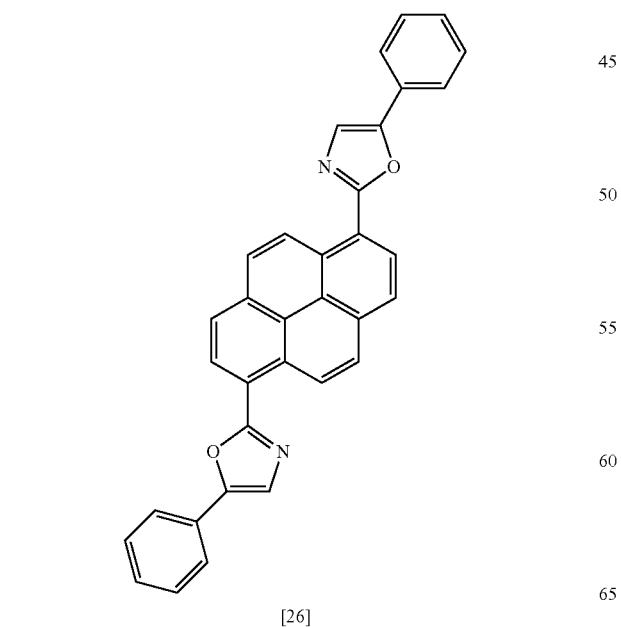
[26]
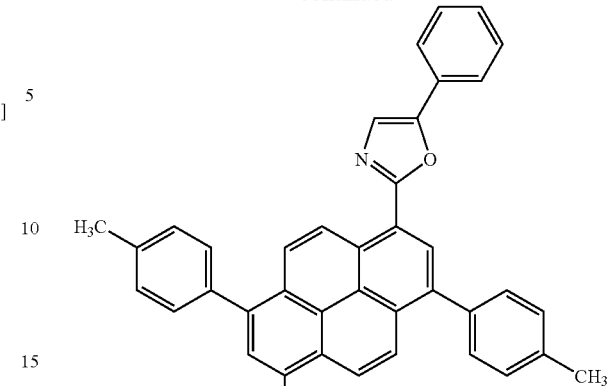
[27]
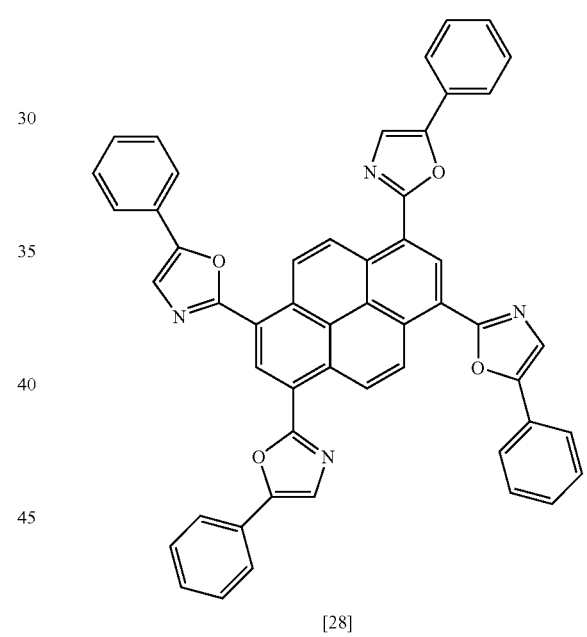
[28]
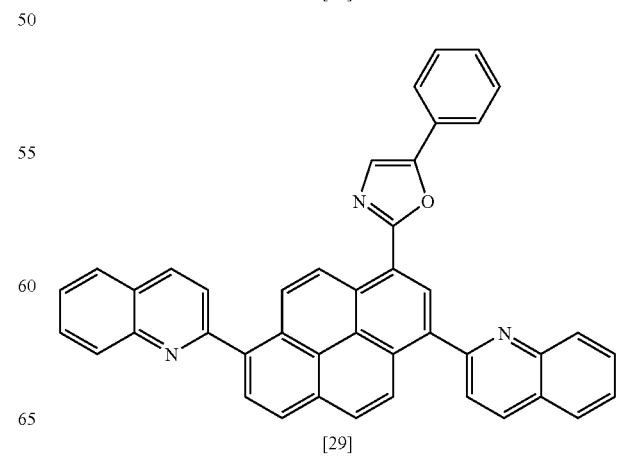
[29]

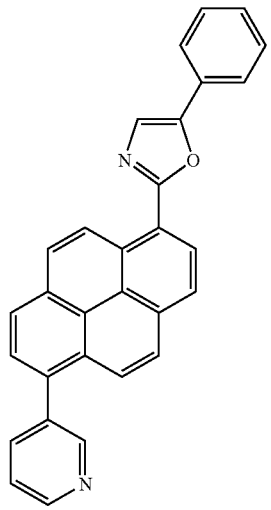
[30]
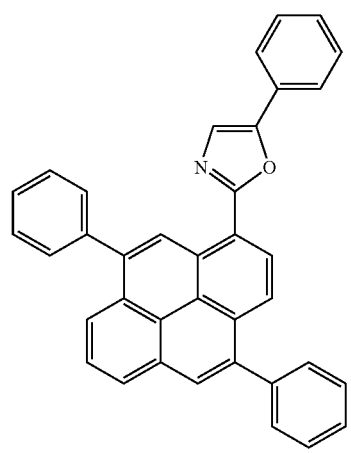
[31]
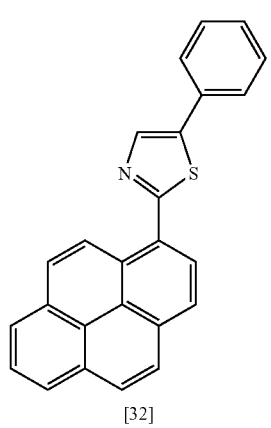
[32]
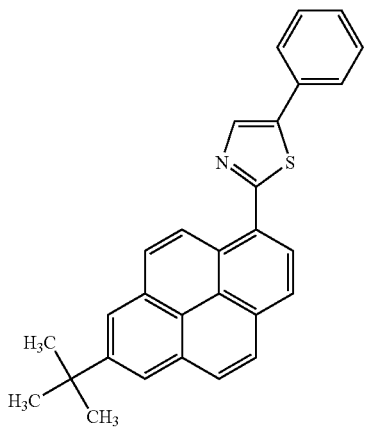
[33]
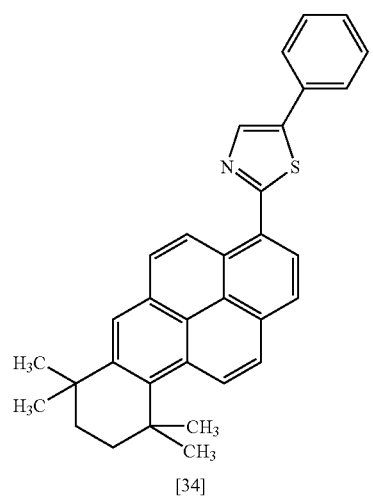
[34]
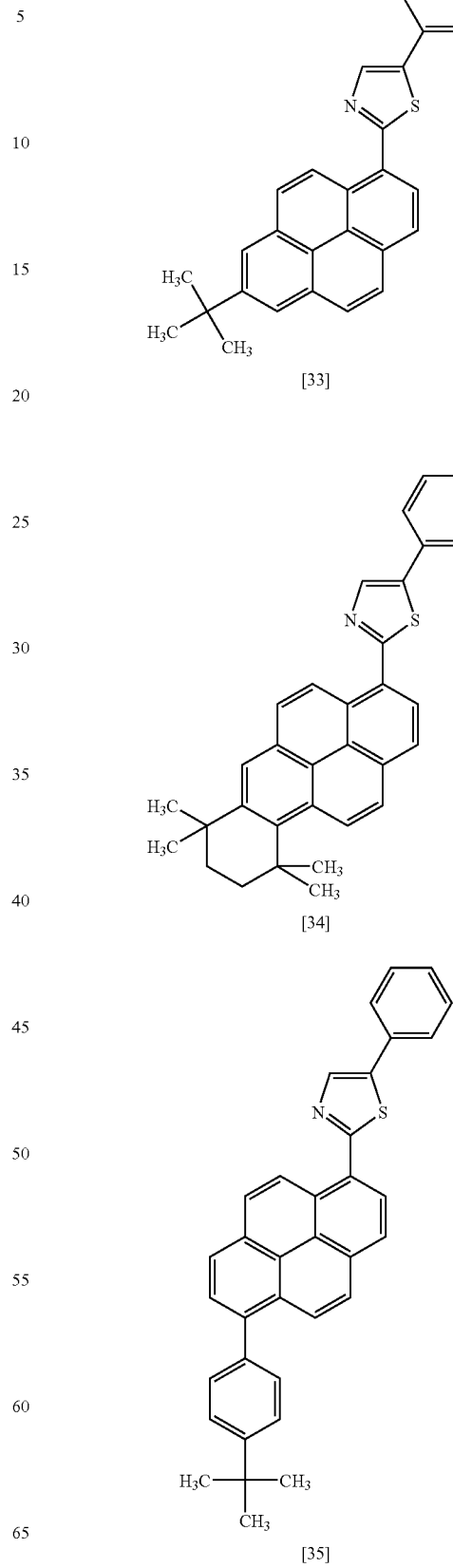
[35]

-continued
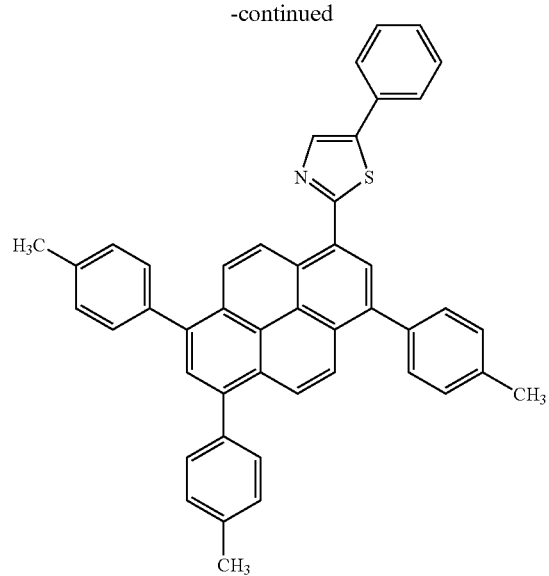
[36]
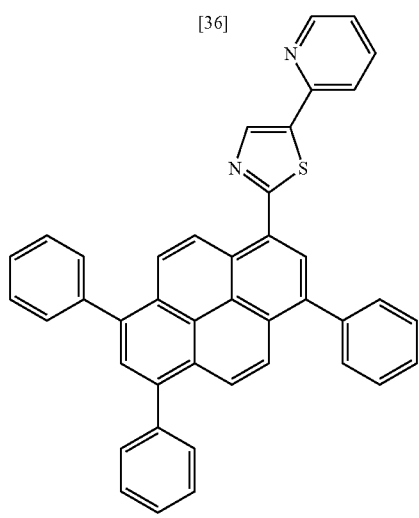
[37]
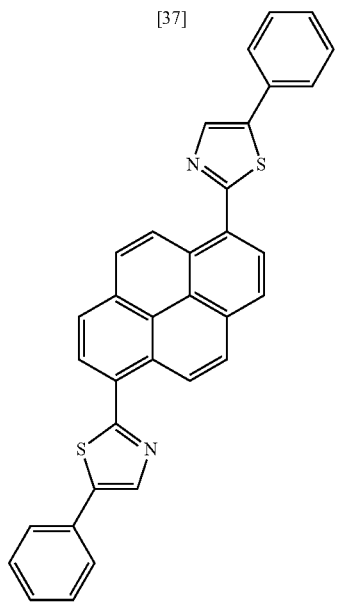
[38]
-continued
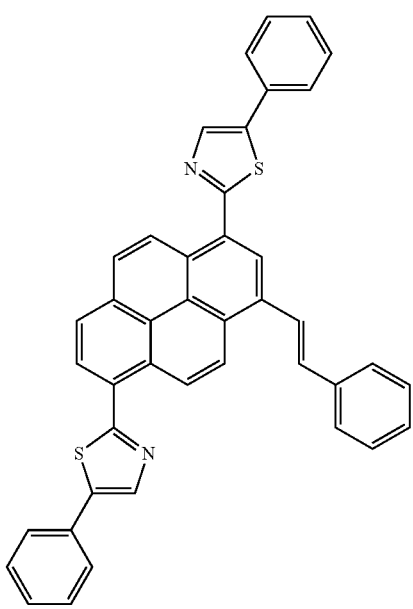
[39]
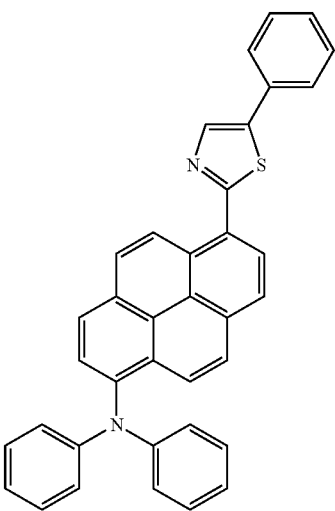
[40]
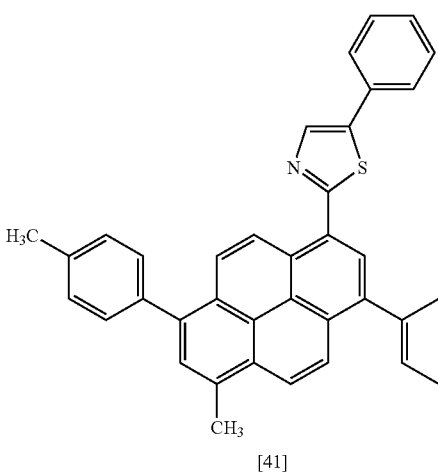
[41]

-continued
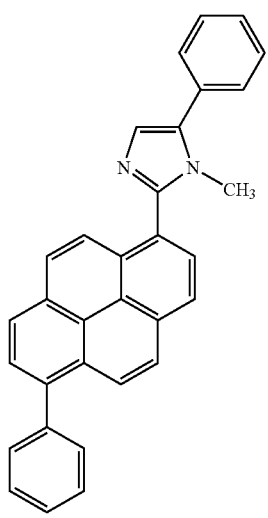
[42]
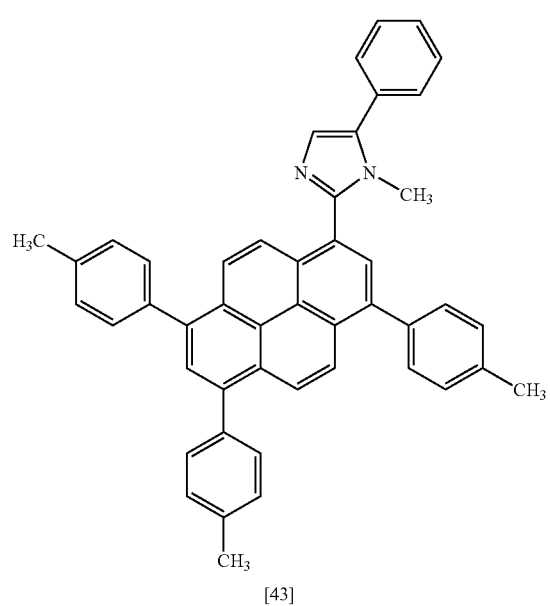
[43]
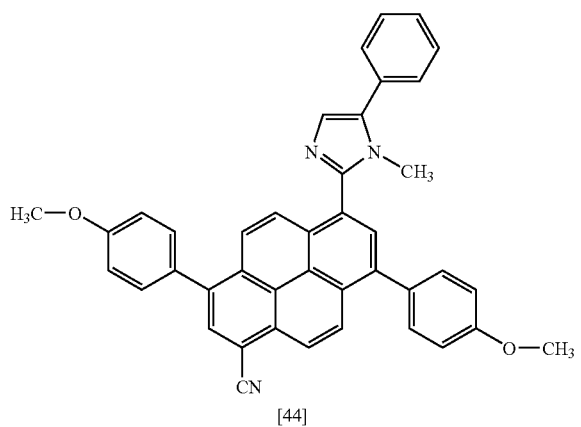
[44]
-continued
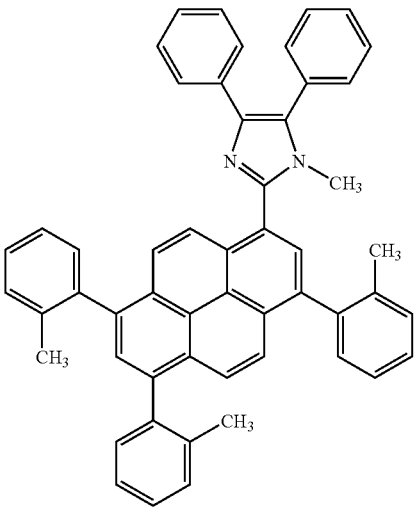
[45]
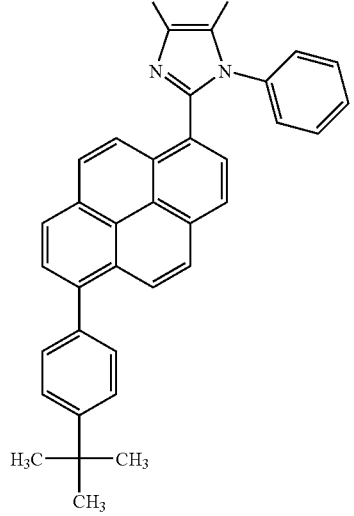
[46]
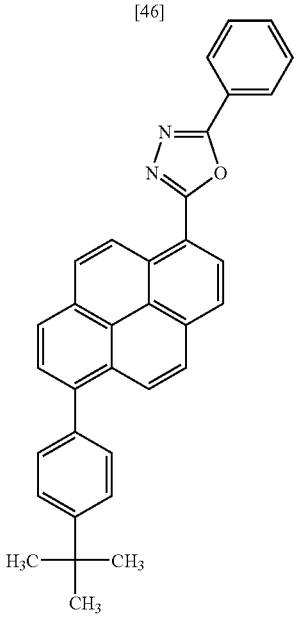
[47]

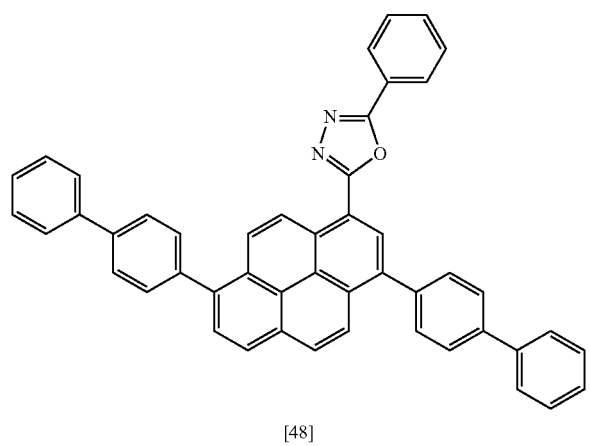
[48]
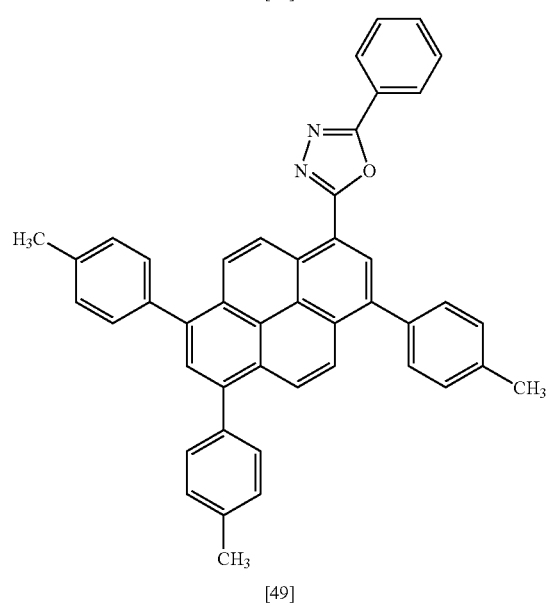
[49]
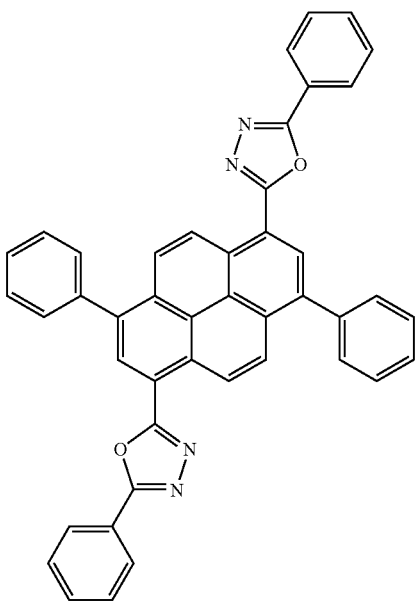
[50]
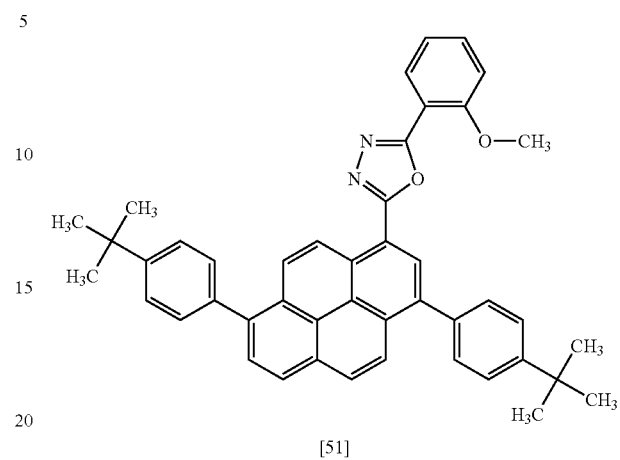
[51]
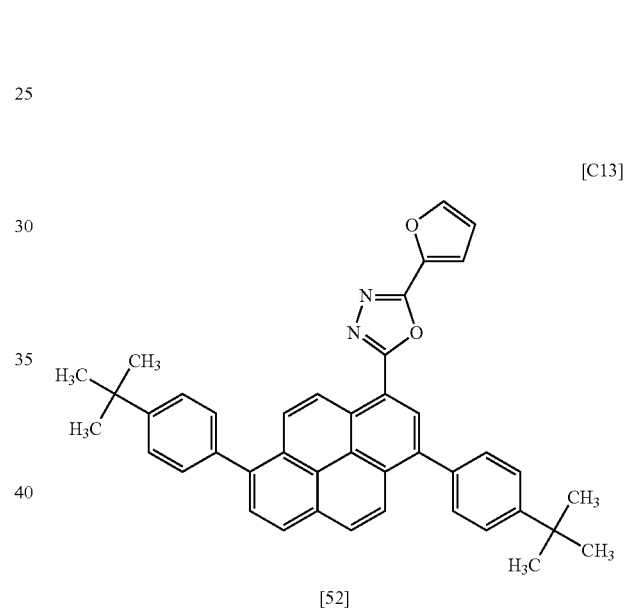
[52]
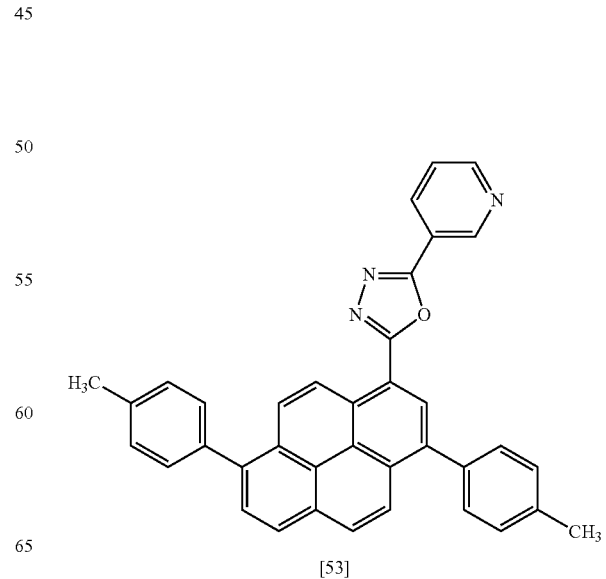
[53]

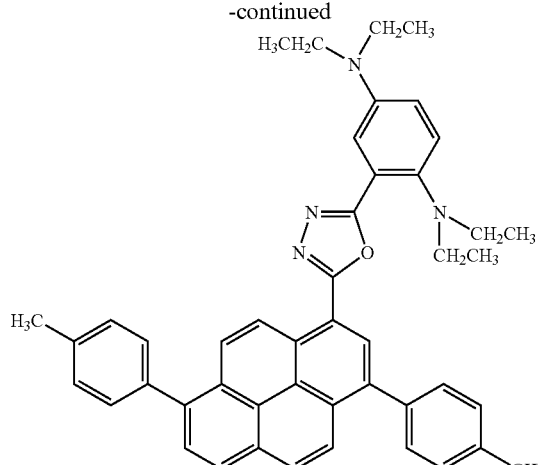
[54]
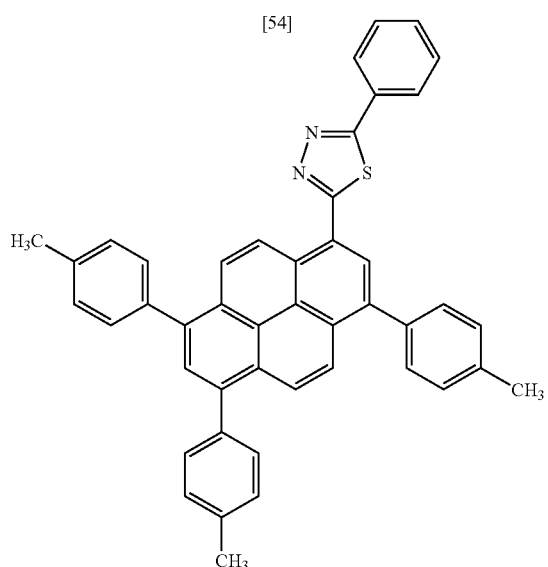
[55]
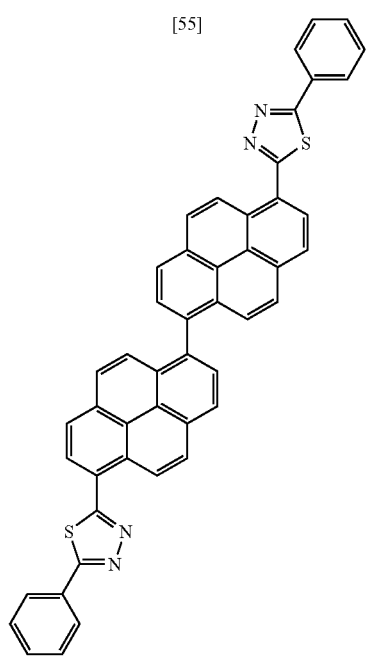
[56]
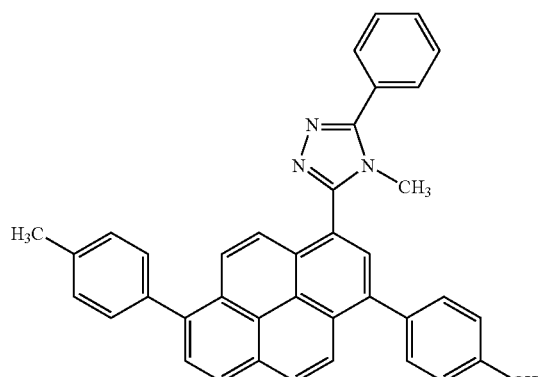
[57]
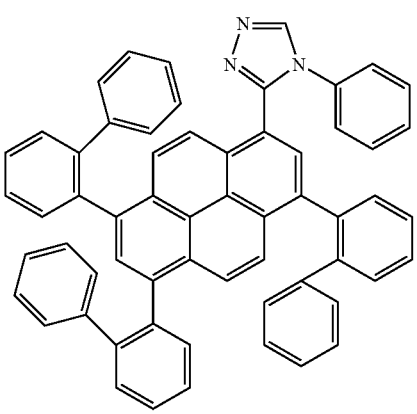
[58]
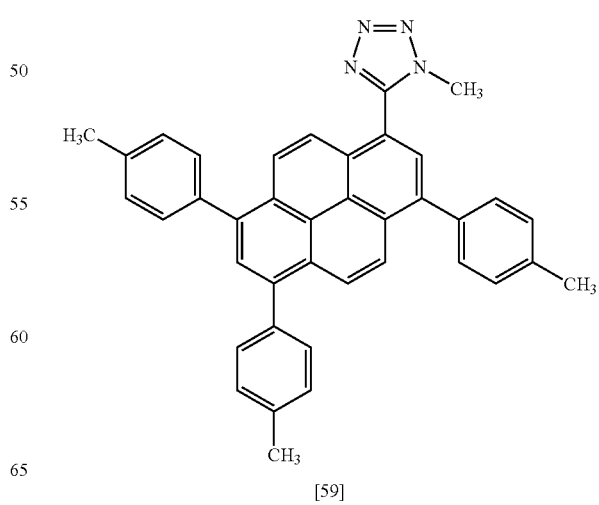
[59]

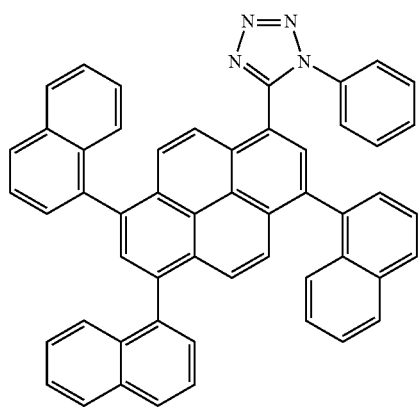
[60]
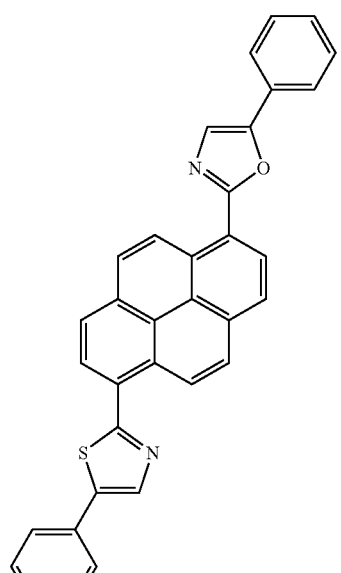
[61]
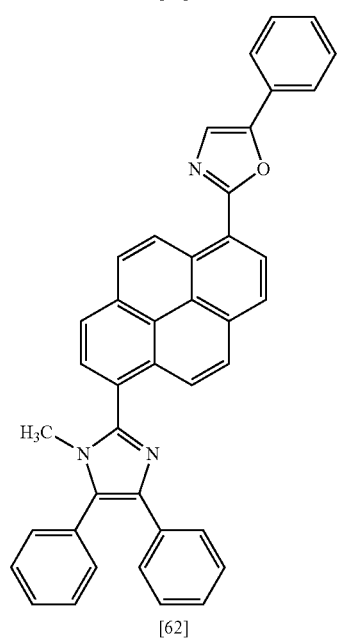
[62]
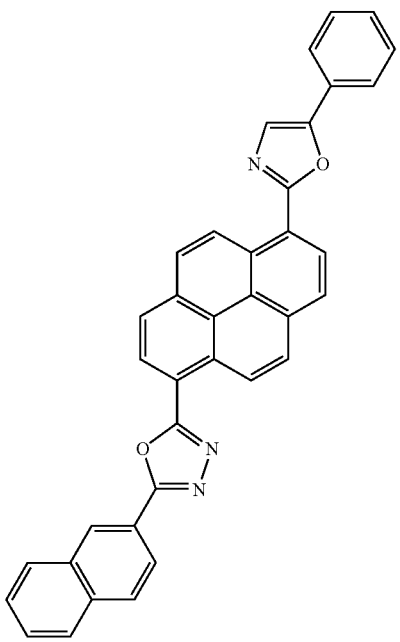
[63]
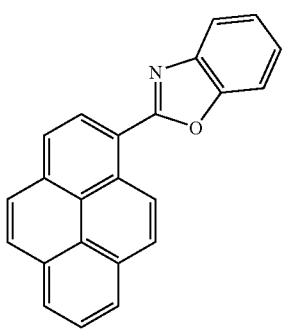
[64]
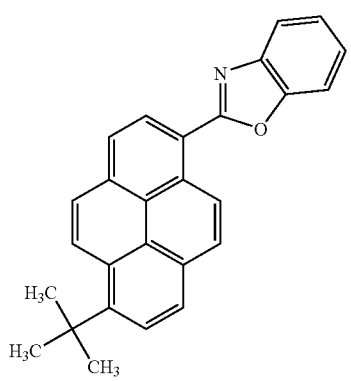
[65]

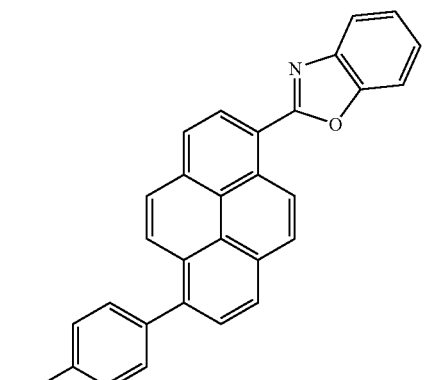
[66]
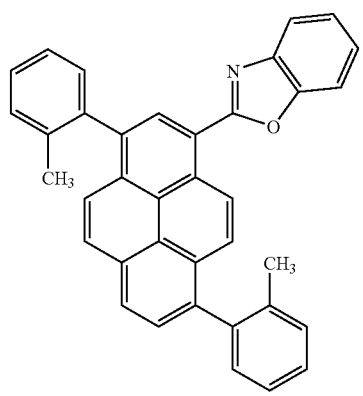
[69]
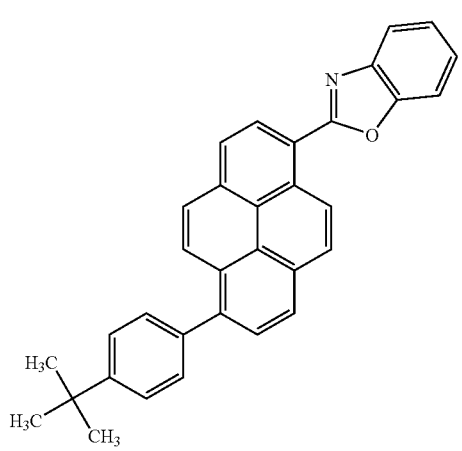
[67]
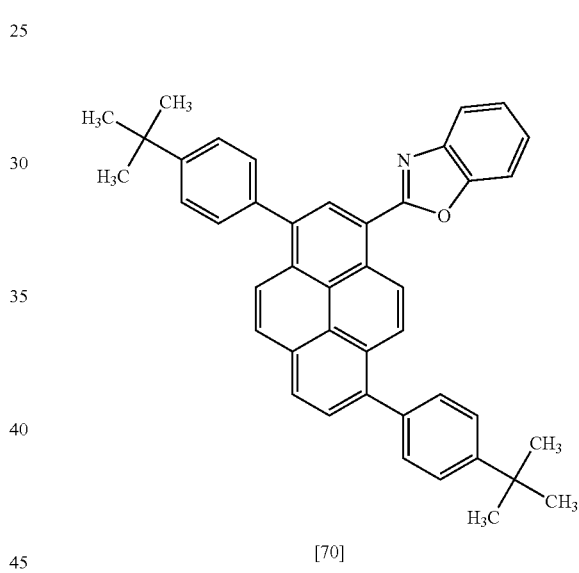
[70]
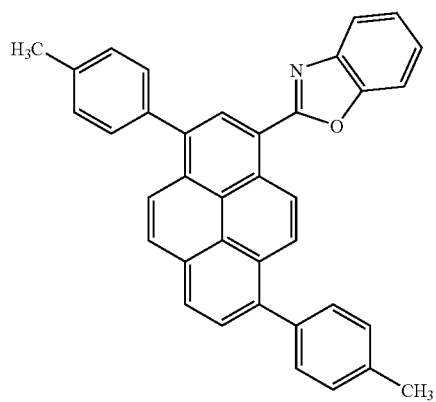
[68]
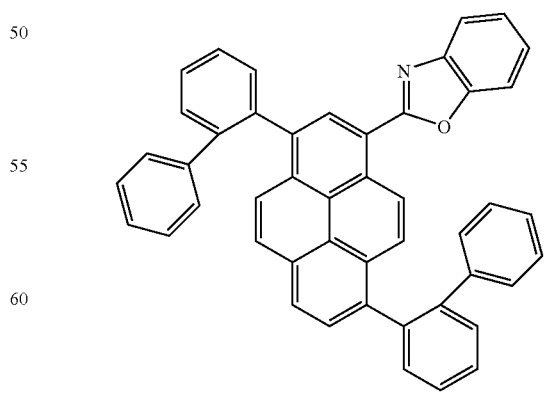
[71]

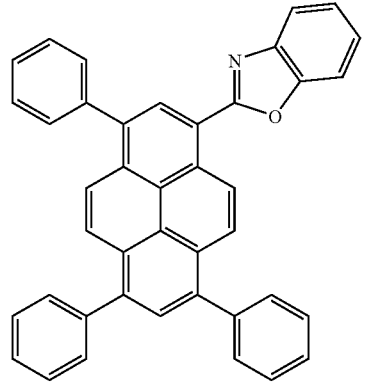
[72]
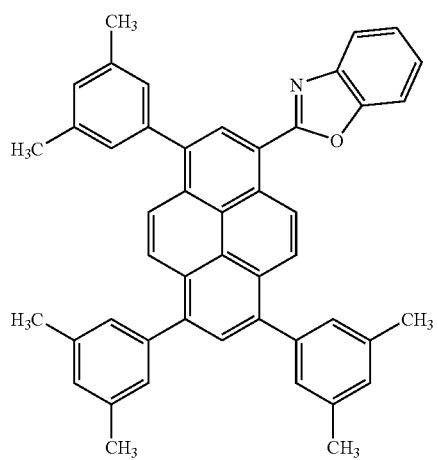
[73]
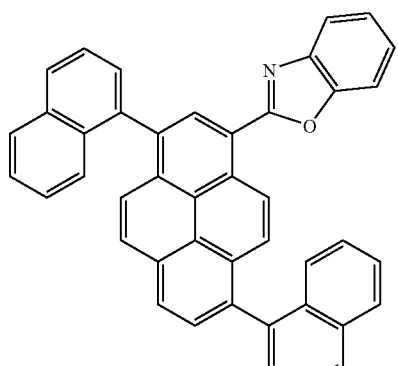
[74]
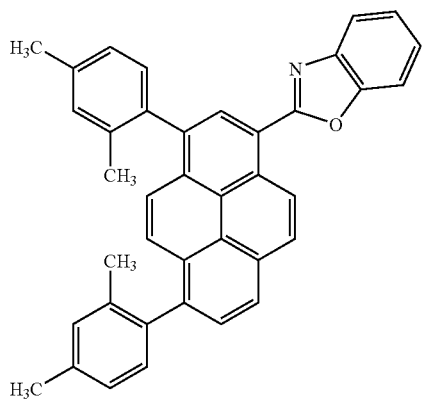
[75]
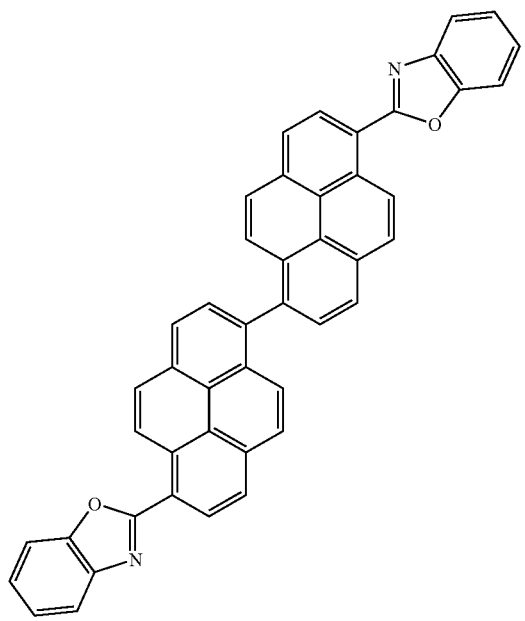
[76]
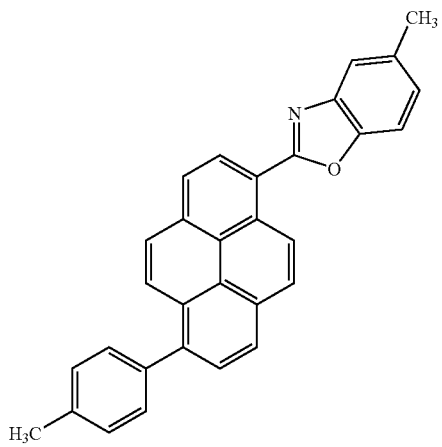
[77]

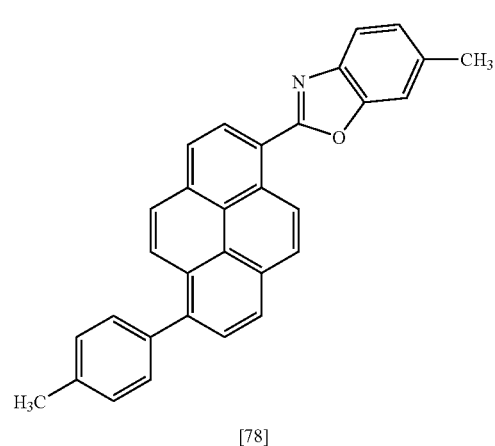
[78]
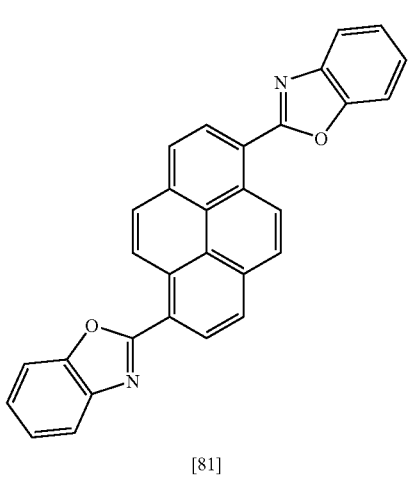
[81]
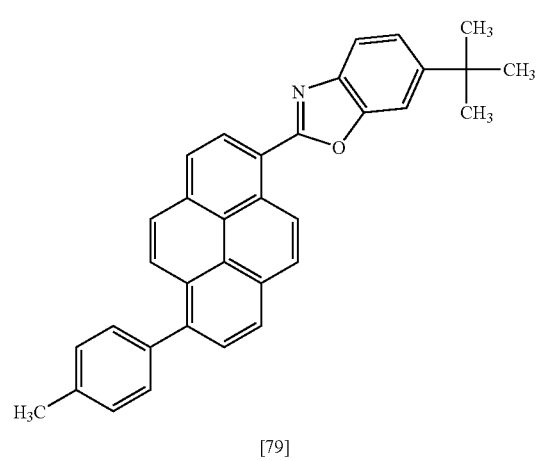
[79]
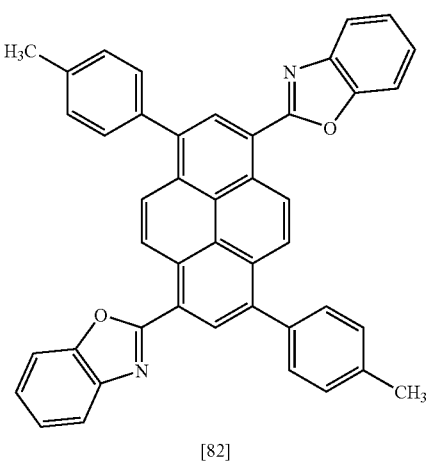
[82]
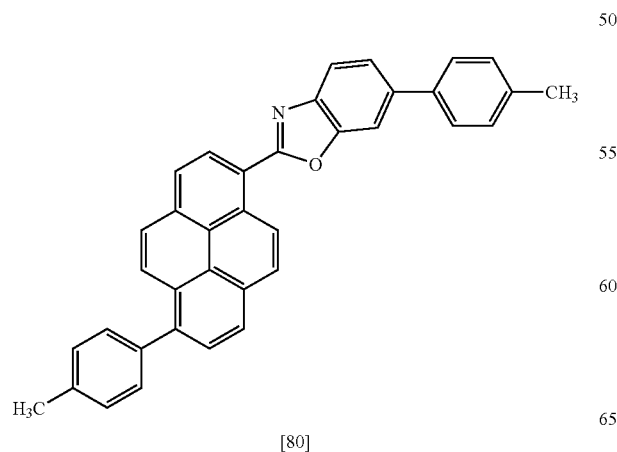
[80]
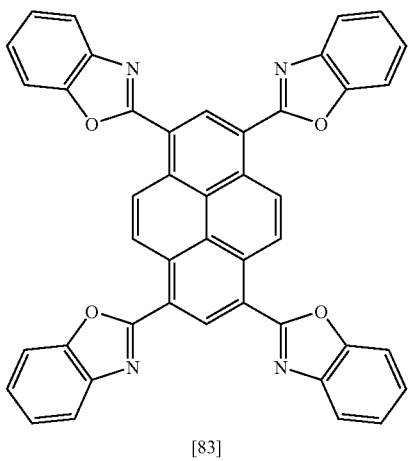
[83]

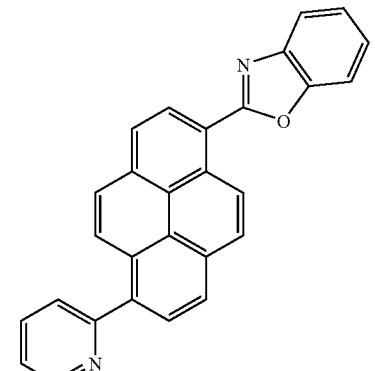
[84]
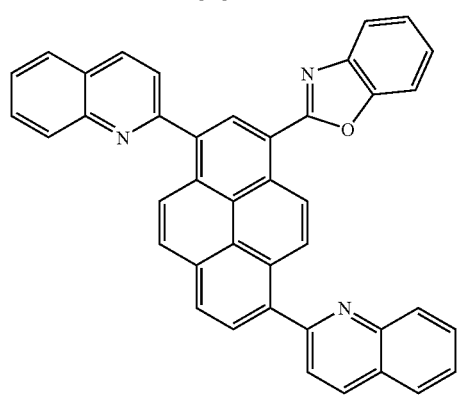
[85]
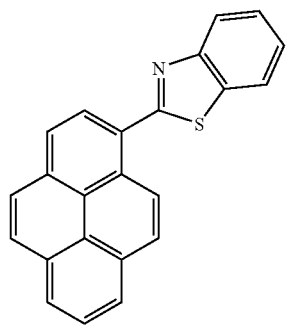
[86]
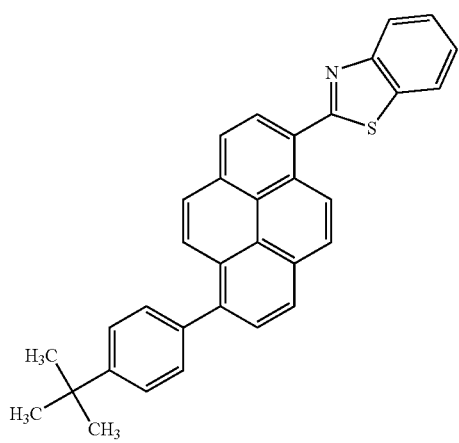
[87]
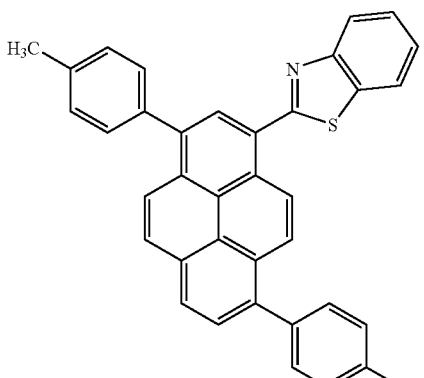
[88]
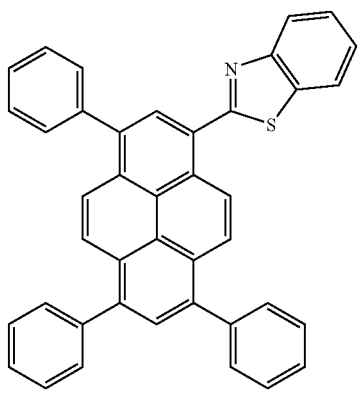
[89]
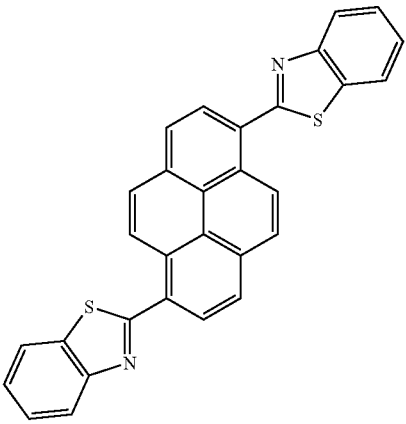
[90]

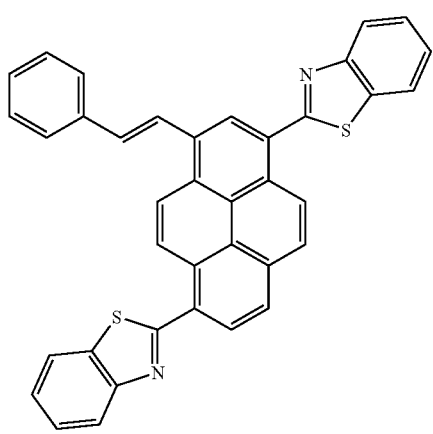
[91]
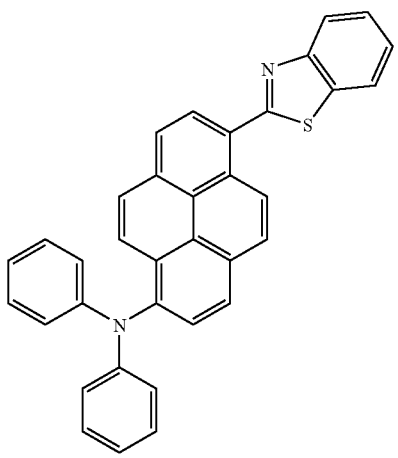
[94]
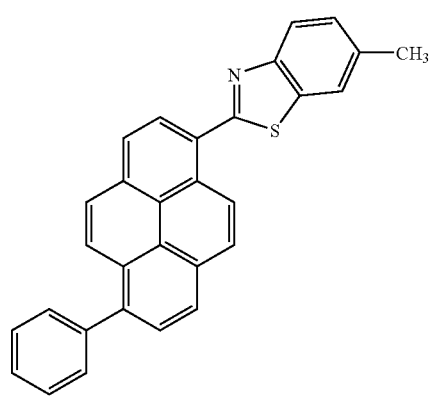
[92]
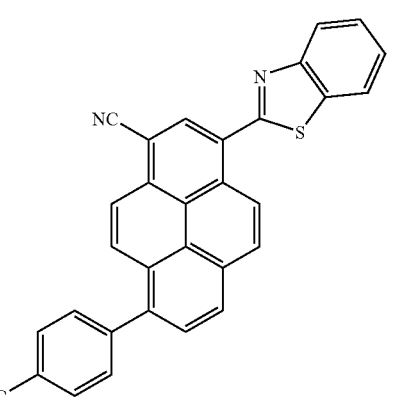
[95]
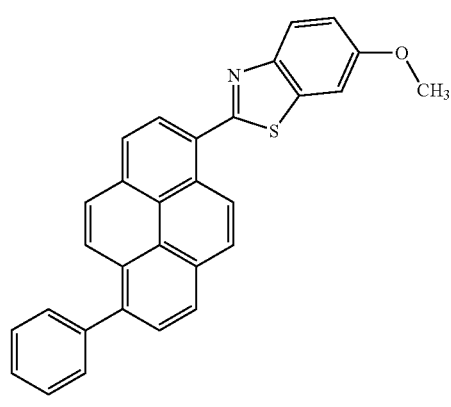
[93]
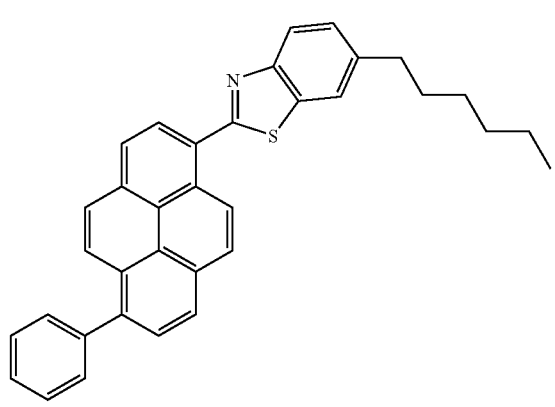
[96]

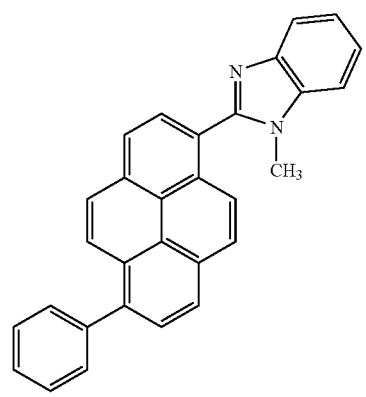
[97]
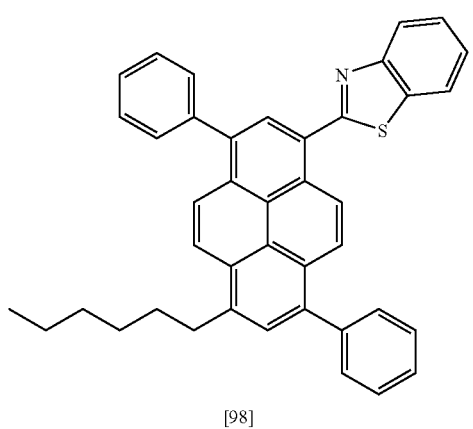
[98]
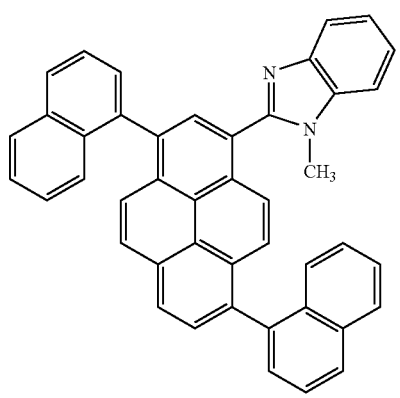
[99]
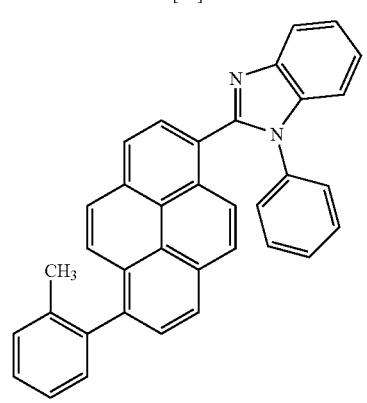
[100]
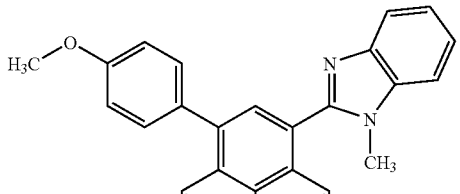
[101]
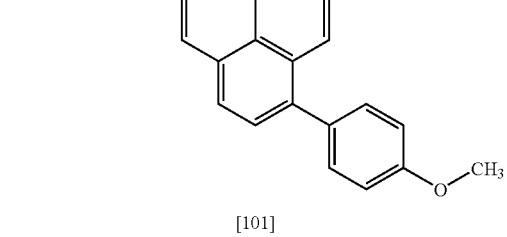
[102]
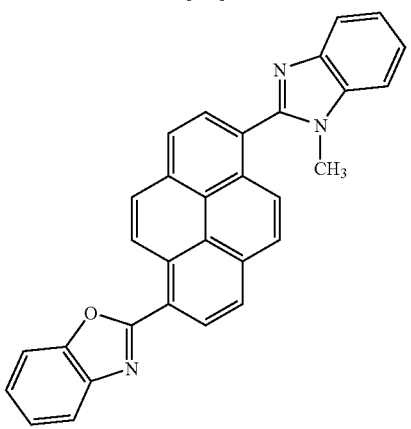
[103]
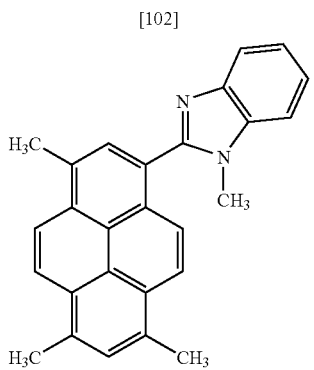
[104]
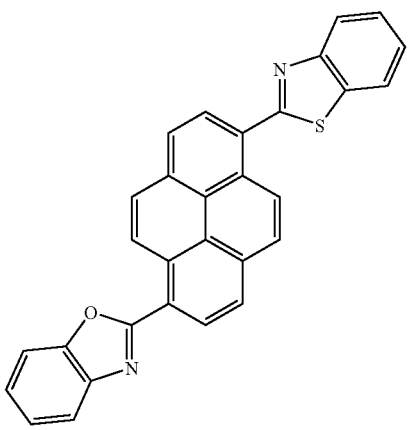

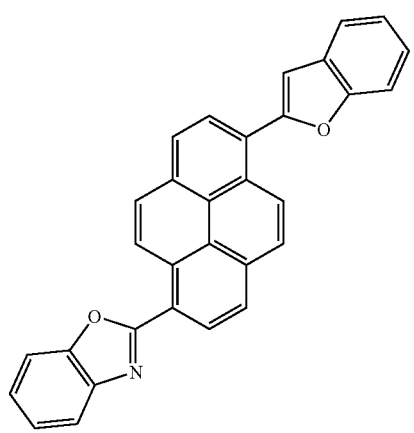
[105]
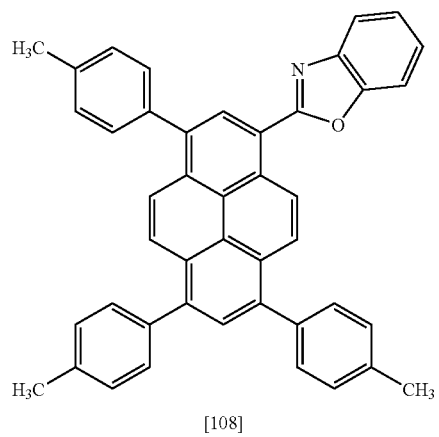
[108]
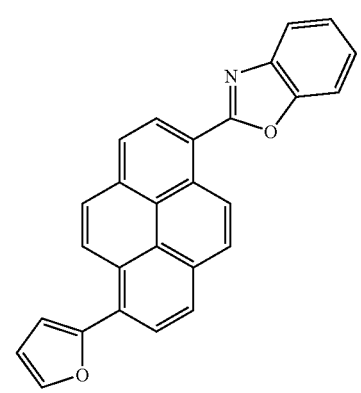
[106]
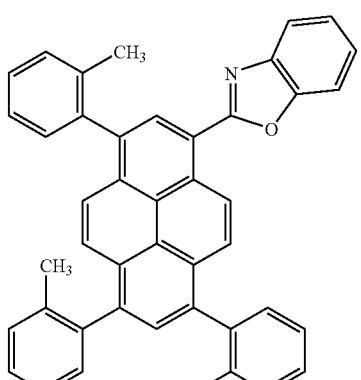
[109]
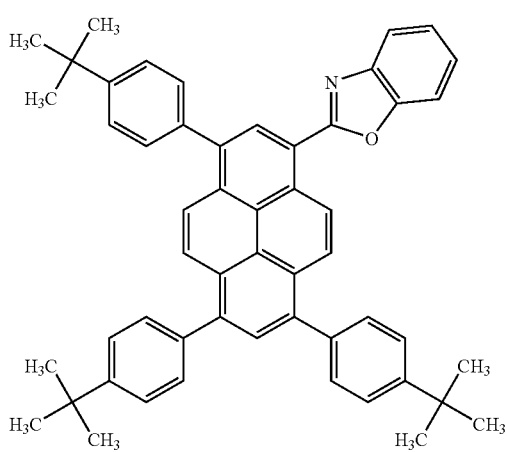
[107]
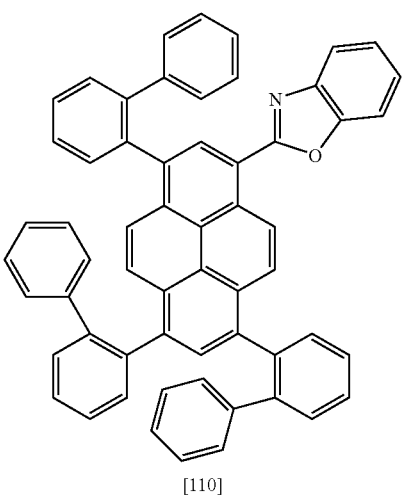
[110]

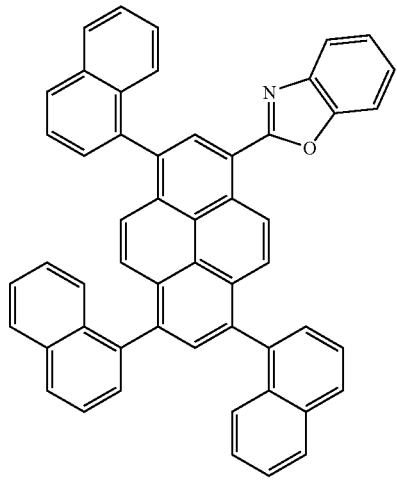
[111]
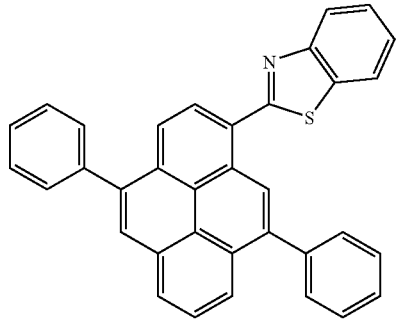
[112]
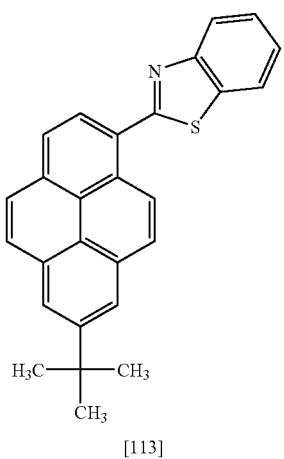
[113]
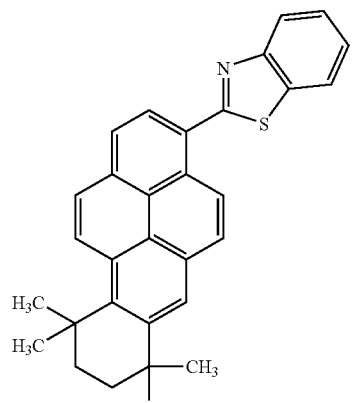
[114]
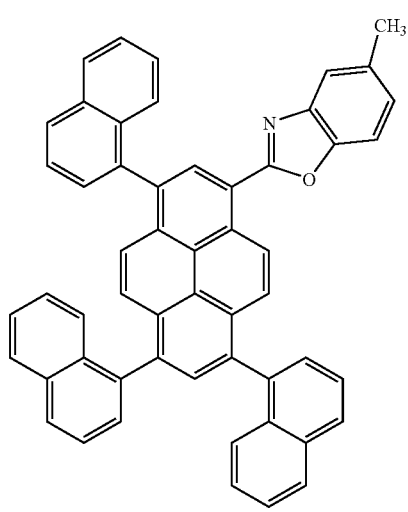
[115]
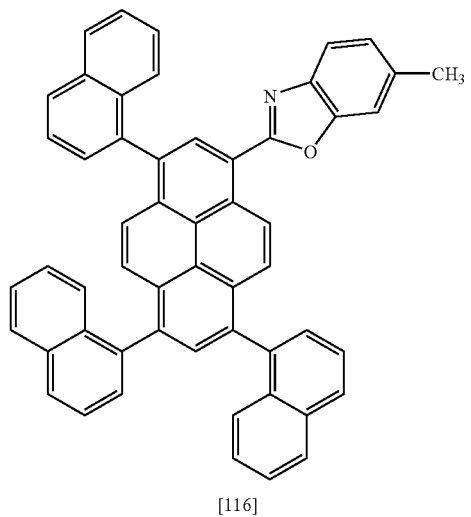
[116]

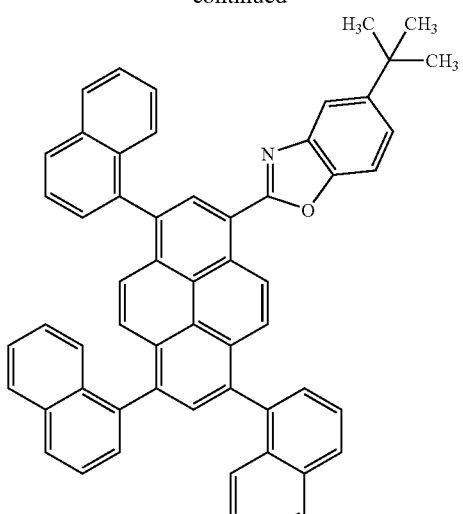
[117]
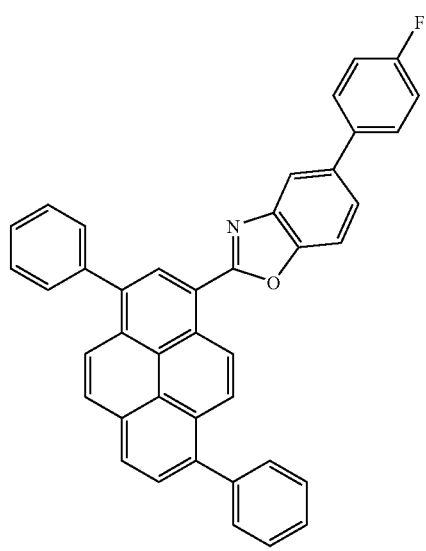
[118]
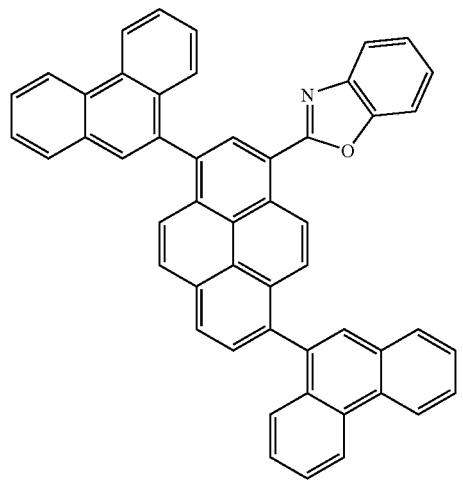
[119]
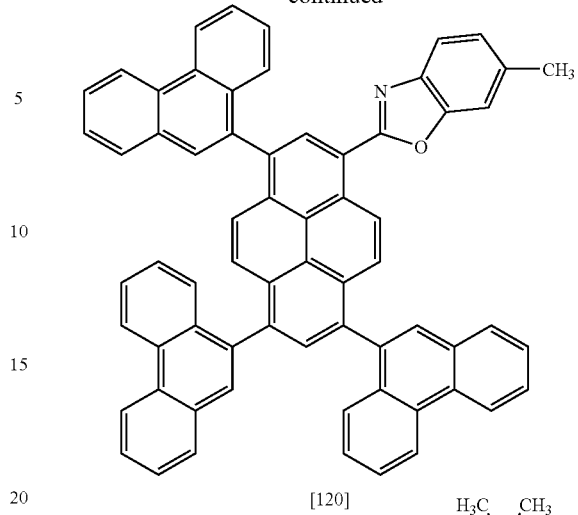
[120]
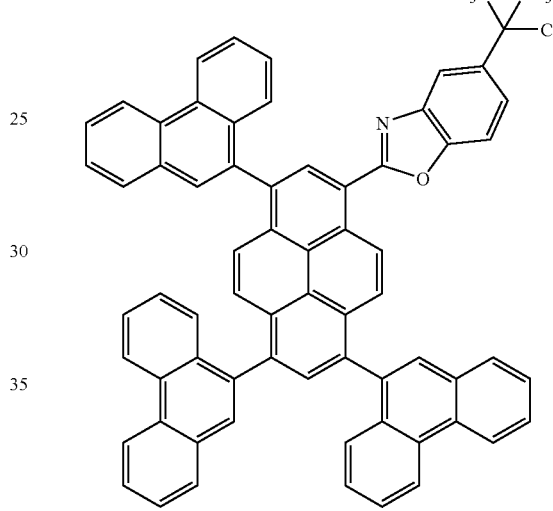
[121]
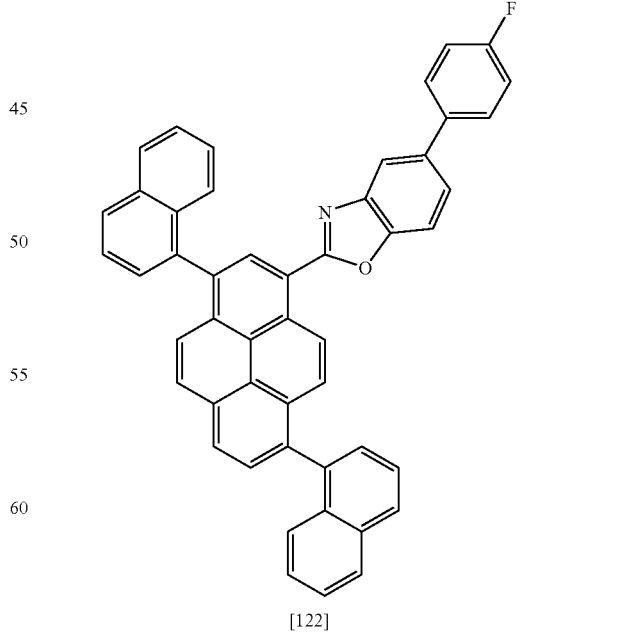
[122]

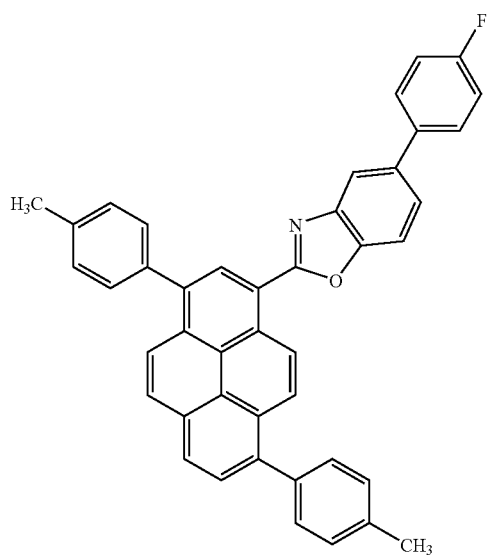
[123]
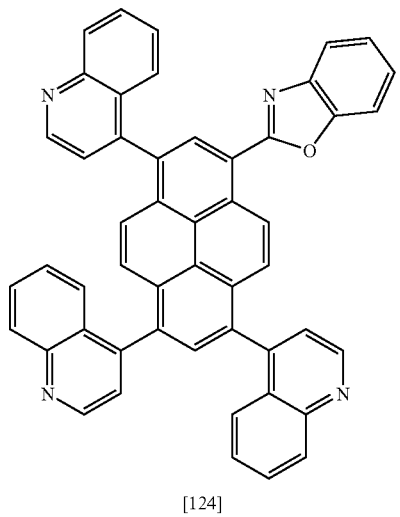
[124]
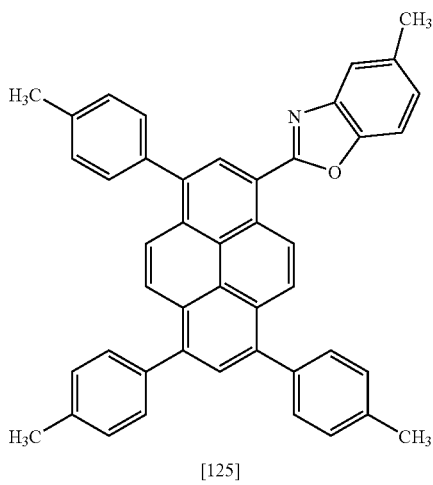
[125]
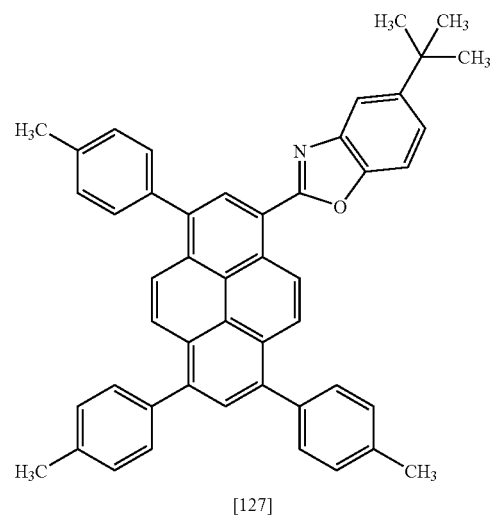
[126]
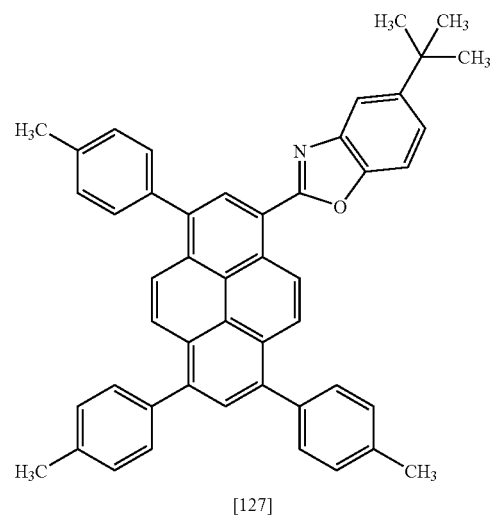
[127]
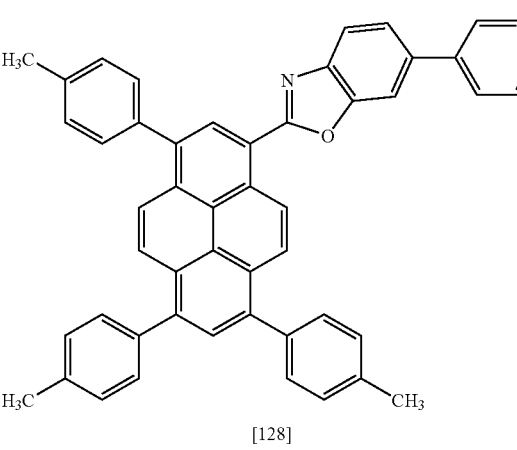
[128]

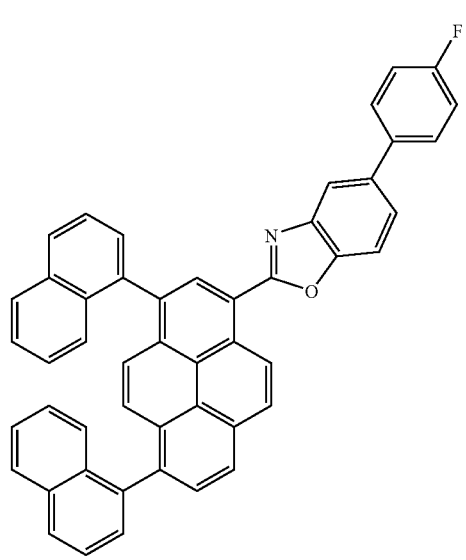
[129]
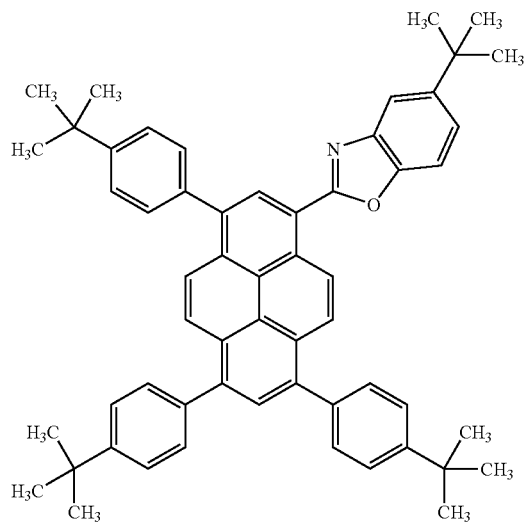
[132]
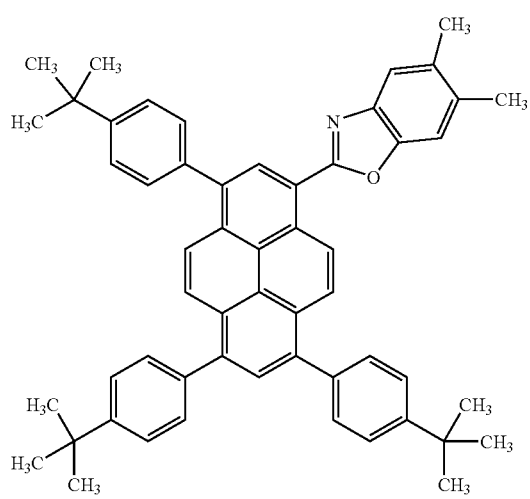
[130]
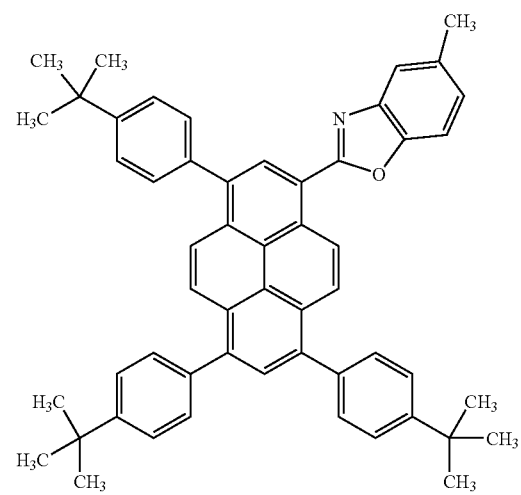
[133]
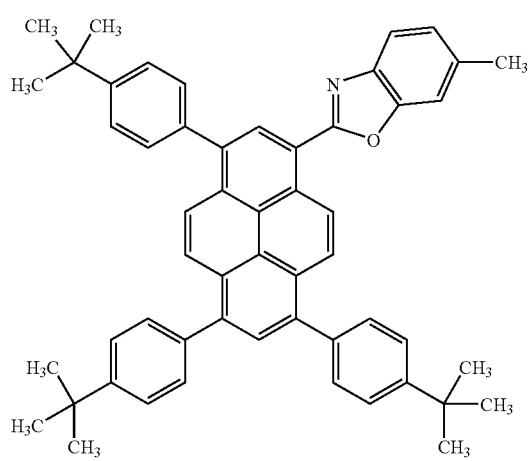
[131]
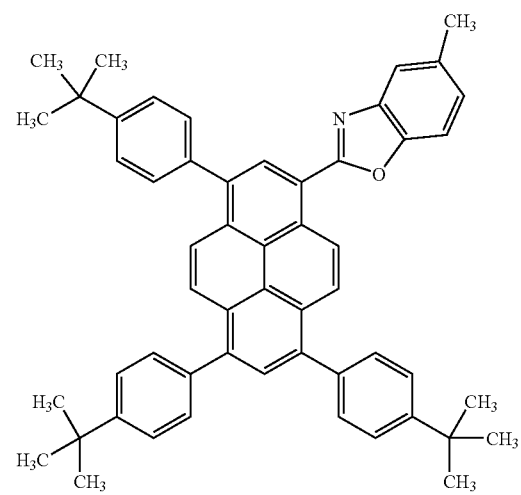
[134]

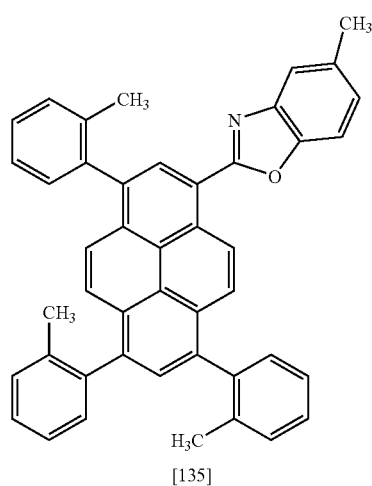
[135]
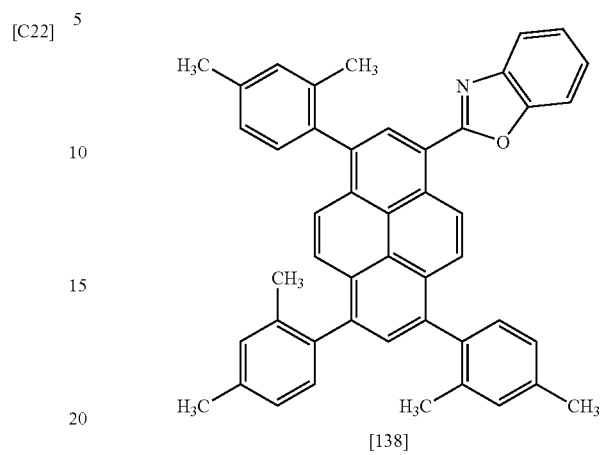
[138]
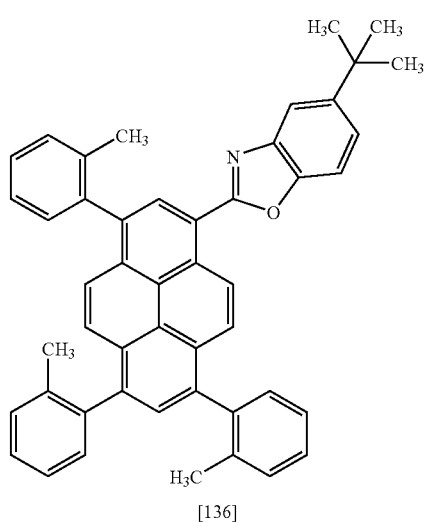
[136]
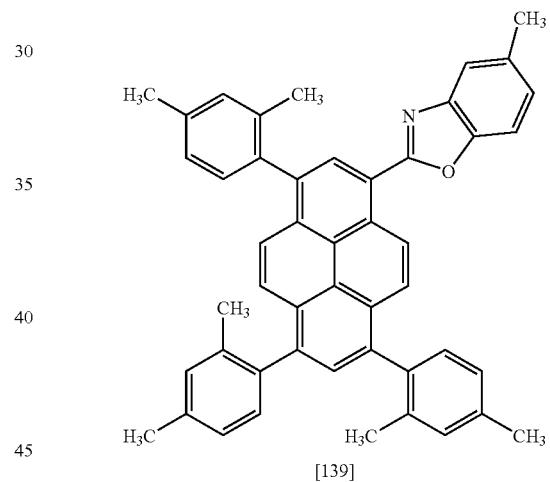
[139]
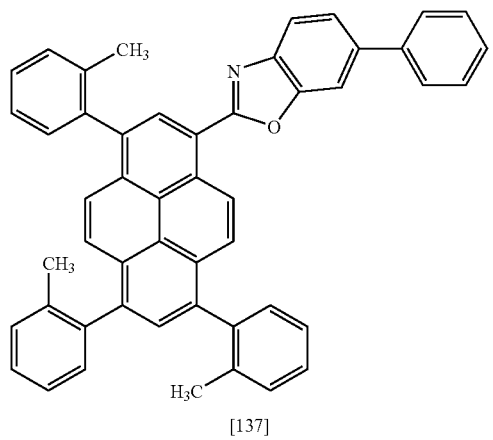
[137]
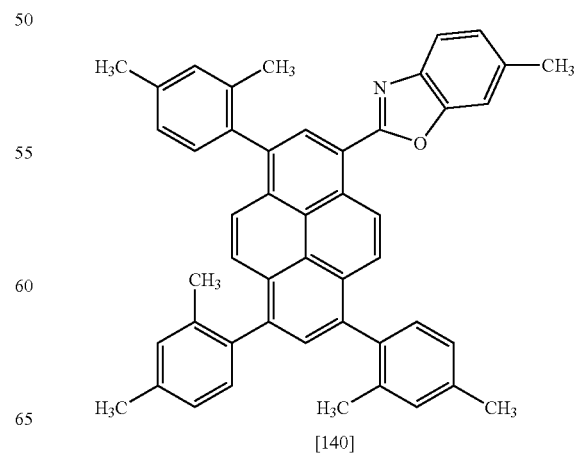
[140]

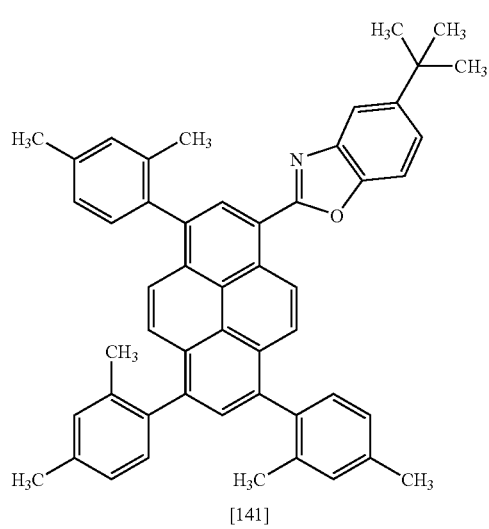
[141]
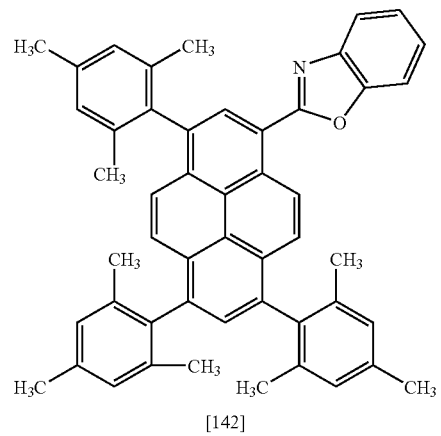
[142]
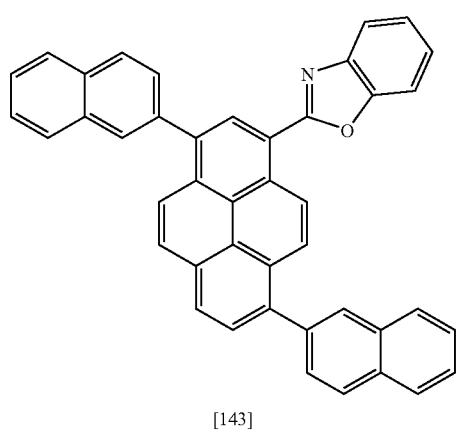
[143]
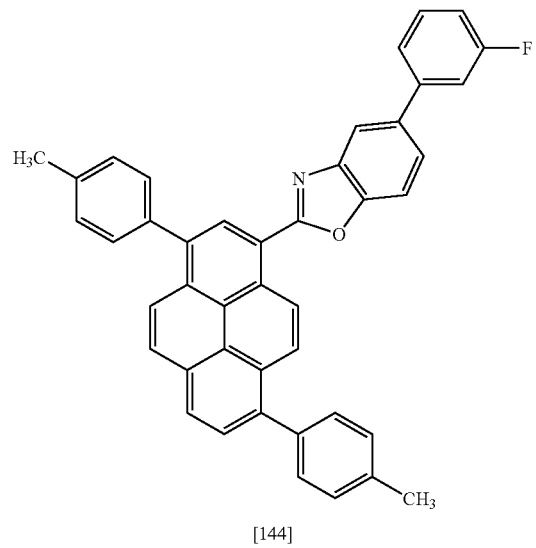
[144]
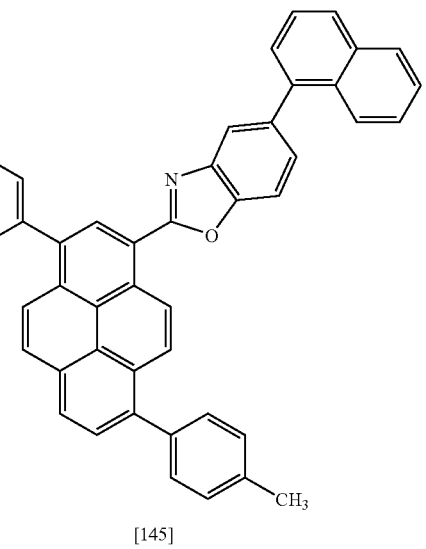
[145]
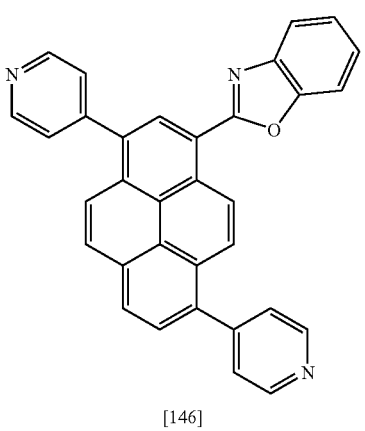
[146]

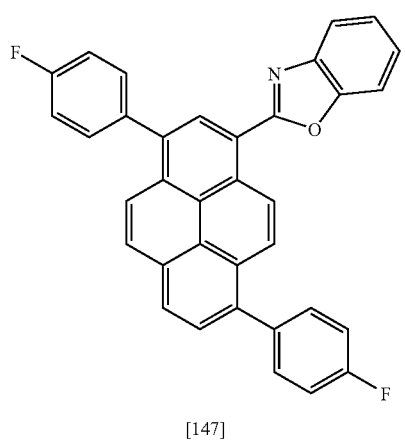
[147]
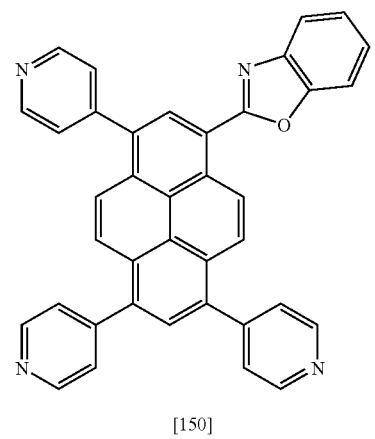
[150]
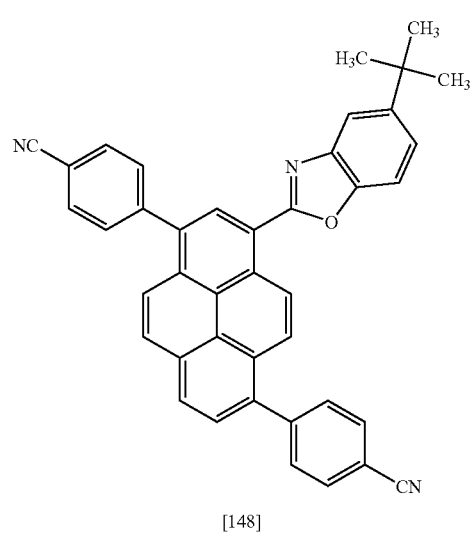
[148]
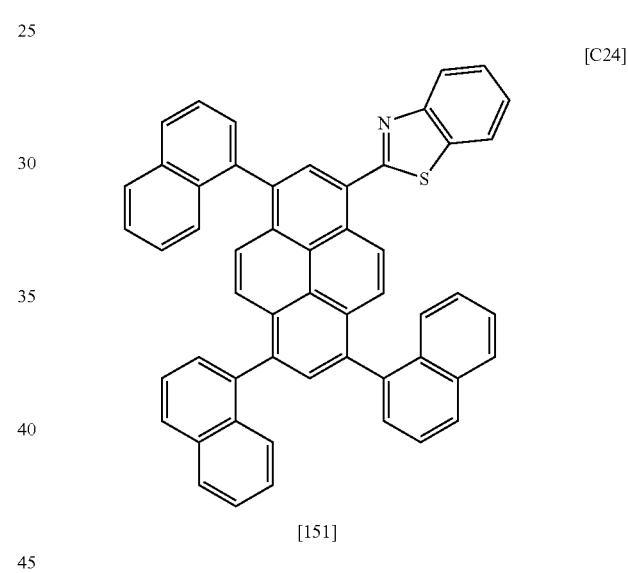
[151]
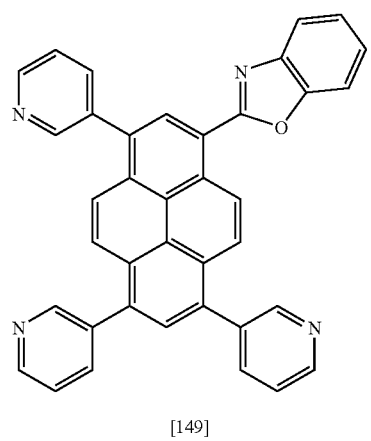
[149]
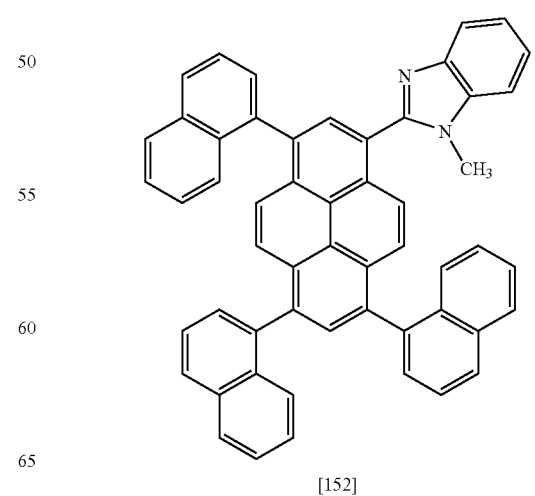
[152]

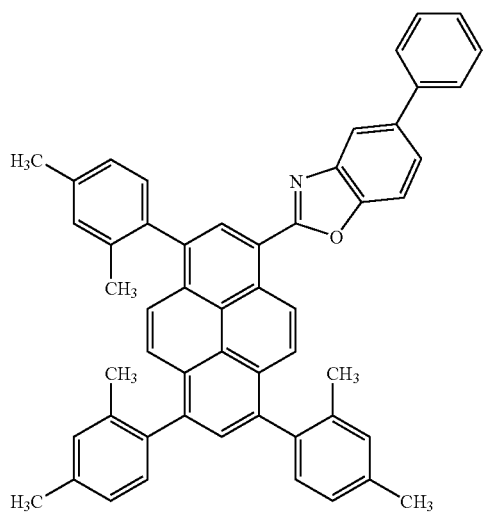
[153]
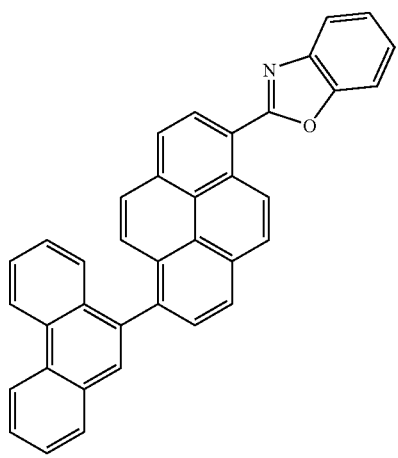
[154]
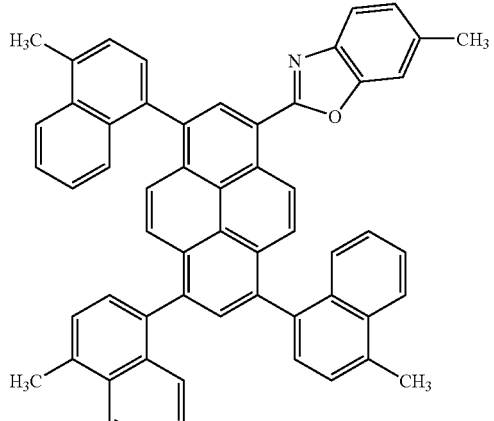
[155]
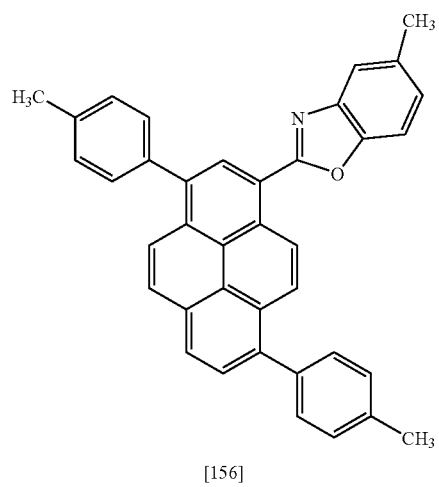
[156]
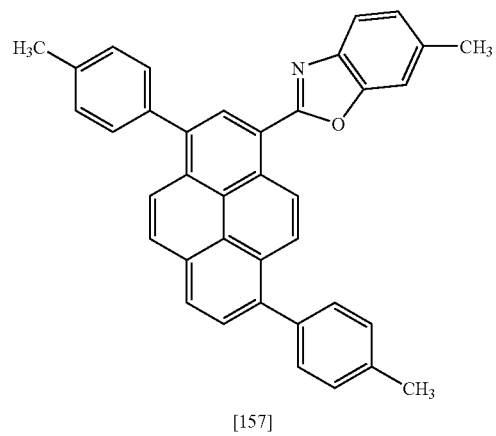
[157]
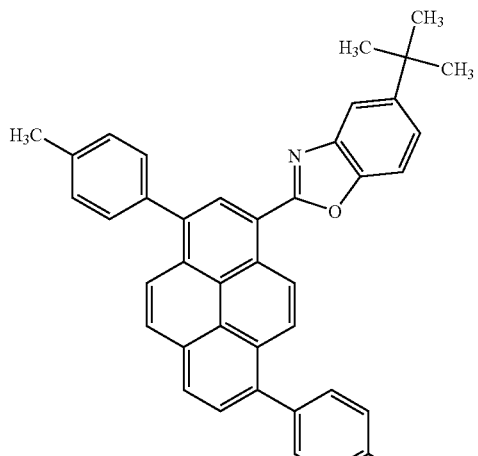
[158]

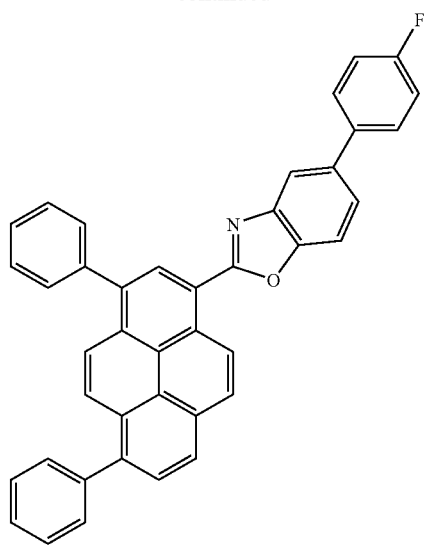
[159]
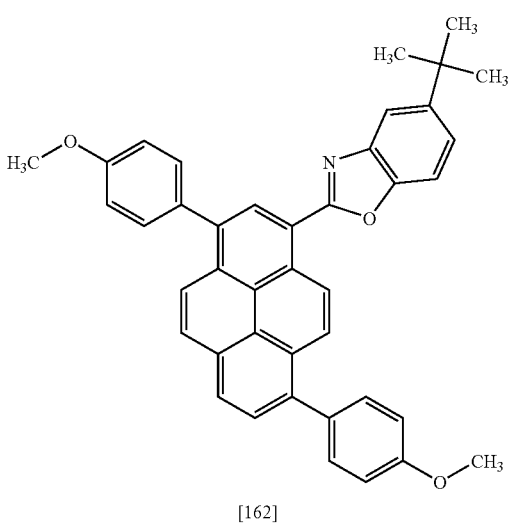
[162]
[C25]
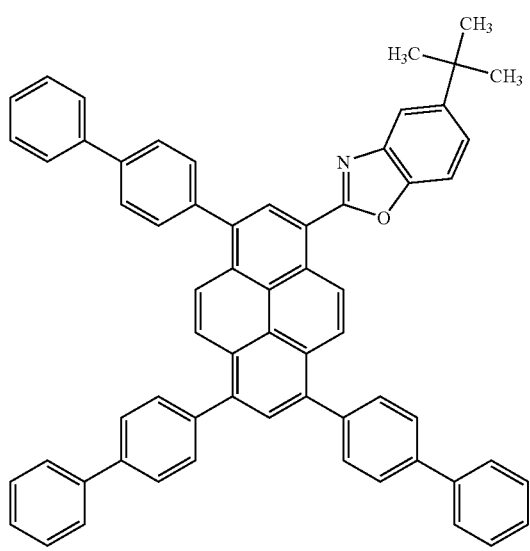
[160]
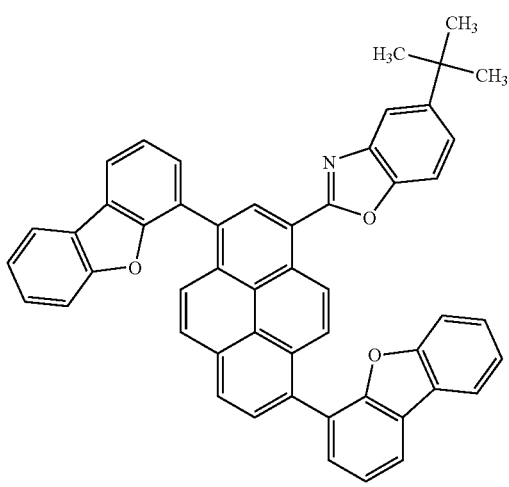
[163]
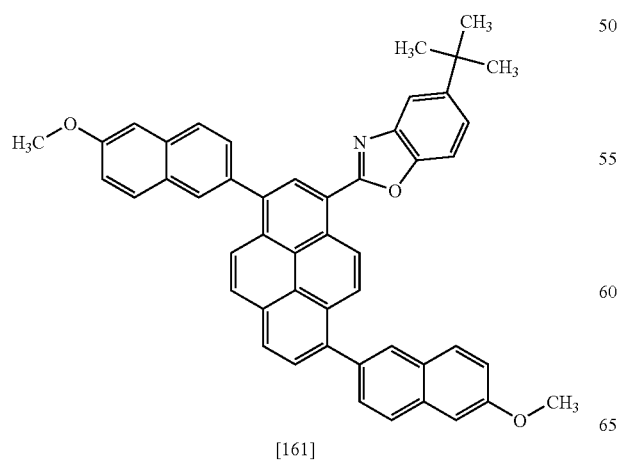
[161]
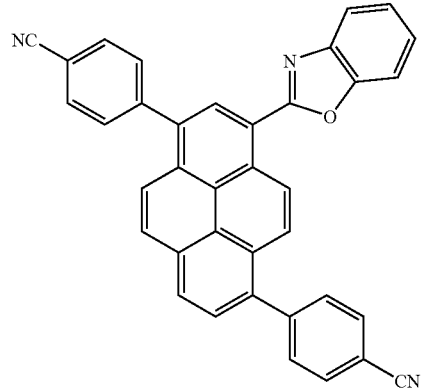
[164]

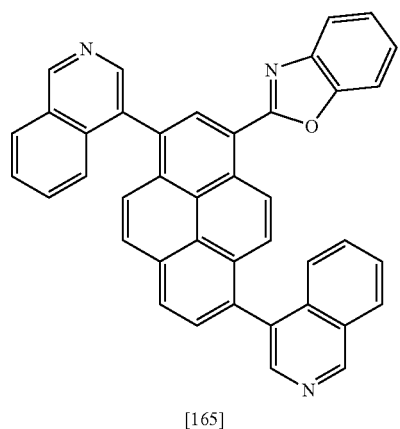
[165]
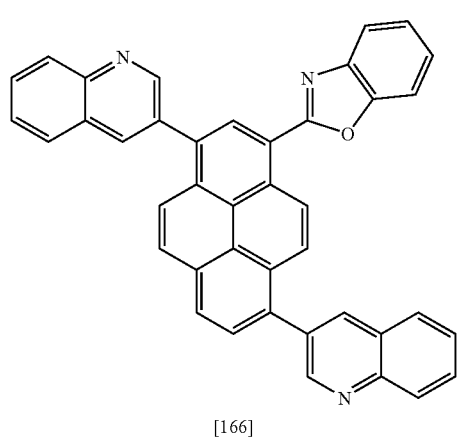
[166]
[C26]
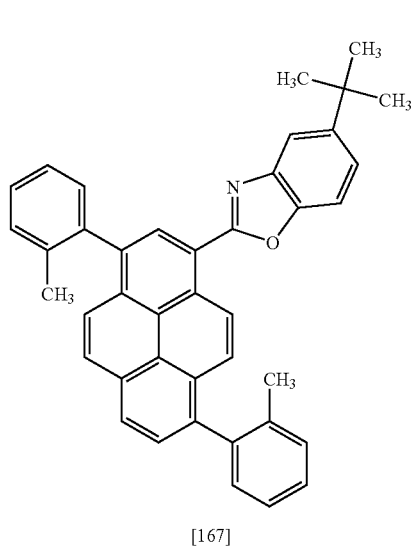
[167]
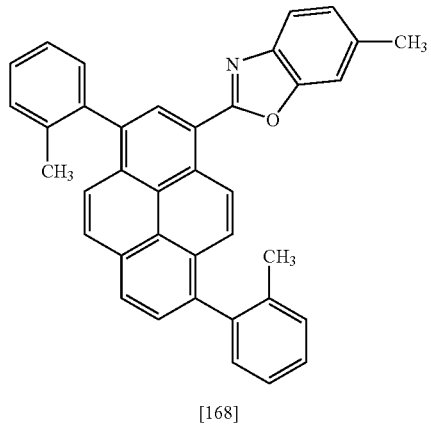
[168]
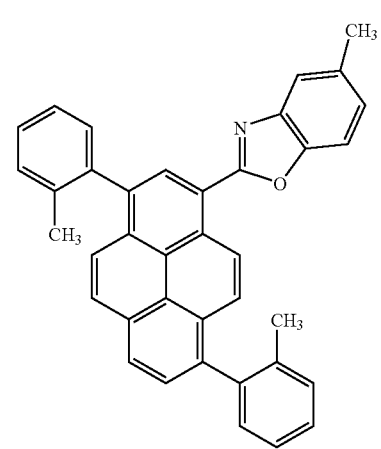
[169]
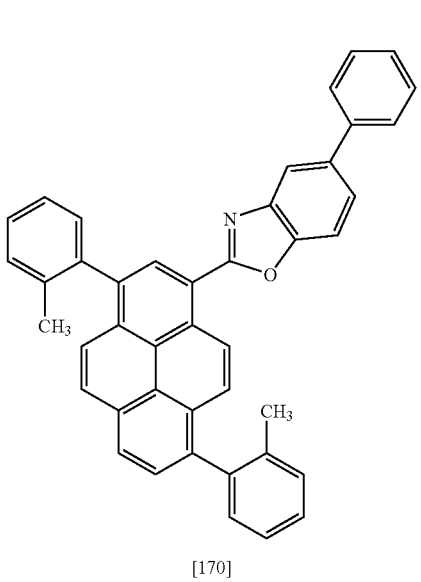
[170]

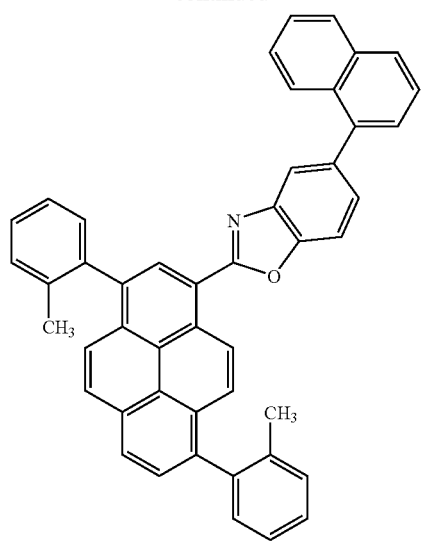
[171]
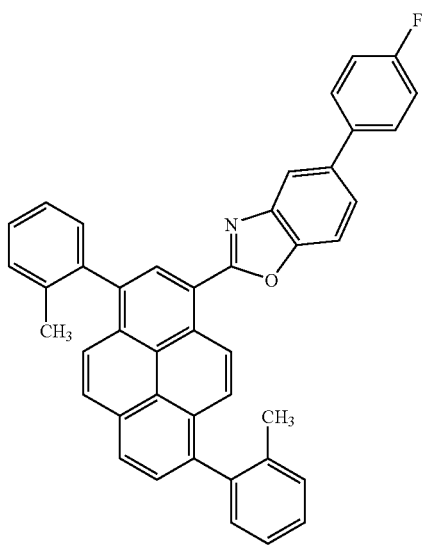
[172]
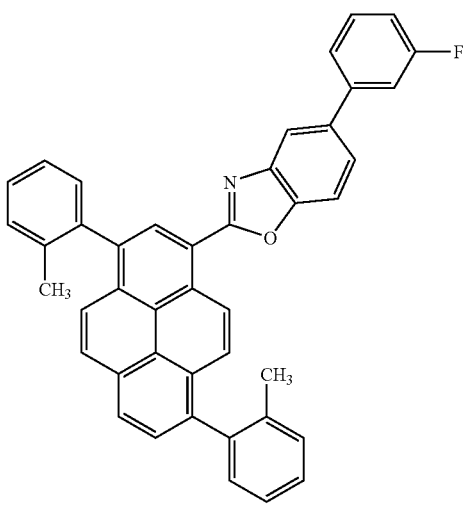
[173]
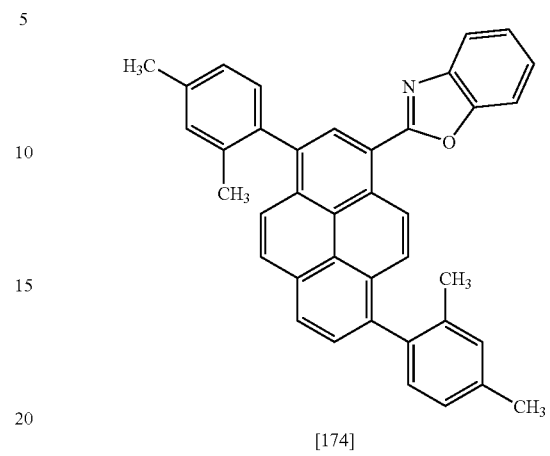
[174]
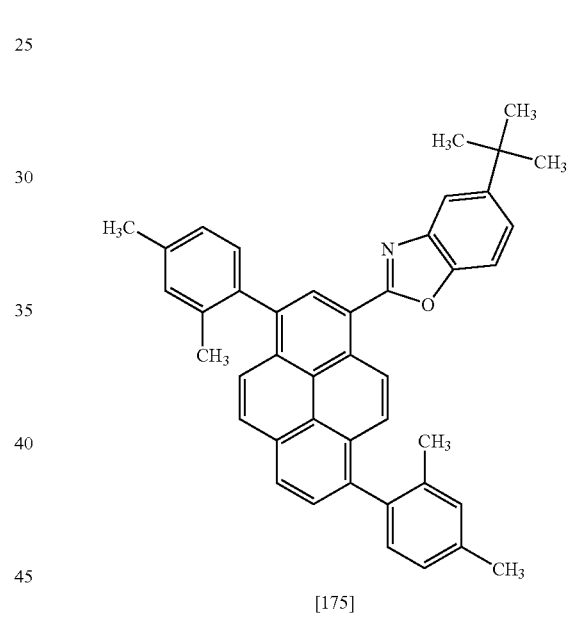
[175]
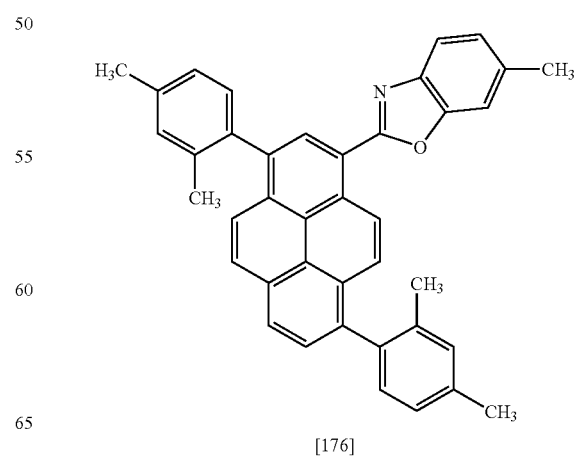
[176]

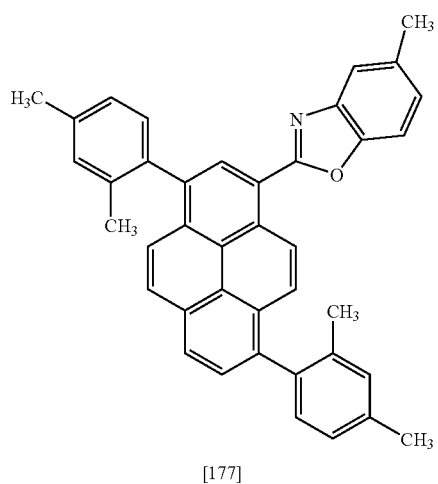
[177]
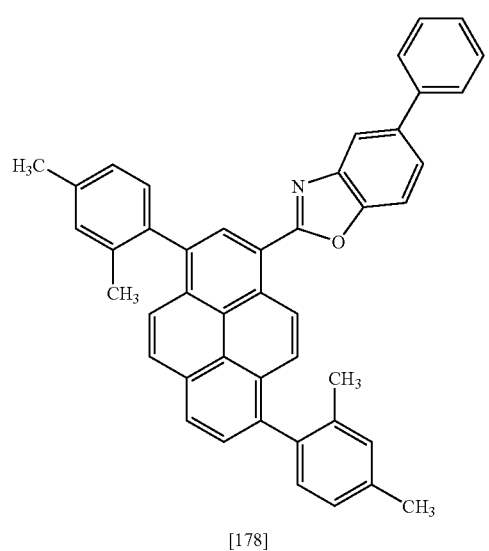
[178]
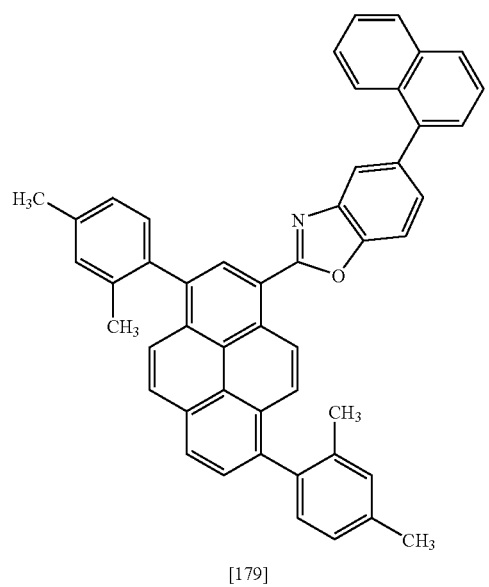
[179]
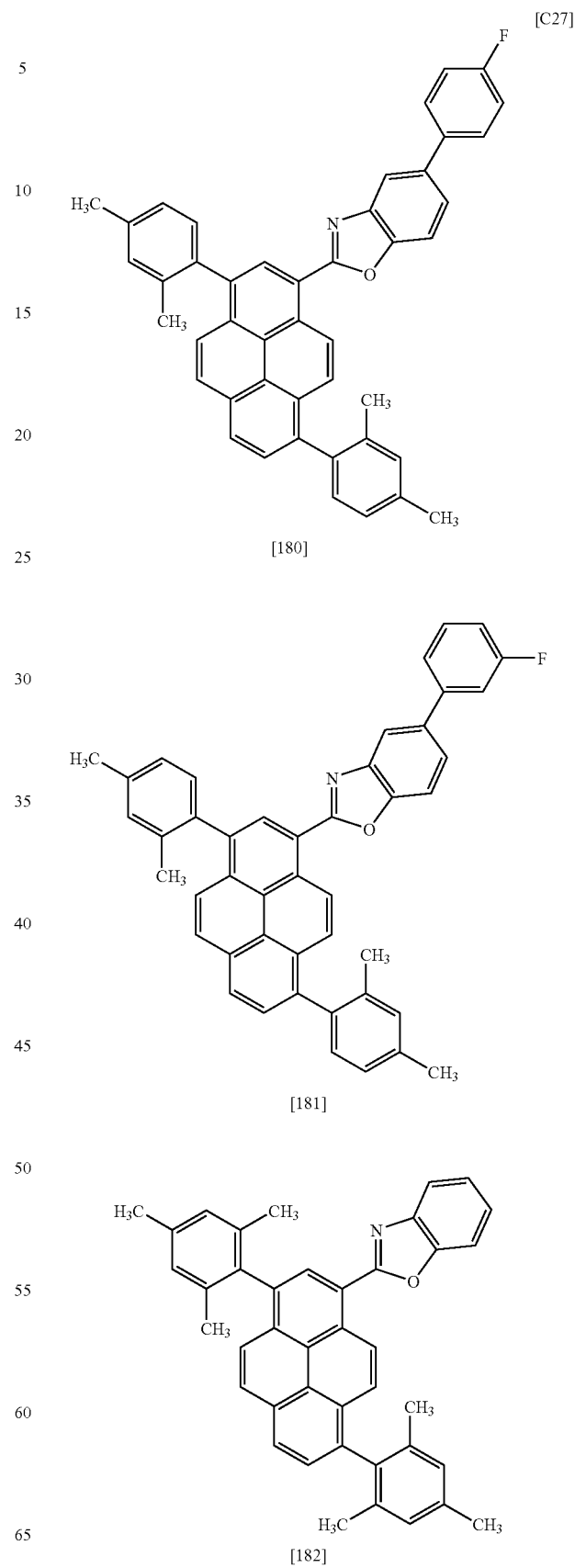
[180]
[181]
[182]

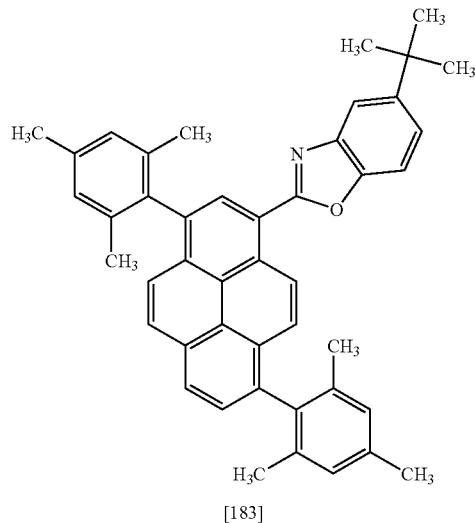
[183]
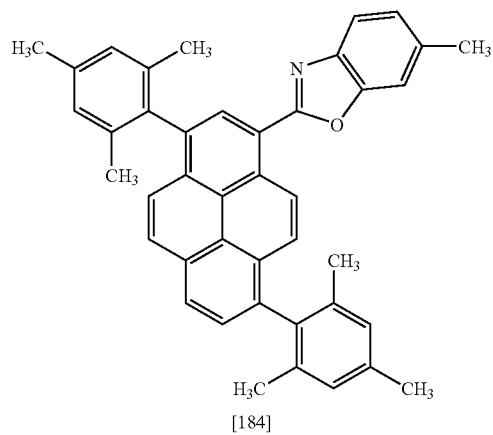
[184]
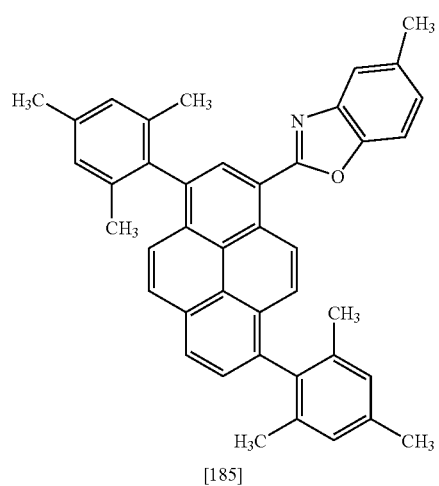
[185]
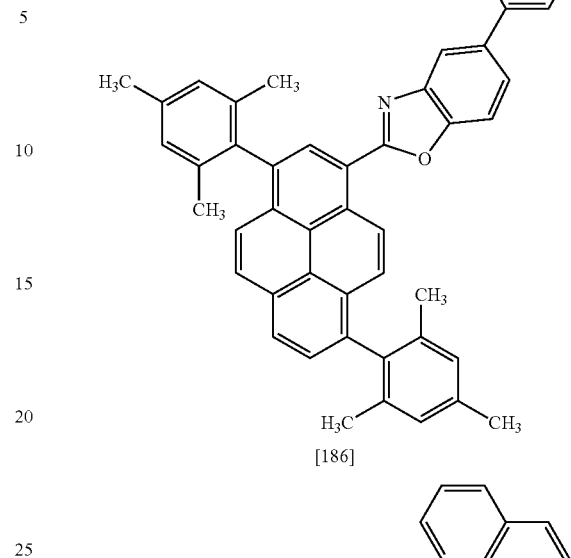
[186]
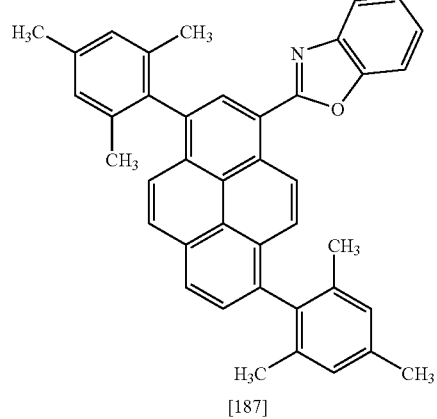
[187]
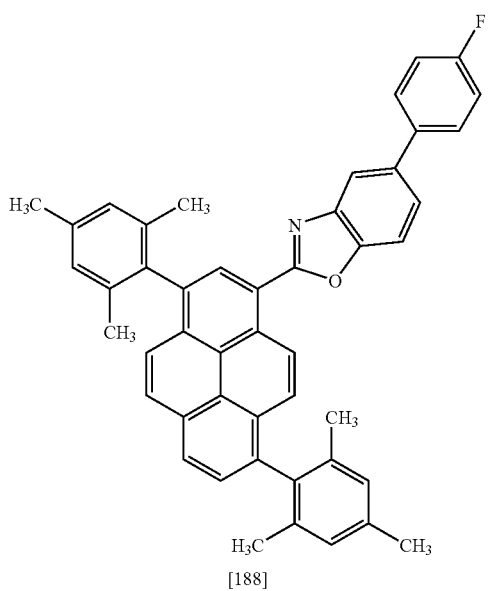
[188]

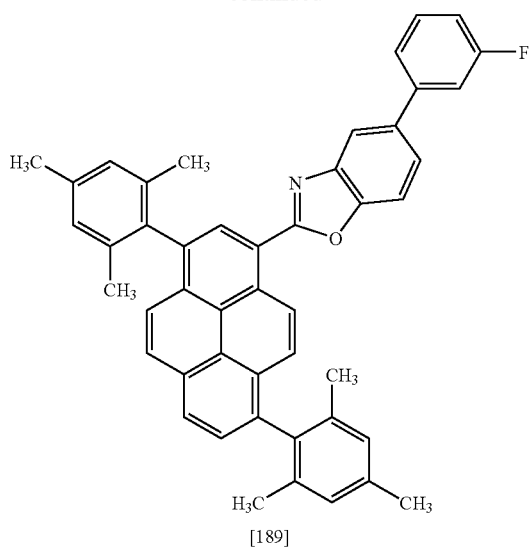
[189]
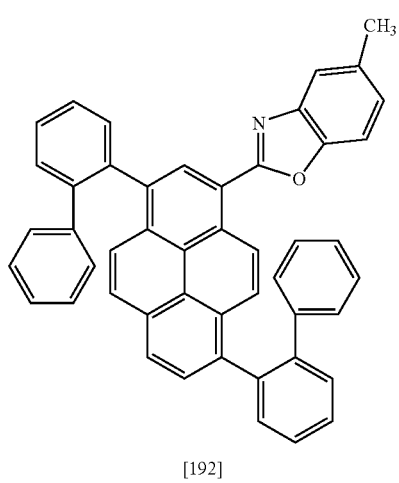
[192]
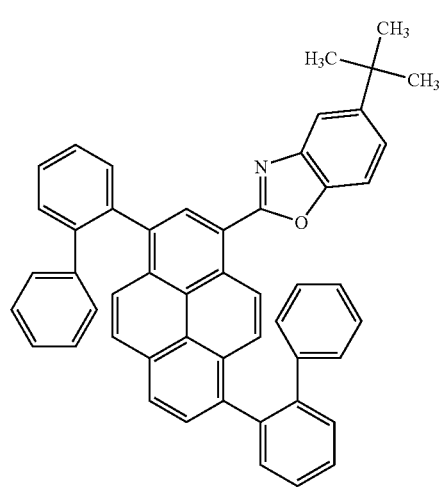
[190]
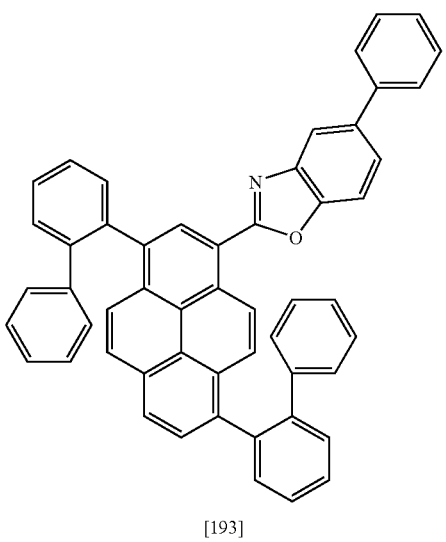
[193]
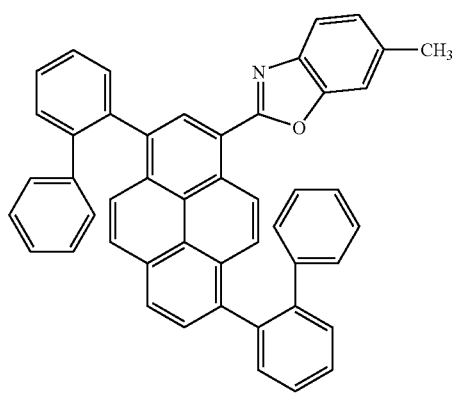
[191]
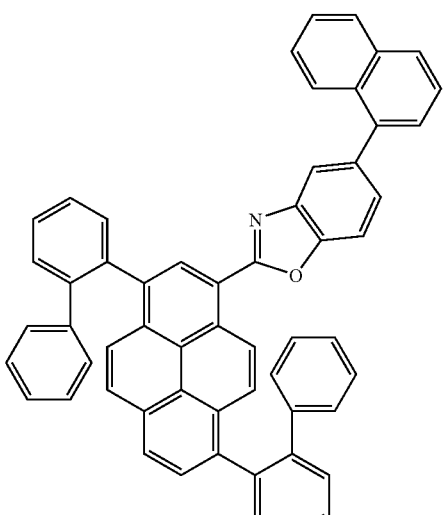
[194]

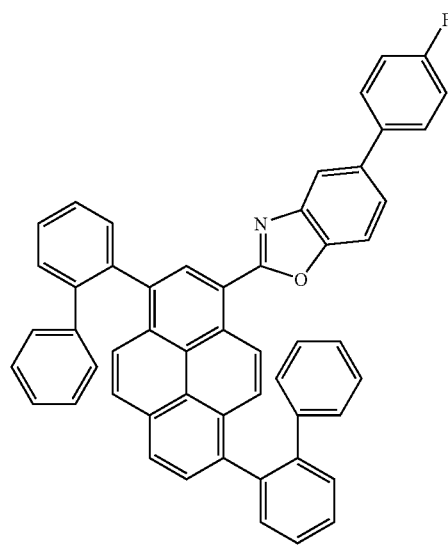
[195]
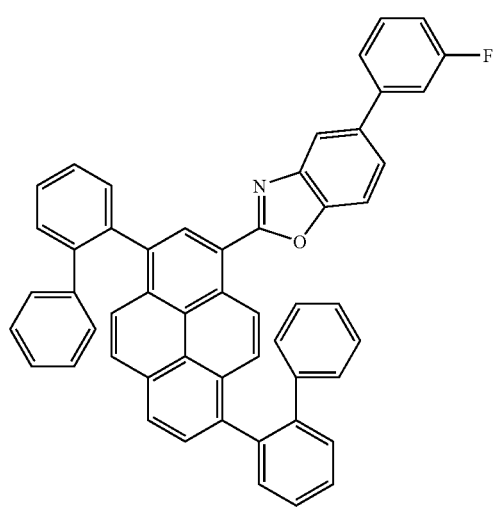
[196]
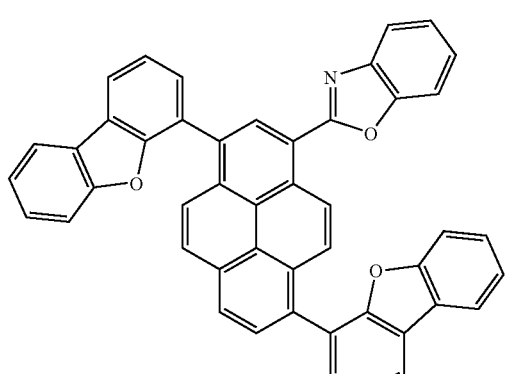
[197]
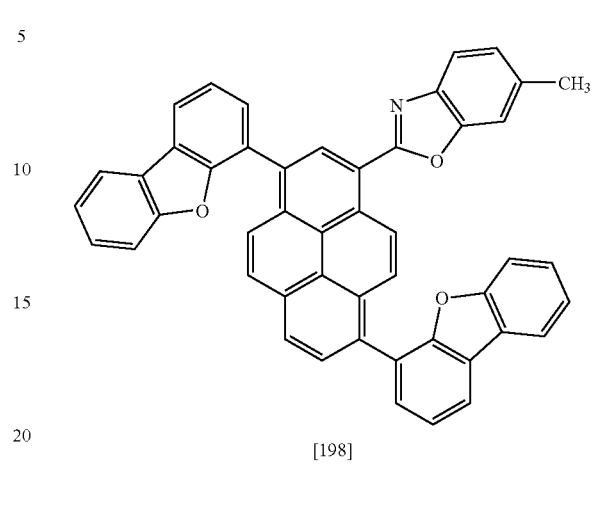
[198]
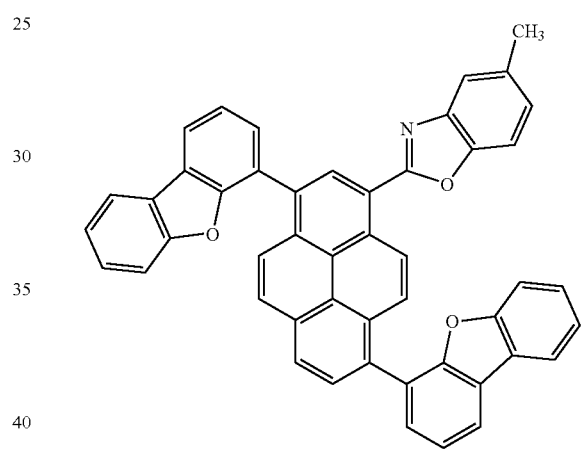
[199]
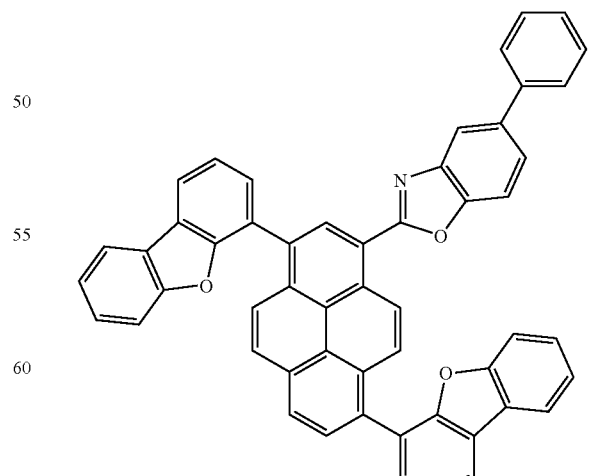
[200]

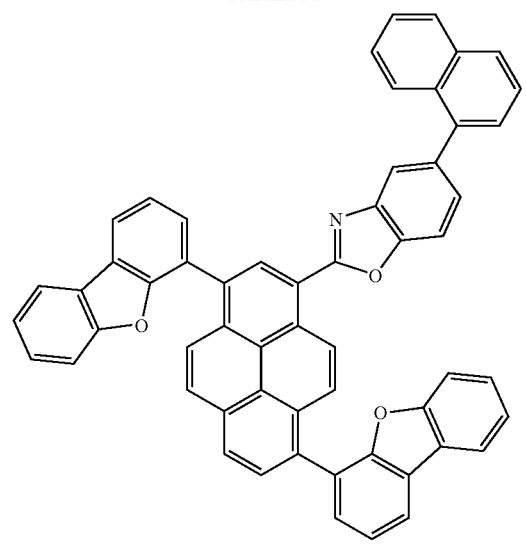
[201]
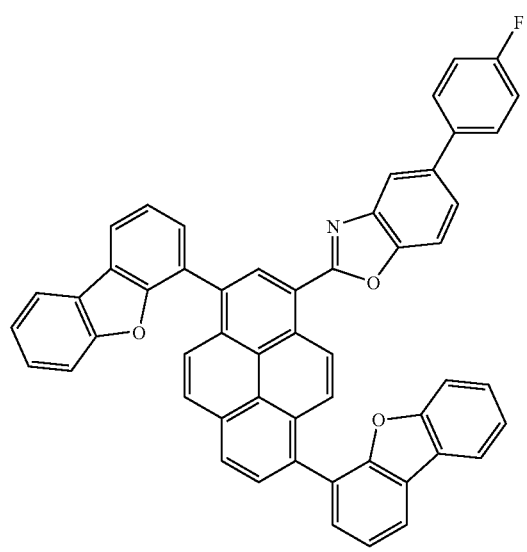
[202]
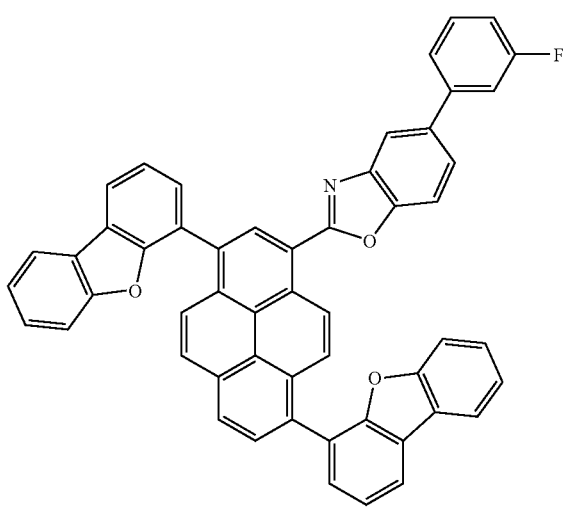
[203]
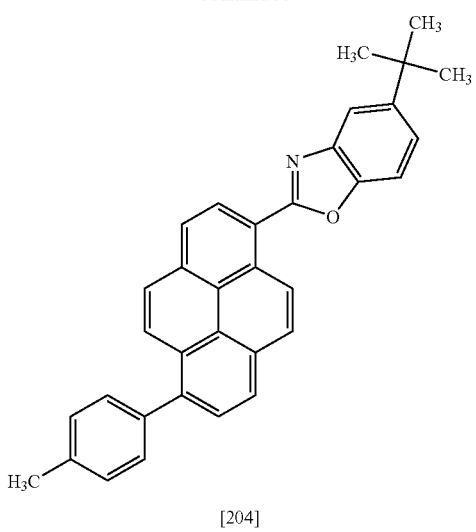
[204]
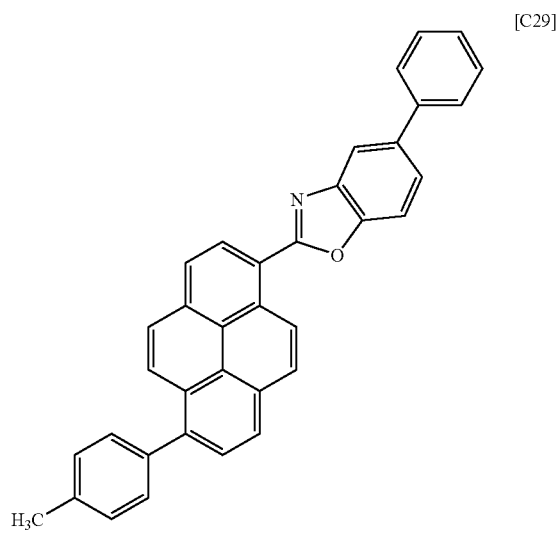
[205]
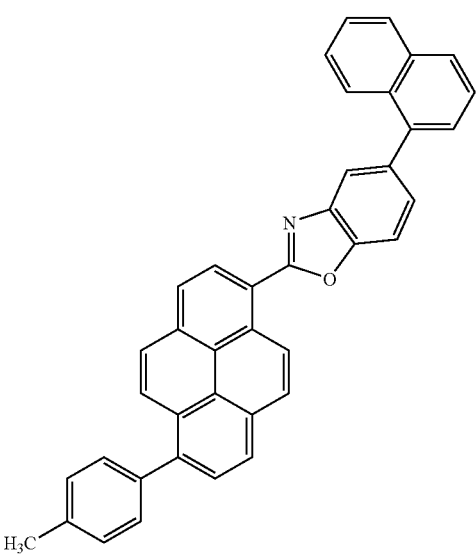
[206]

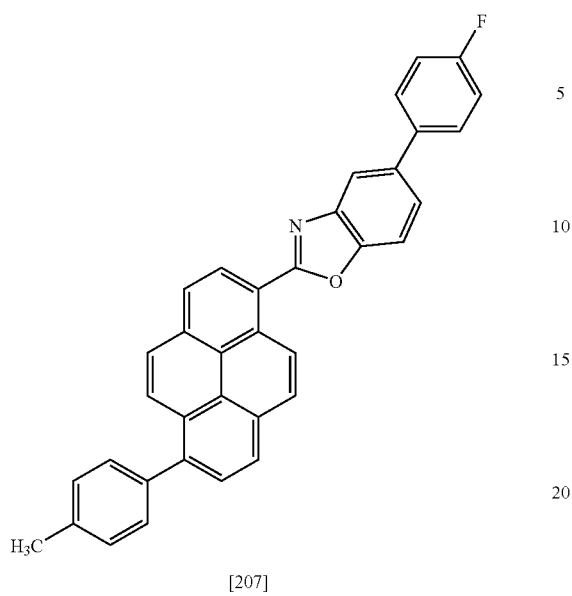
[207]
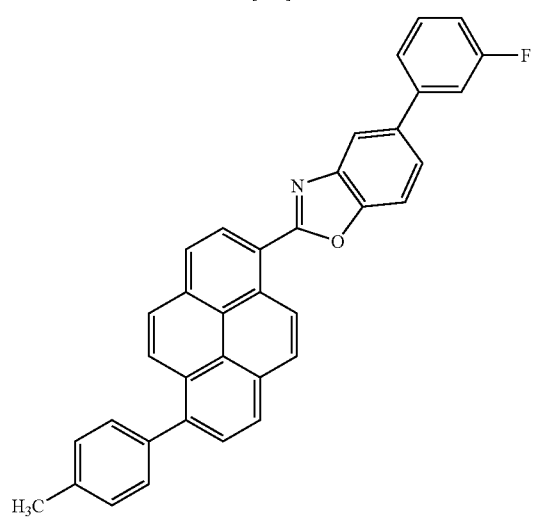
[208]
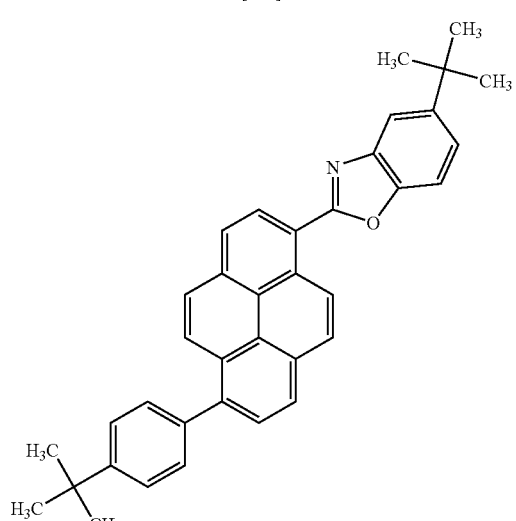
[209]
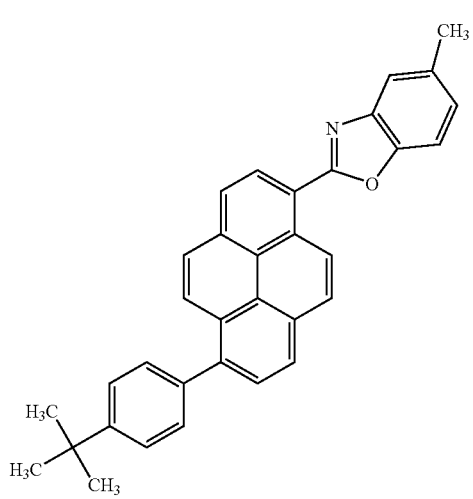
[210]
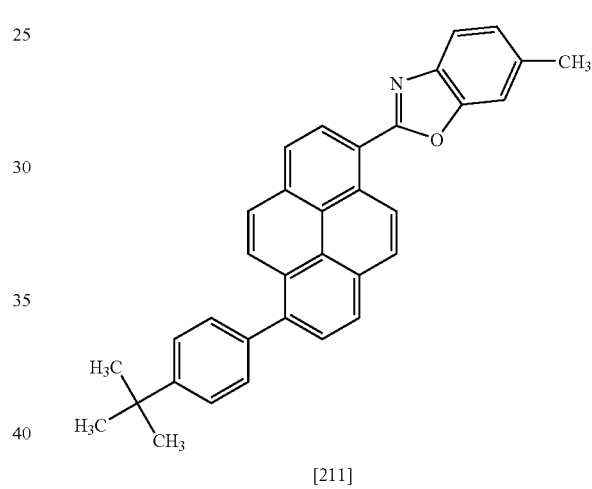
[211]
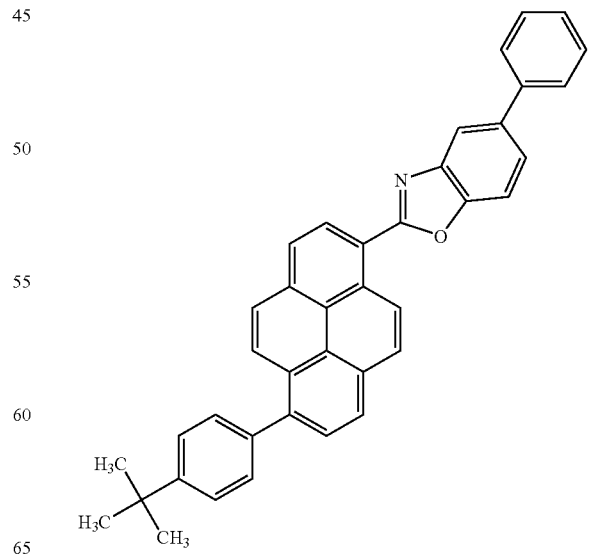
[212]

77
-continued
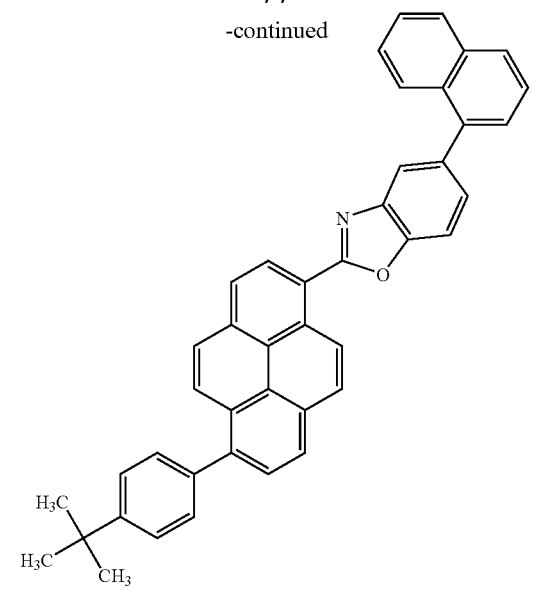
[213]
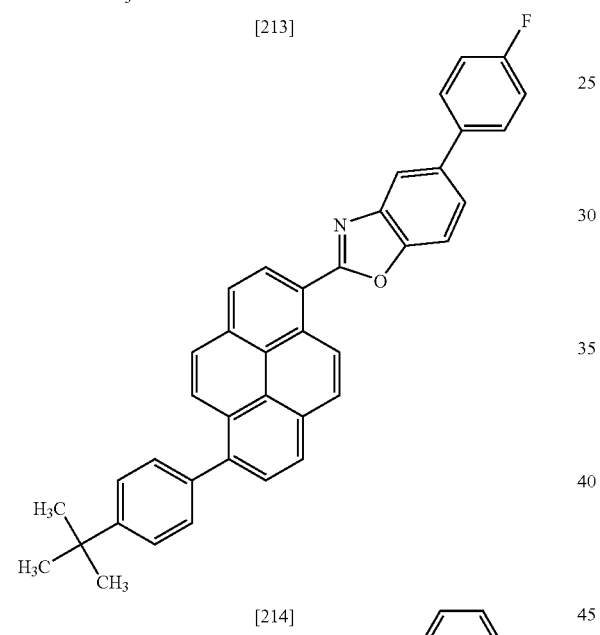
[214]
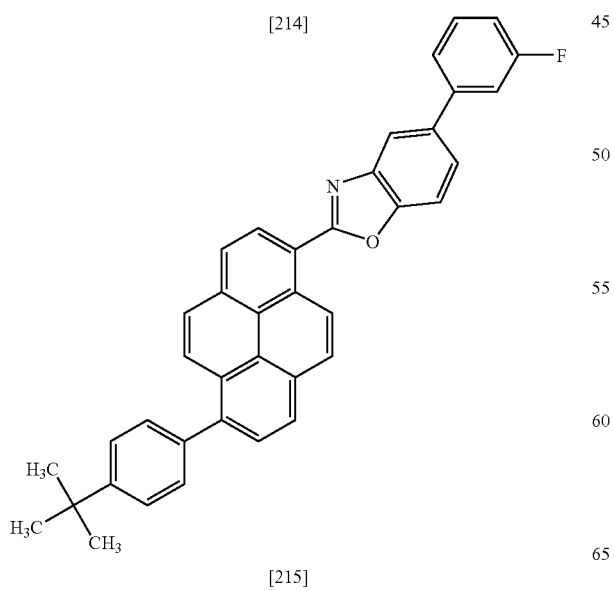
[215]
78
-continued
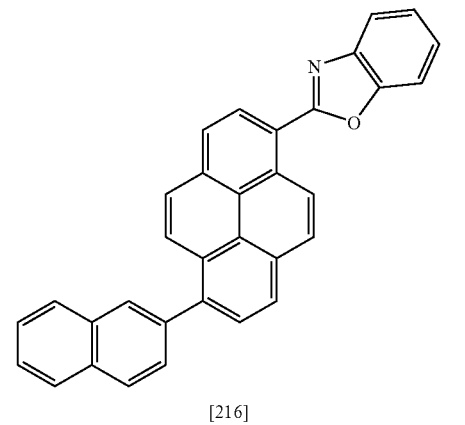
[216]
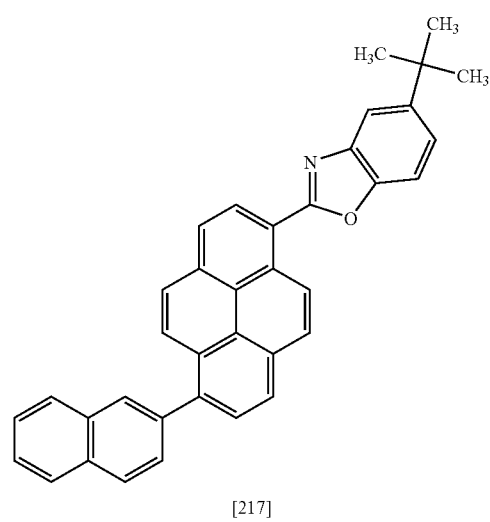
[217]
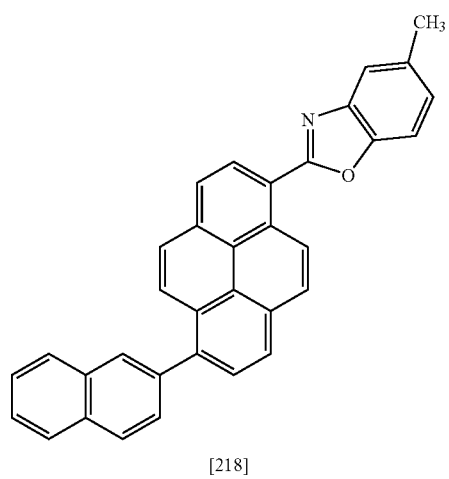
[218]

-continued

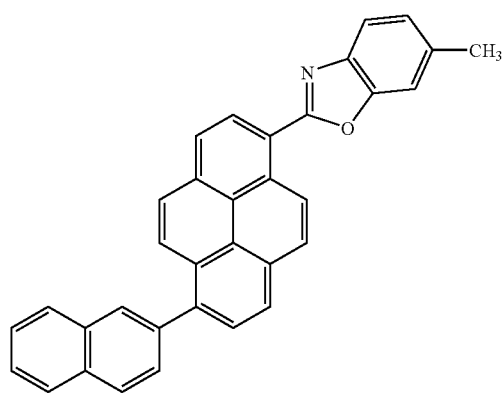

[219]

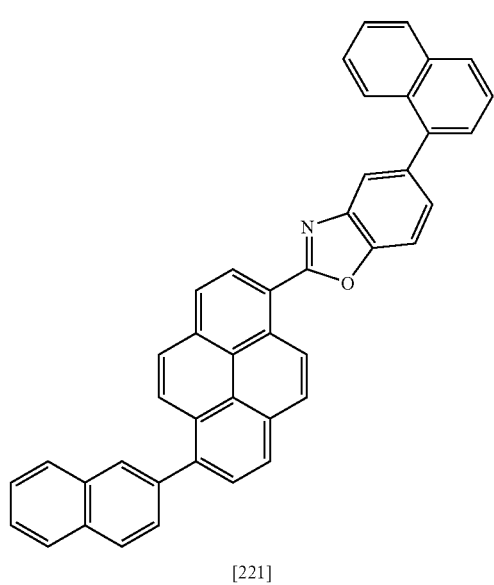

[220]

[221]

-continued

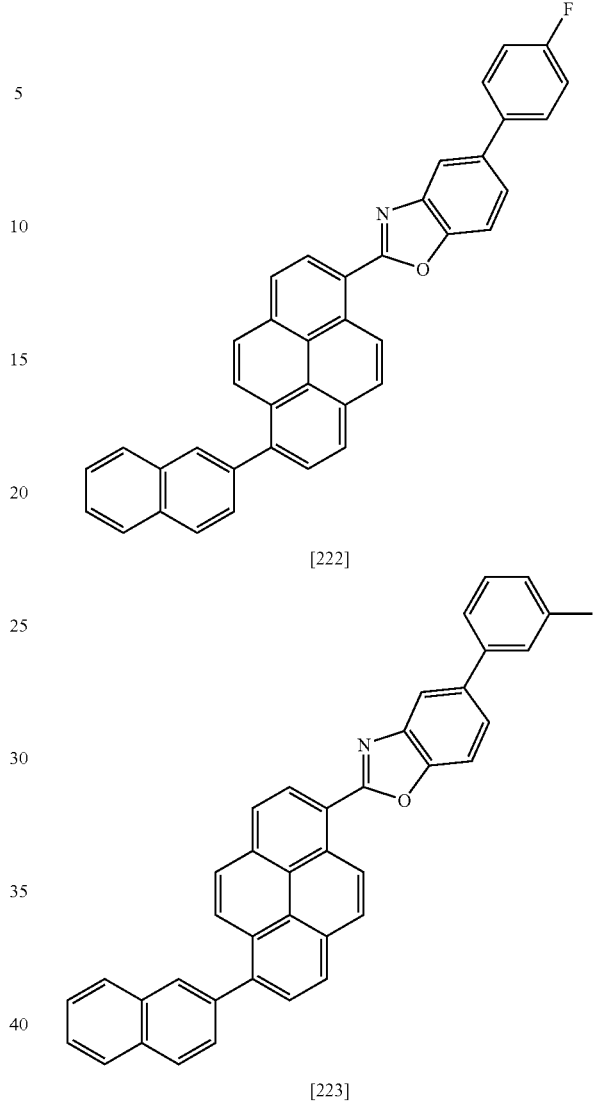

[222]

[223]

A publicly known method can be used for synthesizing a pyrene compound represented by the general formula (1). Examples of a method of introducing an aryl group or heteroaryl group to a pyrene skeleton include a method of using a coupling reaction of a halogenated pyrene derivative and an aryl derivative or heteroaryl derivative in the presence of palladium catalyst or nickel catalyst. Examples of a method of introducing an azolyl group to apyrene skeleton include a method of using a coupling reaction of a halogenated pyrene derivative and an azole derivative under palladium catalyst, and a method of using a condensation reaction of pyrene aldehyde or pyrene carboxylic acid derivative and 2-aminophenol or 2-aminothiophenol, which examples are not limited thereto.

Next, an embodiment of a light-emitting device in the present invention is described in detail by referring to examples. A light-emitting device of the present invention is composed of at least an anode, a cathode and an organic layer made of a light-emitting device material interposed between the anode and the cathode.

The anode used in the present invention is not particularly limited if it is a material capable of efficiently injecting a hole into the organic layer, and a material with comparatively high work function is preferably used; examples thereof include conductive metal oxides such as tin oxide, indium oxide, indium zinc oxide and indium tin oxide (ITO), metals such as gold, silver and chromium, inorganic conductive materials such as copper iodide and copper sulfide, or conductive polymers such as polythiophene, polypyrrole and polyaniline. These electrode materials may be used singly or in plurality by lamination or mixture.

The resistance of the electrode is preferred to supply current sufficient for light emission of a light-emitting device, and low resistance is desirable from the viewpoint of power consumption of a light-emitting device. For example, an ITO substrate of 300 Ohm/Square or less functions as a device electrode, and the use of a low-resistance product of 100 Ohm/Square or less is particularly desirable for the reason that a substrate of approximately 10 Ohm/Square can presently be supplied. The thickness of ITO can optionally be selected in accordance with resistance values and is frequently used between typically 100 to 300 nm.

In order to retain mechanical strength of a light-emitting device, a light-emitting device is preferably formed on a substrate. Glass substrates such as soda glass and non-alkali glass are preferably used as the substrate. The thickness of the glass substrate is preferred to be sufficient for retaining mechanical strength, that is, 0.5 mm or more. With regard to materials for glass, non-alkali glass is preferable for the reason that less ion elution from glass is better, and soda-lime glass on which barrier coat such as SiO2 is applied is also commercially available and thereby can be used. In addition, if the anode functions stably, the substrate need not be glass; for example, the anode may be formed on a plastic substrate. A method of forming an ITO film is not particularly limited, such as an electron beam method, sputtering method and chemical reaction method.

Materials used for the cathode used in the present invention are not particularly limited if it is a substance capable of efficiently injecting an electron into the organic layer, and examples thereof generally including platinum, gold, silver, copper, iron, tin, zinc, aluminum, indium, chromium, lithium, sodium, potassium, cesium, calcium, magnesium, and alloys thereof. In order to improve device performance by increasing electron injection efficiency, lithium, sodium, potassium, cesium, calcium, magnesium or alloys containing these low work function metals are effective. However, generally, these low work function metals are frequently unstable in the atmosphere, and preferable examples include a method of using an electrode having high stability by doping the organic layer with a very small quantity of lithium and magnesium (1 nm or less at indication of a film thickness meter for vacuum deposition). An inorganic salt such as lithium fluoride can also be used. In addition, preferable examples for protection of an electrode include laminating of metals such as platinum, gold, silver, copper, iron, tin, aluminum and indium or alloys using these metals, inorganic matter such as silica, titania and silicon nitride, polyvinyl alcohol, vinyl chloride, and hydrocarbon polymeric compound. A method of producing these electrodes is not particularly limited if continuity can be secured, such as resistance heating, electron beam, sputtering, ion plating and coating.

With regard to a light-emitting device of the present invention, an organic layer is formed from a light-emitting device material containing a pyrene compound represented by the general formula (1). A light-emitting device material corresponds to either of an object which emits for itself and an object which assists light emission thereof, and signifies a compound involved in light emission, specifically corresponding to a hole transporting material, luminescent material and electron transporting material.

The organic layer composing a light-emitting device of the present invention is composed of at least a luminous layer comprising a light-emitting device material. Composition examples of the organic layer include a composition consisting of only the luminescent layer as well as laminated compositions such as 1) hole transporting layer/luminescent layer/electron transporting layer, 2) luminescent layer/electron transporting layer and 3) hole transporting layer/luminescent layer. Each of the above-mentioned layers may comprise a monolayer or a multilayer. In the case where the hole transporting layer and the electron transporting layer comprise a multilayer, layers thereof on the side contacting with an electrode are occasionally called a hole injecting layer and an electron injecting layer, respectively, and a hole injecting material and an electron injecting material are included in a hole transporting material and an electron transporting material, respectively in the following description.

The hole transporting layer is formed by laminating and mixing one kind or two kinds or more of a hole transporting material, or a mixture of a hole transporting material and a polymeric binding agent. Preferable examples of the hole transporting material include triphenylamine derivatives such as 4,4'-bis(N-(3-methylphenyl)-N-phenylamino)biphenyl, 4,4'-bis(N-(1-naphthyl)-N-phenylamino)biphenyl and 4,4', 4"-tris(3-methylphenyl(phenyl)amino)triphenylamine, bis-carbazole derivatives such as bis(N-allylcarbazole) or bis(N-alkylcarbazole), heterocyclic compounds such as a pyrazoline derivative, stilbene-based compound, hydrazone-based compound, benzofuran derivative, thiophene derivative, oxadiazole derivative, phthalocyanine derivative and porphyrin derivative, and polymers with a side chain of above-mentioned monomers, such as polycarbonate, styrene derivative, polythiophene, polyaniline, polyfluorene, polyvinyl carbazole and polysilane; which hole transporting material is not particularly limited if it is a compound capable of forming a thin film necessary for producing a light-emitting device injecting a hole from an anode and additionally transporting the hole.

In the present invention, the luminescent layer may comprise either of a monolayer and a multilayer, each of which is formed from a luminescent material (a host material and a dopant material), and this luminescent material may be either of a mixture of a host material and a dopant material and a host material singly. That is, with regard to a light-emitting device of the present invention, in each of the luminescent layers, only one of a host material and a dopant material may emit light, or both of a host material and a dopant material may emit light. Each of a host material and a dopant material may be of either one kind or a combination of plural kinds. A dopant material may be contained in a host material either entirely or partially. A dopant material may be either laminated or dispersed. The amount of a dopant material is preferably used at 0.1% by weight or more and 20% by weight or less, more preferably 0.5% by weight or more and 10% by weight or less, with respect to a host material for the reason that too large quantity thereof occasionally causes a concentration quenching phenomenon. With regard to a doping method, code position of a dopant material and a host material can be formed by a code position method, and deposition may simultaneously be performed after previously mixing a dopant material and a host material.

A pyrene compound represented by the general formula (1) of the present invention is preferably used as a luminescent material. A pyrene compound of the present invention is preferably used as a blue luminescent material by reason of offering intense light emission in blue color region, and is not limited thereto but can also be used as a material for a green to red light-emitting device and a white light-emitting device. A pyrene compound of the present invention may be used as a host material and preferably as a dopant material by reason of high fluorescent quantum efficiency and small spectral half-value width.

Ionization potential of a pyrene compound represented by the general formula (1) of the present invention is not particularly limited, being preferably 5 or higher to 7 eV or lower, more preferably 5.4 or higher 6.4 eV or lower. The absolute value of ionization potential reportedly varies with a measuring method, and ionization potential of the present invention is a value obtained by measuring a thin film deposited to a thickness of 30 to 100 nm on an ITO glass substrate with the use of an atmosphere type ultraviolet light electronic analysis instrument (AC-1, manufactured by RIKEN KIKI CO., LTD.).

The dopant material used in the present invention need not be limited to only one kind of the above-mentioned pyrene compound, and plural pyrene compounds may be used therefor by mixture, or one kind or more of known dopant materials may be used therefor by mixture with the pyrene compound. Specific examples thereof include, conventionally known, compounds having an aryl ring and derivatives thereof, such as naphthalene, anthracene, phenanthrene, pyrene, triphenylene, perylene, fluorene and indene, compounds having a heteroaryl ring and derivatives thereof, such as furan, pyrrole, thiophene, silole, 9-silafluorene, 9,9'-spiro-bisilafluorene, benzothiophene, benzofuran, indole, dibenzothiophene, dibenzofuran, imidazopyridine, phenanthroline, pyrazine, naphthyridine, quinoxaline, pyrrolopyridine and thioxanthene, a distyrylbenzene derivative, aminostyryl derivative, aromatic acetylene derivative, tetraphenyl butadiene derivative, stilbene derivative, aldazine derivative, coumarin derivative, azole derivatives and metal complexes thereof, such as imidazole, thiazole, thiadiazole, carbazole, oxazole, oxadiazole and triazole, and an aromatic amine derivative typified by 4,4'-bis(N-(3-methylphenyl)-N-phenylamino)biphenyl; which examples are not limited thereto.

The host material contained in a luminescent material is not particularly limited, and the following are preferably used: compounds having a condensed aryl ring and derivatives thereof, such as anthracene and pyrene known as a luminophor since before, an aromatic amine derivative such as 4,4'-bis(N-(1-naphtyl)-N-phenylamino)biphenyl, a metal chelated oxynoid compound including tris(8-quinolinolate) aluminum (III), a bisstyryl derivative such as a distyrylbenzene derivative, a tetraphenyl butadiene derivative, indene derivative, coumarin derivative, oxadiazole derivative, pyrrolopyridine derivative, perynone derivative, cyclopentadiene derivative, oxadiazole derivative, carbazole derivative, and pyrrolopyrrole derivative. Also, the following are preferably used as polymers: a polyphenylene vinylene derivative, polyparaphenylene derivative, polyfluorene derivative, polyvinyl carbazole derivative and polythiophene derivative. Above all, the use of an anthracene compound having an electron donative substituent as a host material brings a notable effect of improving durability in combining with a pyrene compound of the present invention, and therefore is preferable.

An anthracene compound as described above is not particularly limited; specific examples thereof include the following.

[C31]

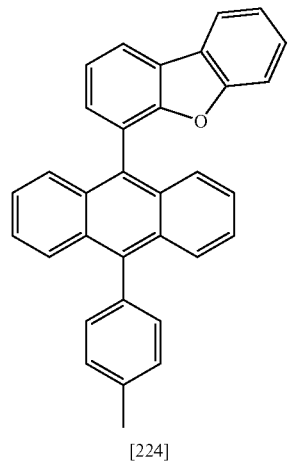

[224]

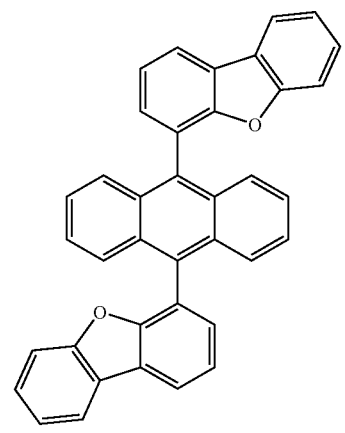

[225]

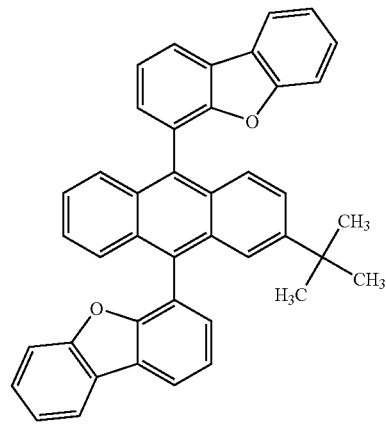

[226]

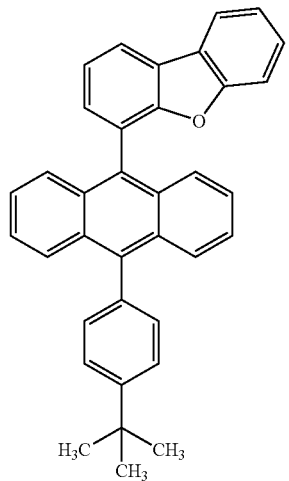
[227]
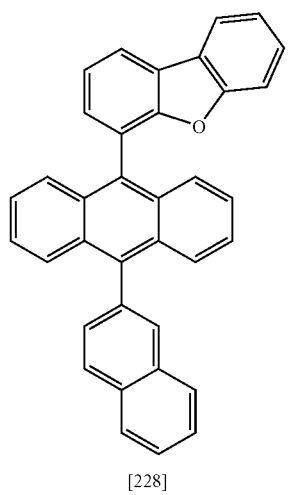
[228]
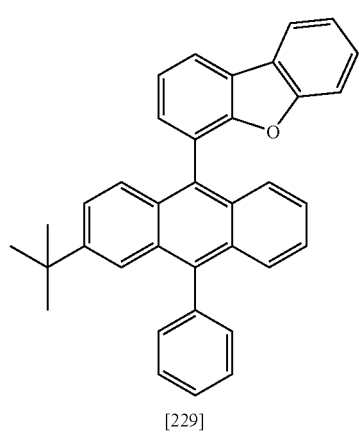
[229]
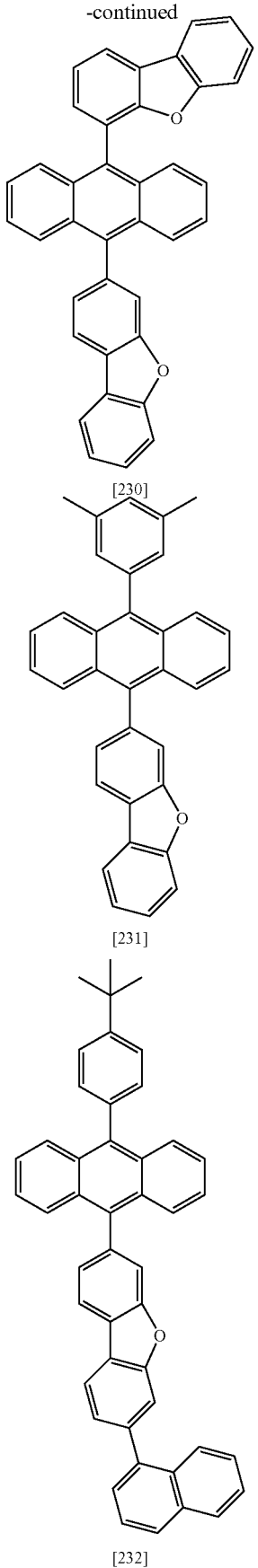
[230]
[231]
[232]

87
-continued
[C32]
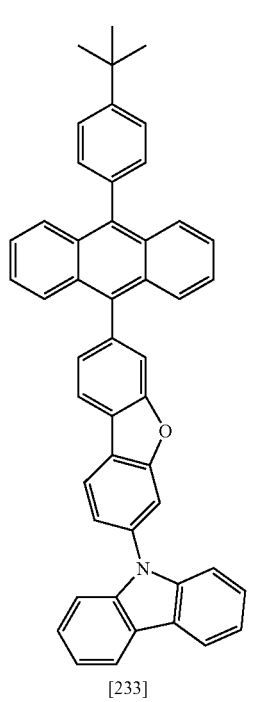
[233]
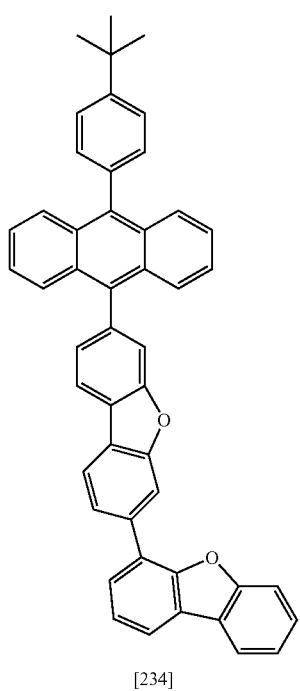
[234]
88
-continued
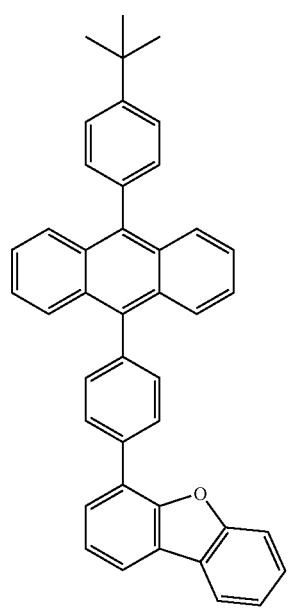
[235]
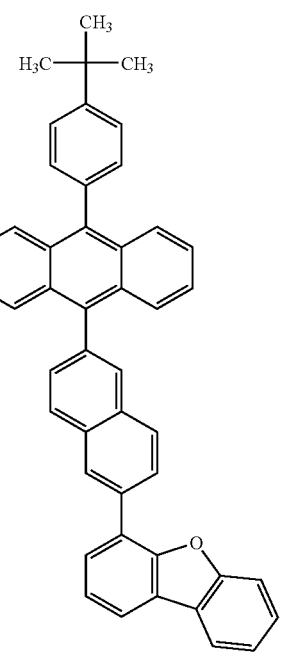
[236]

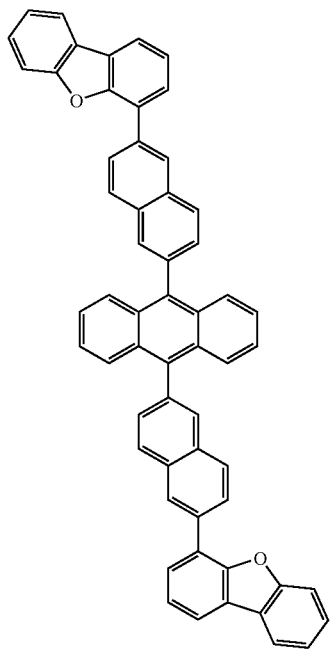
[237]
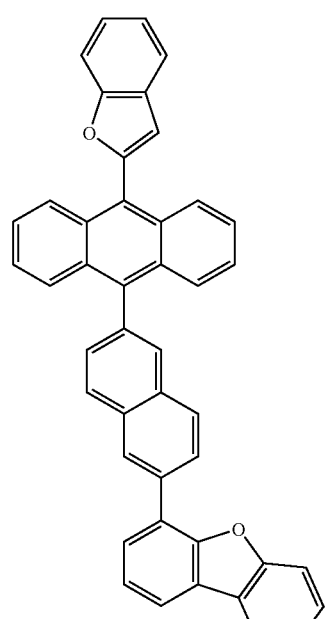
[238]
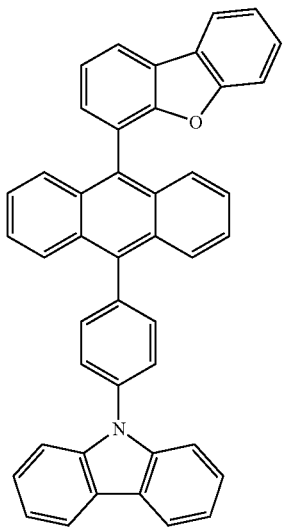
[239]
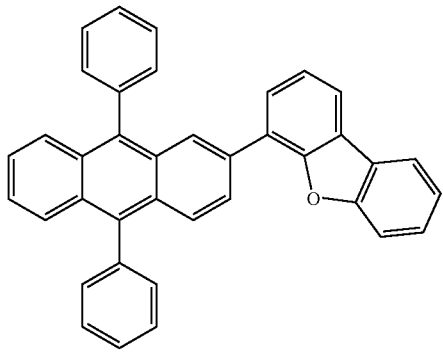
[240]
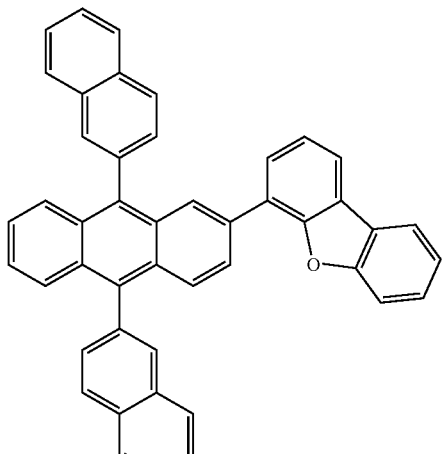
[241]

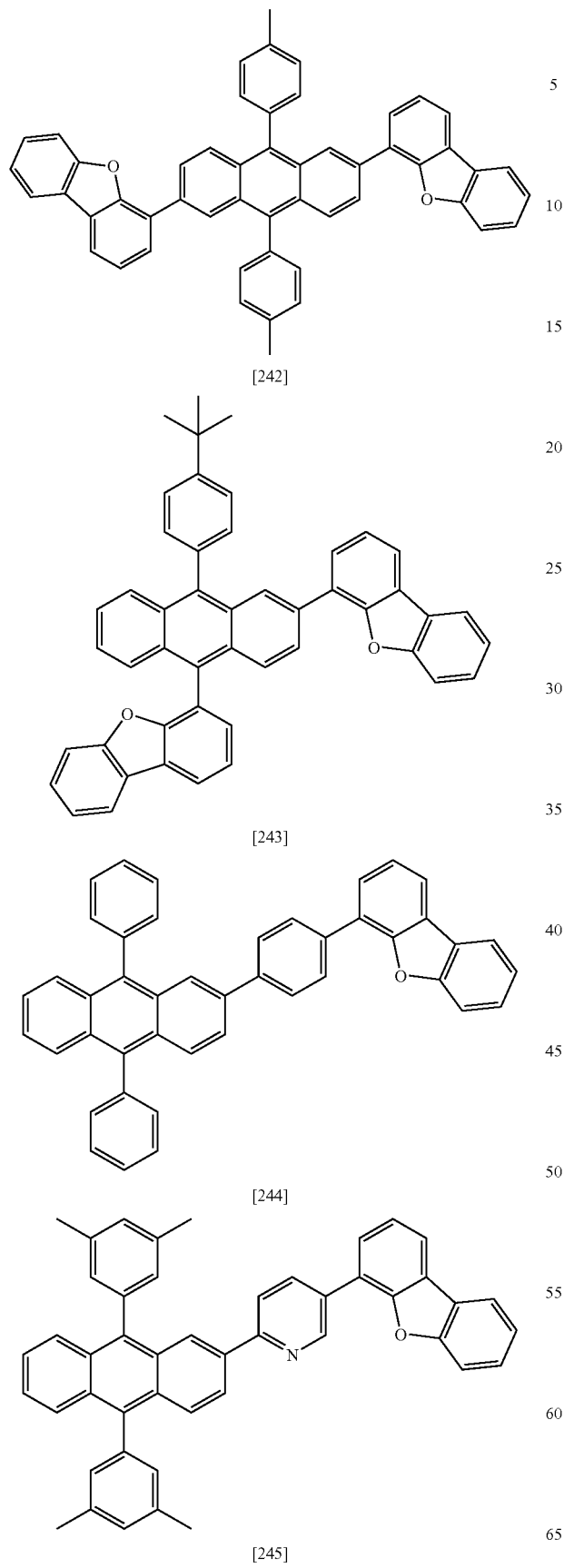
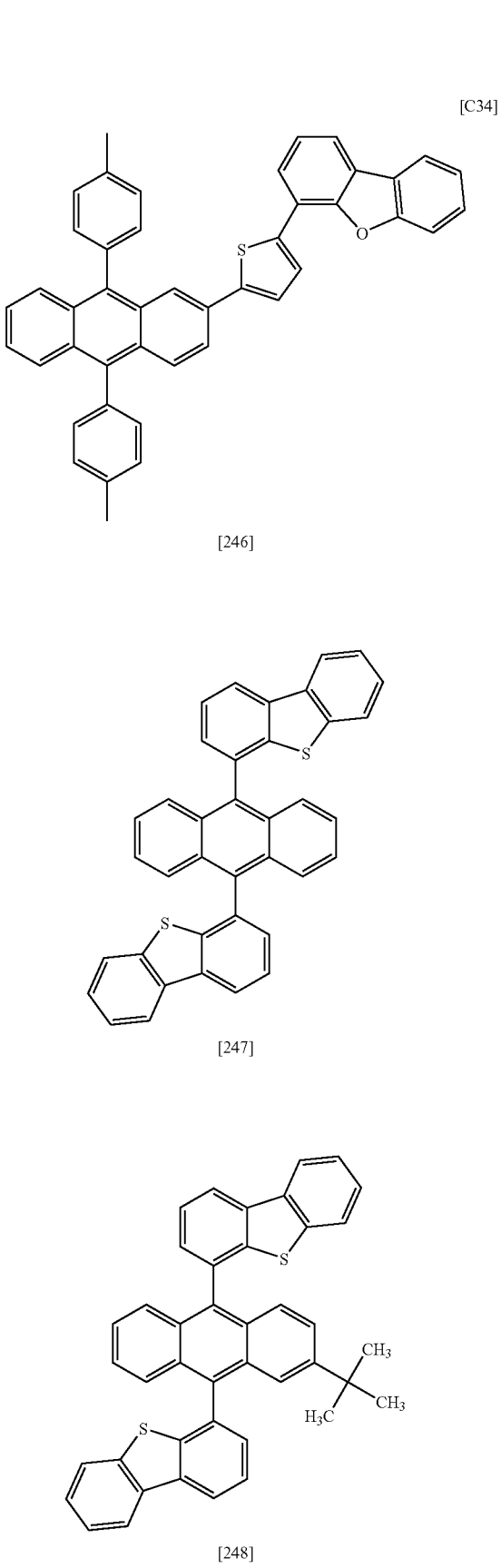

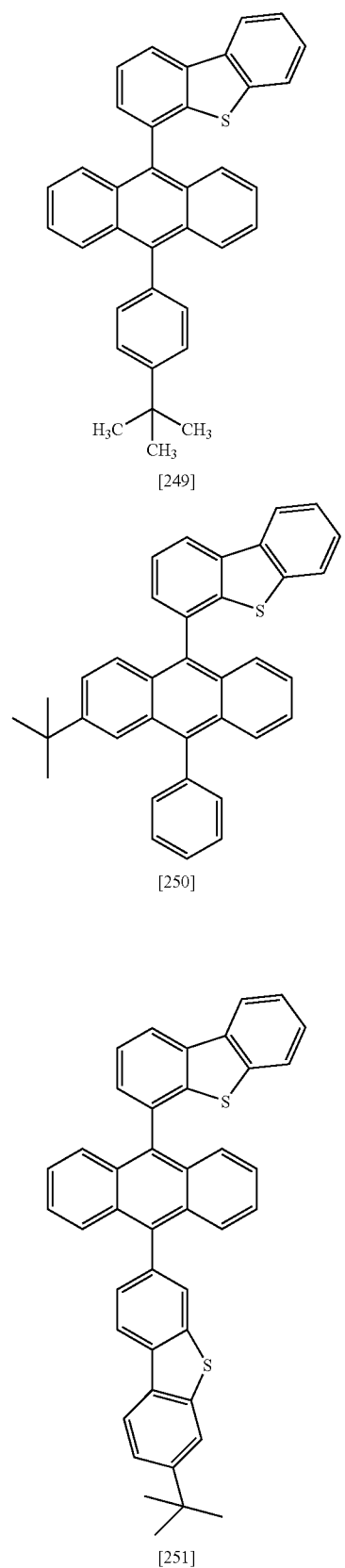
[249]
[250]
[251]
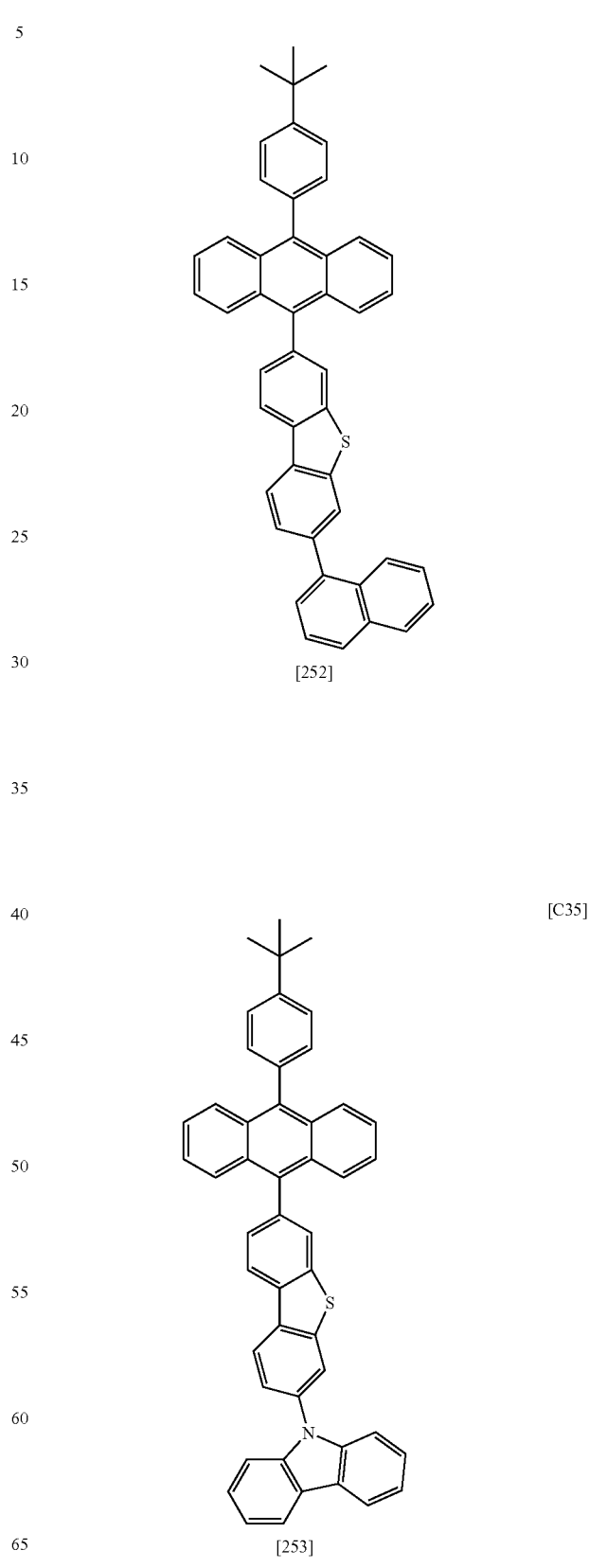
[252]
[253]

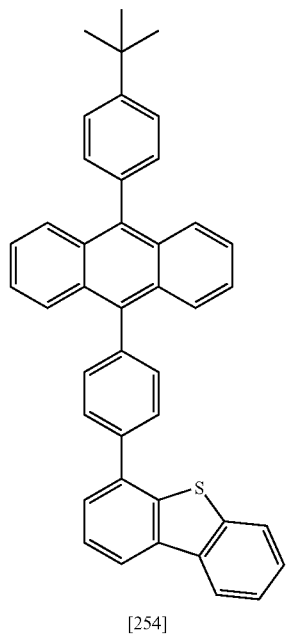
[254]
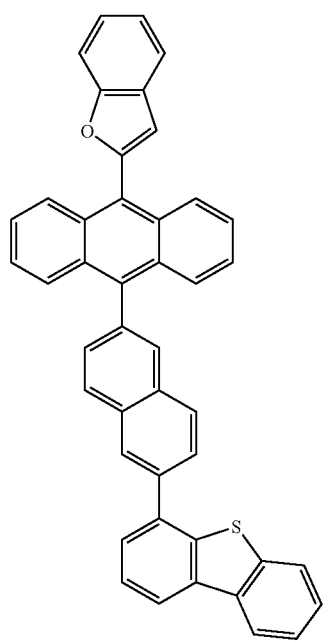
[255]
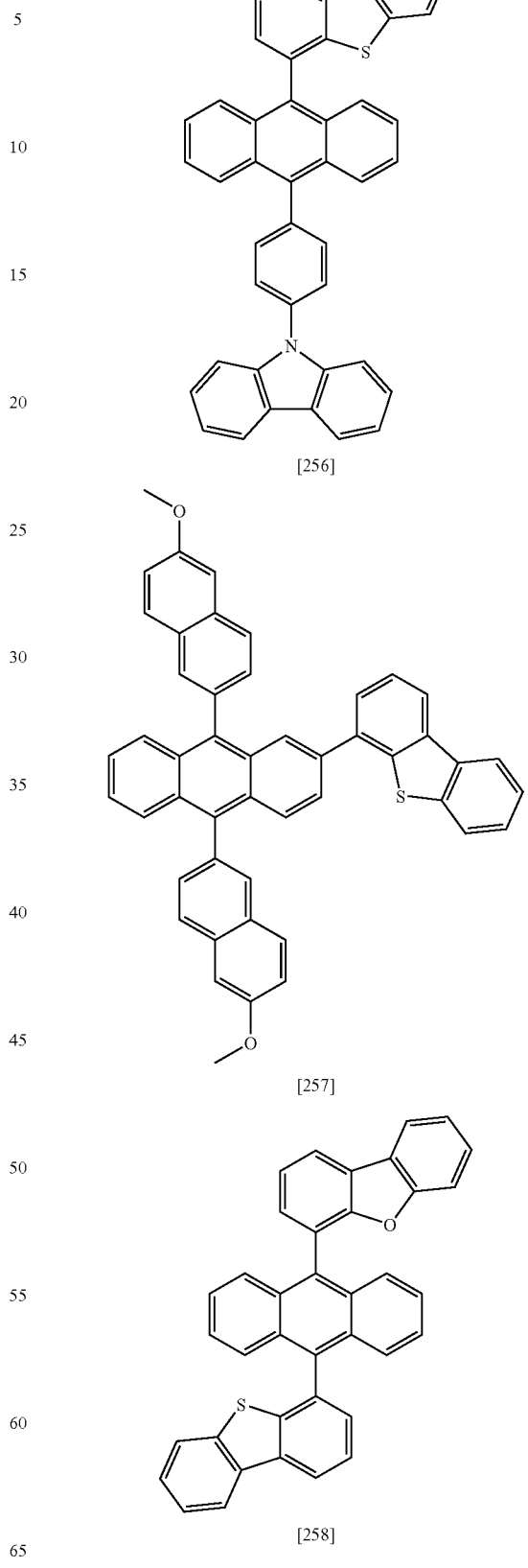
[256]
[257]
[258]

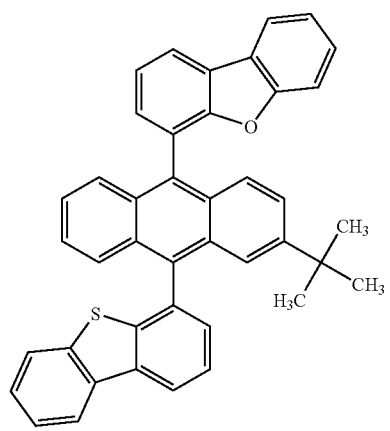
[259]
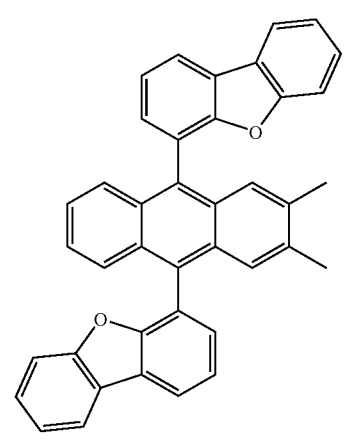
[260]
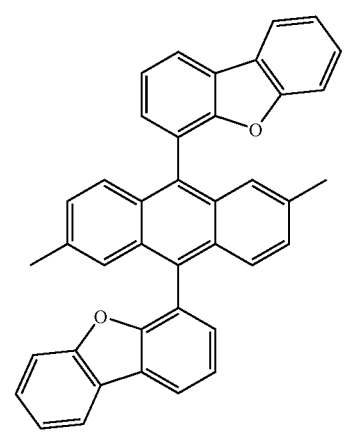
[261]
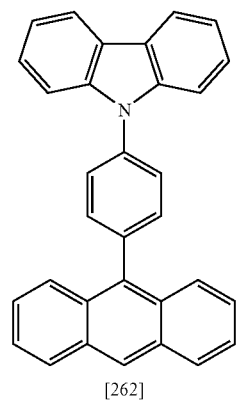
[262]
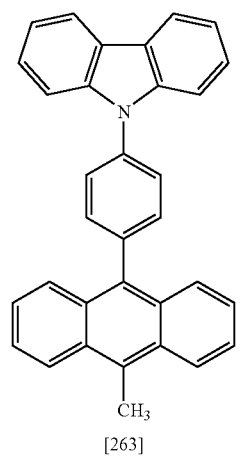
[263]
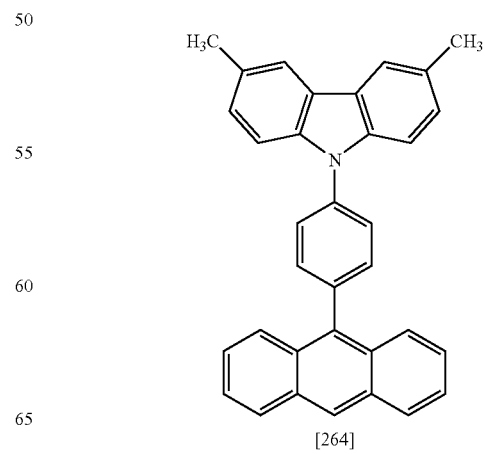
[264]

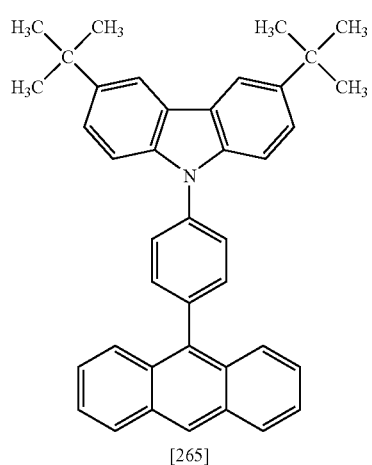
[265]
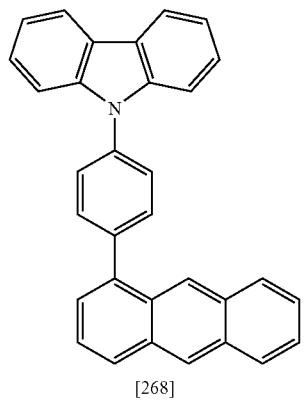
[268]
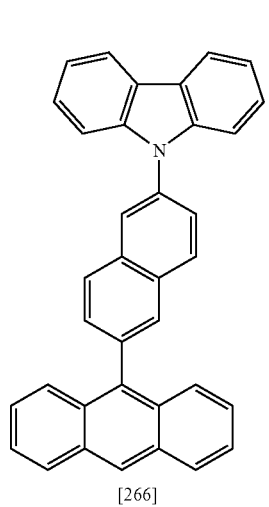
[266]
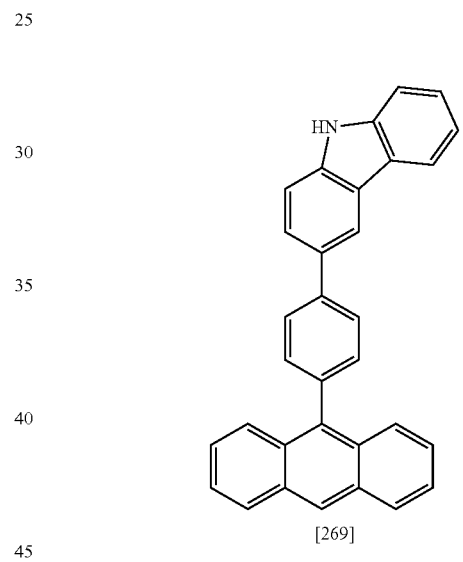
[269]
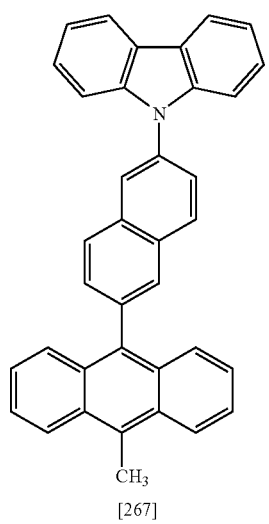
[267]
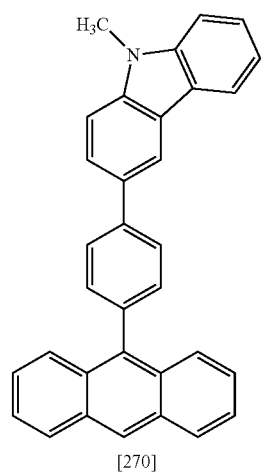
[270]

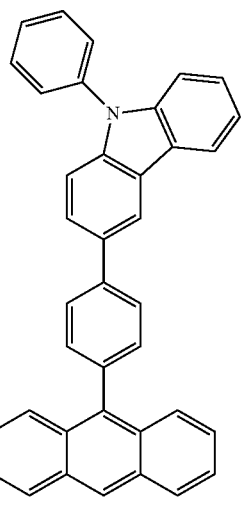
[271]
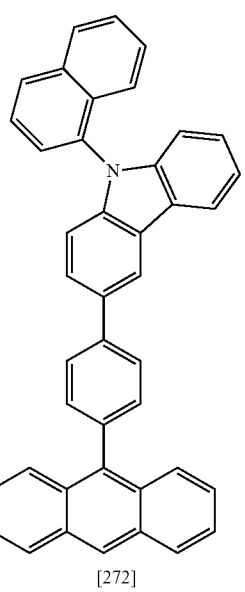
[272]
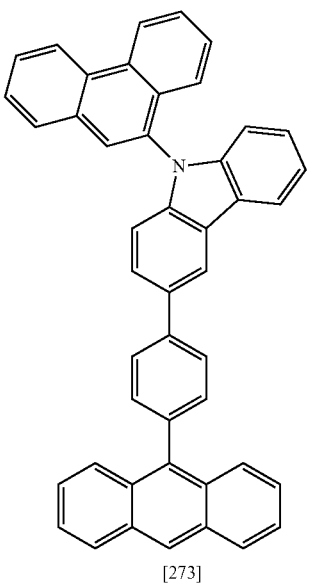
[273]
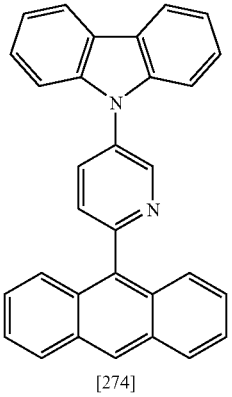
[274]
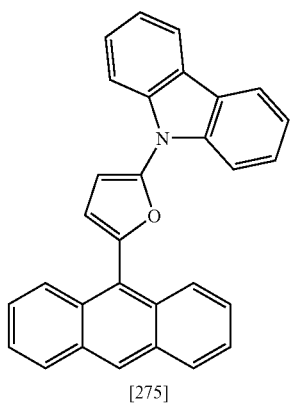
[275]
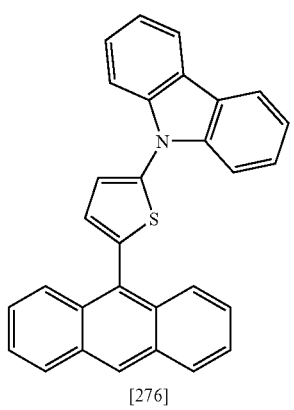
[276]
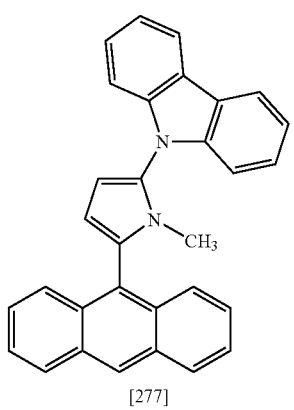
[277]

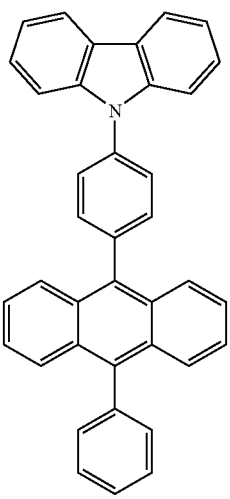
[278]
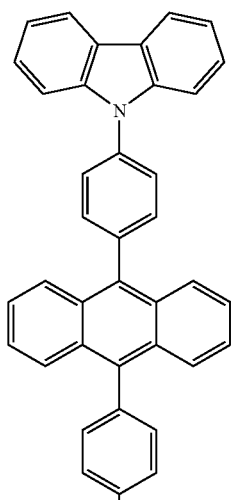
[279]
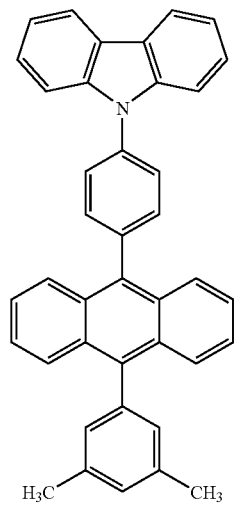
[280]
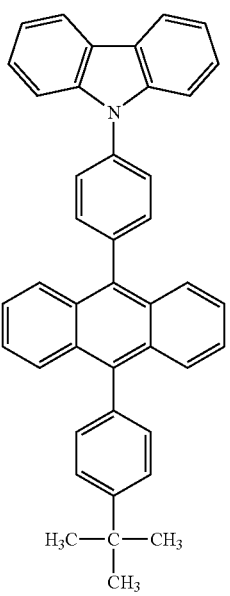
[281]
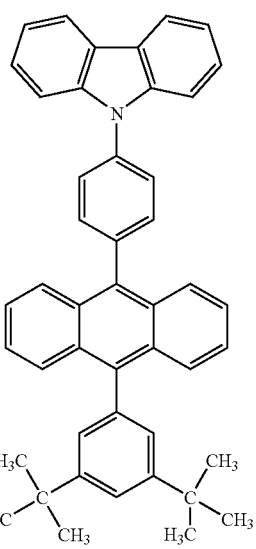
[282]

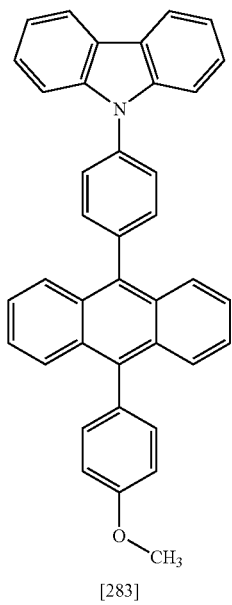
[283]
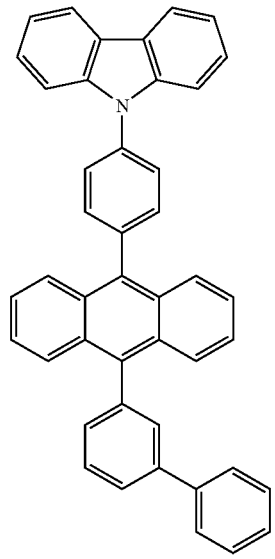
[285]
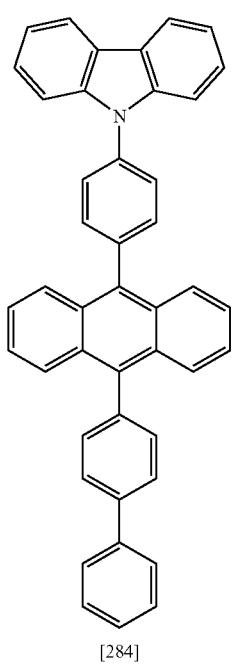
[284]
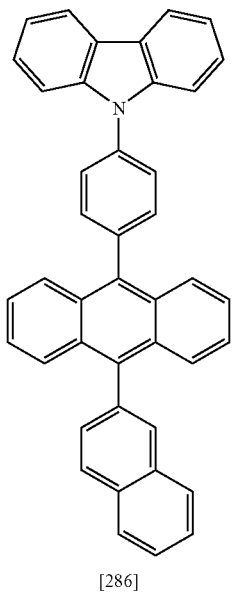
[286]

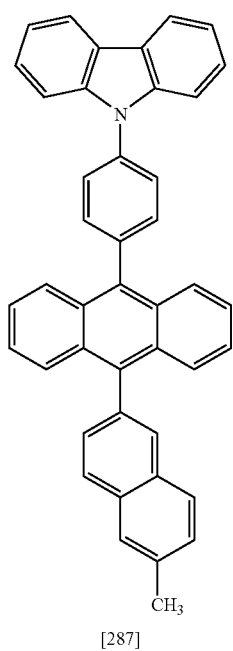
[287]
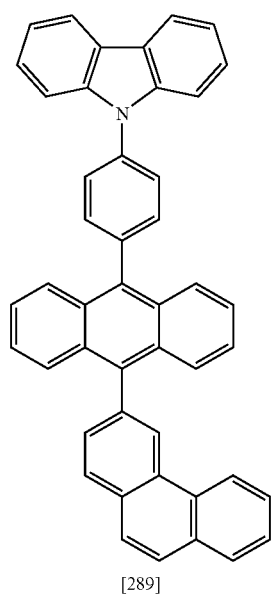
[289]
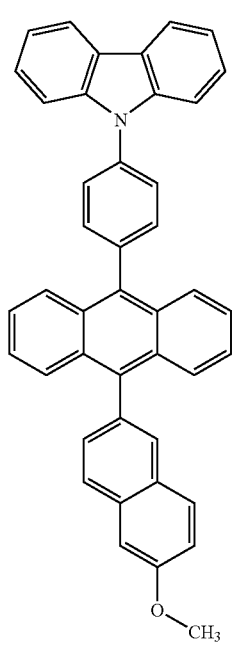
[288]
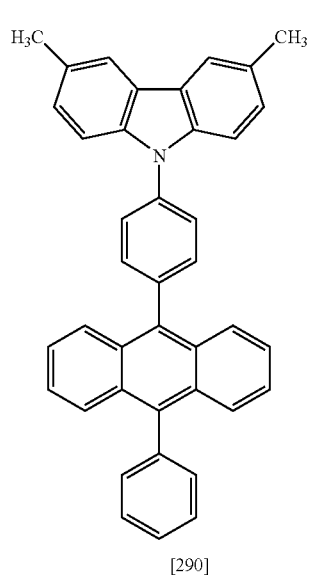
[C38]
[290]

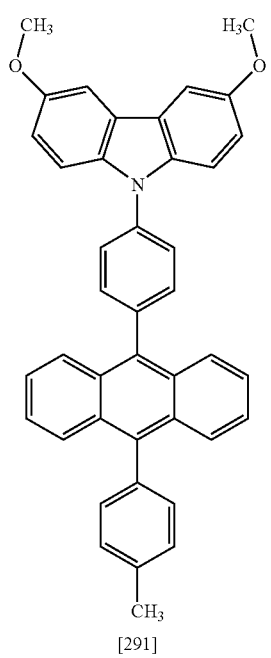
[291]
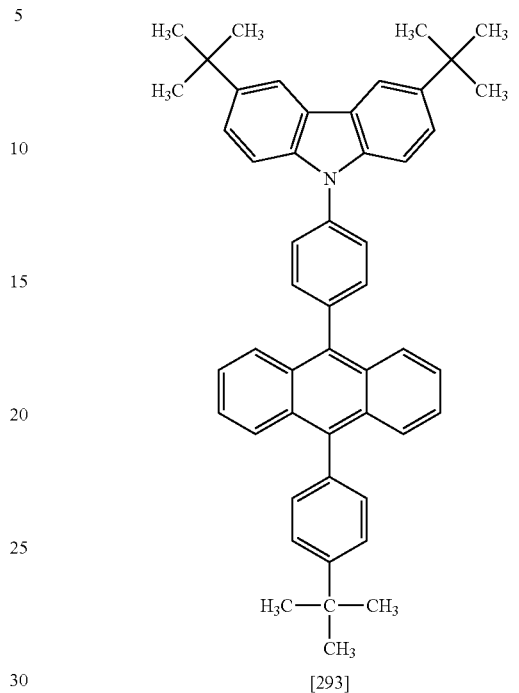
[293]
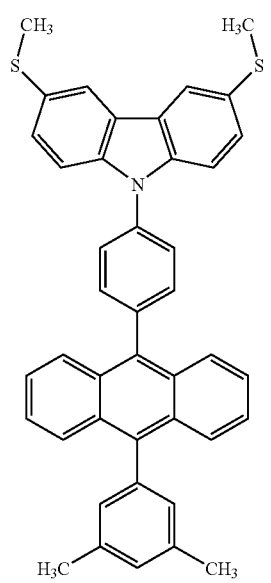
[292]
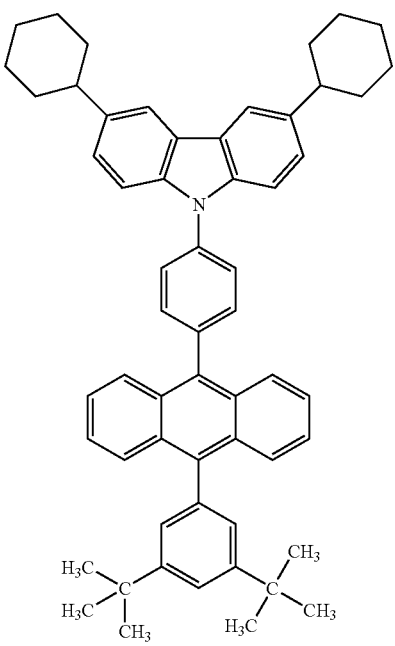
[294]

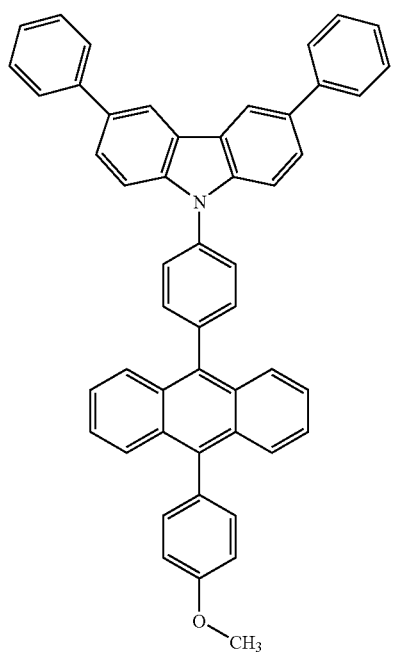
[295]
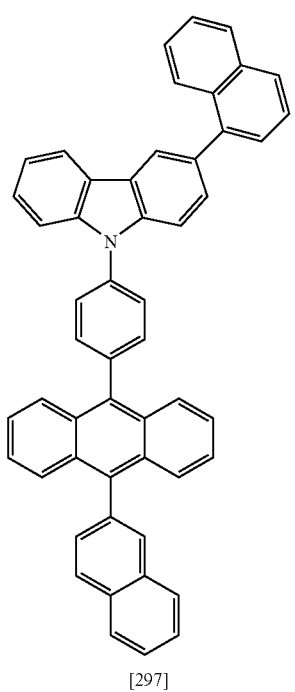
[297]
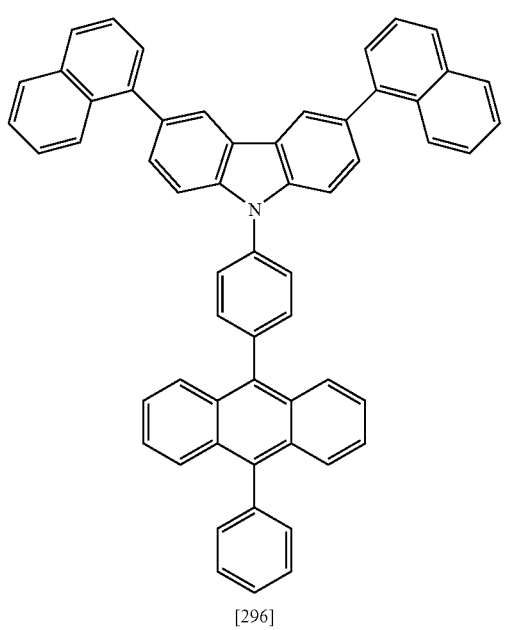
[296]
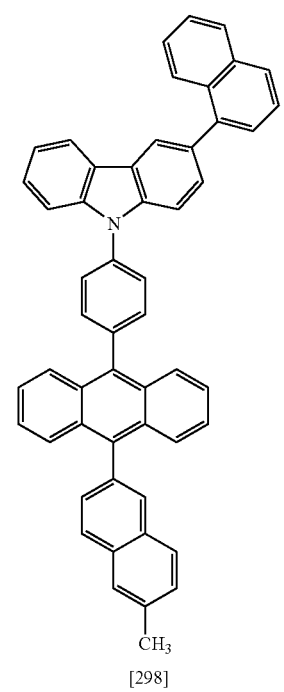
[298]

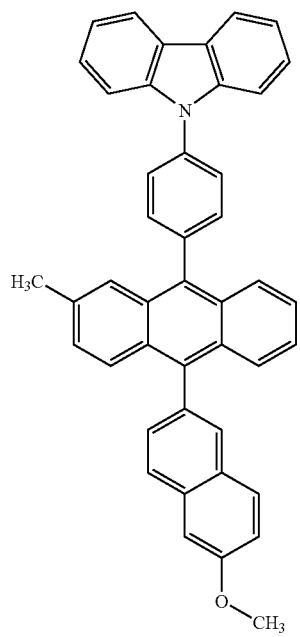
[299]
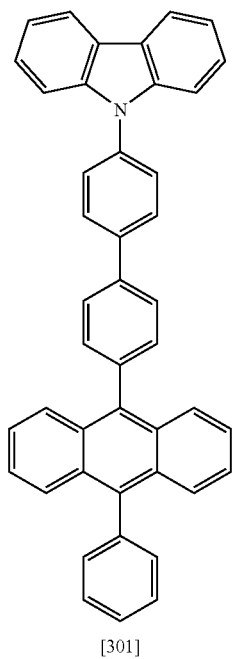
[301]
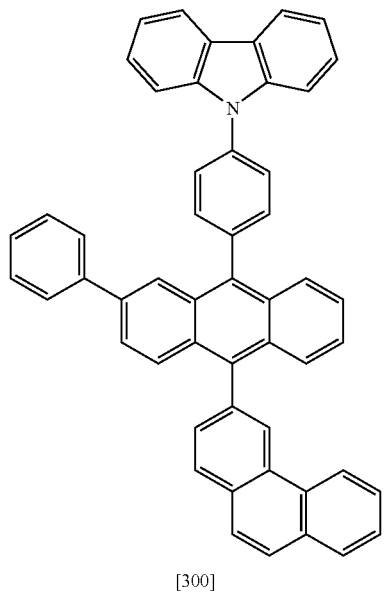
[300]
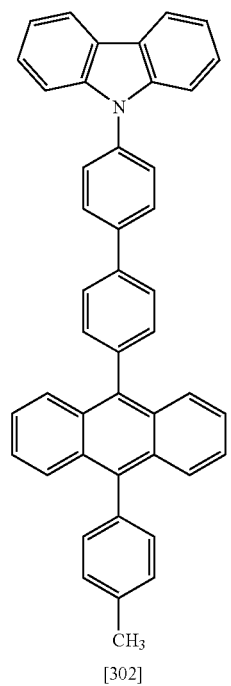
[302]

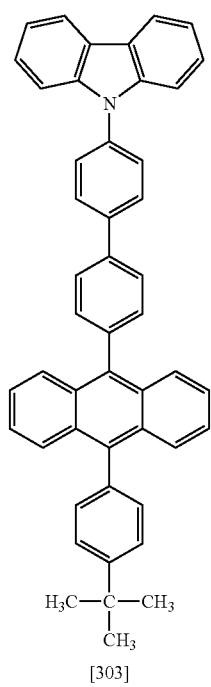
[303]
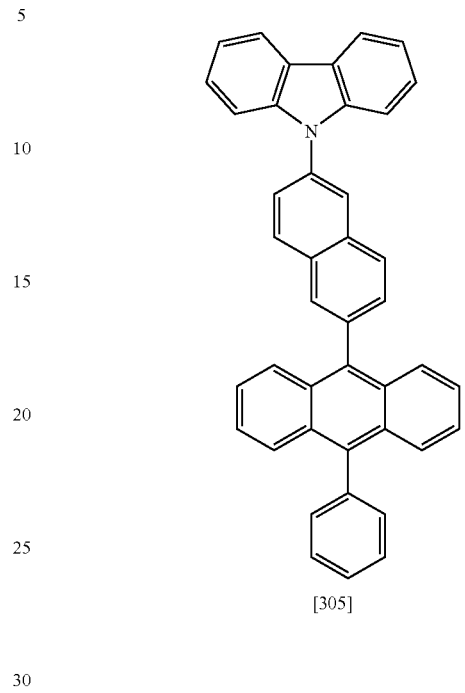
[305]
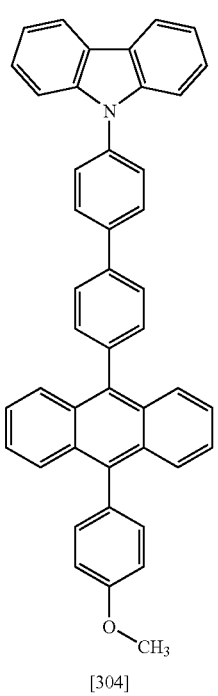
[304]
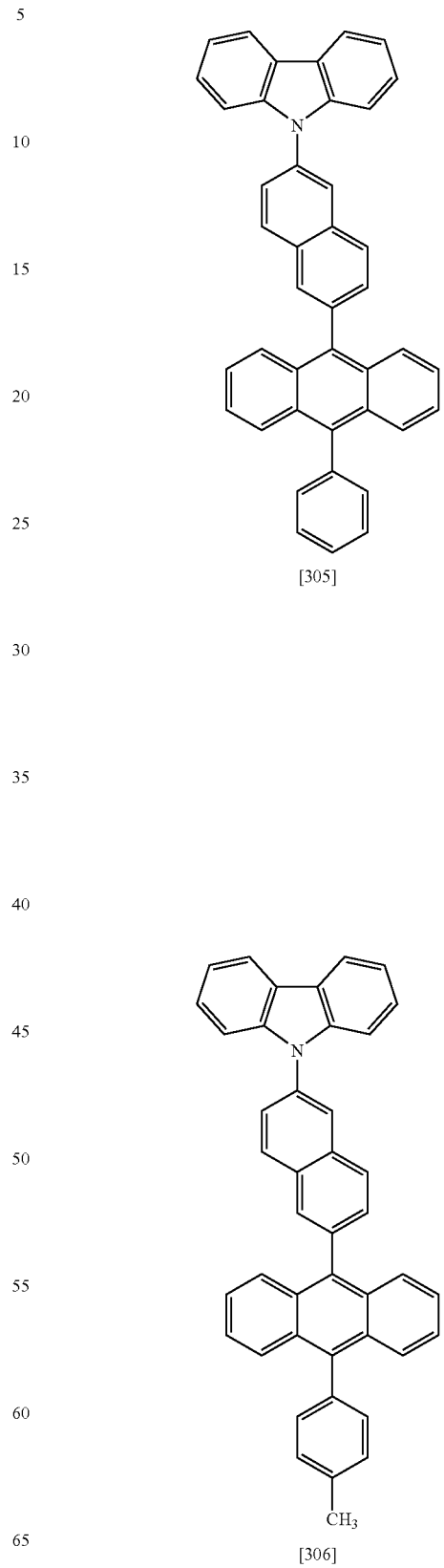
[306]

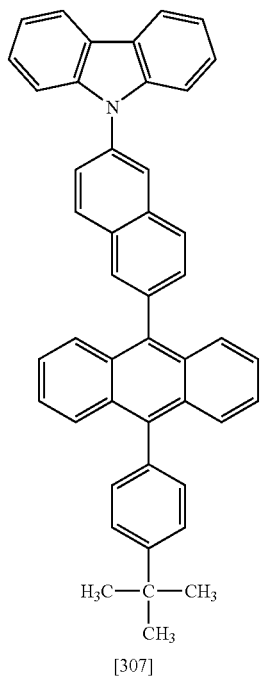
[307]
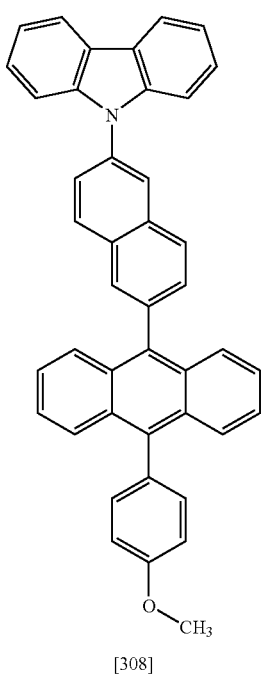
[308]
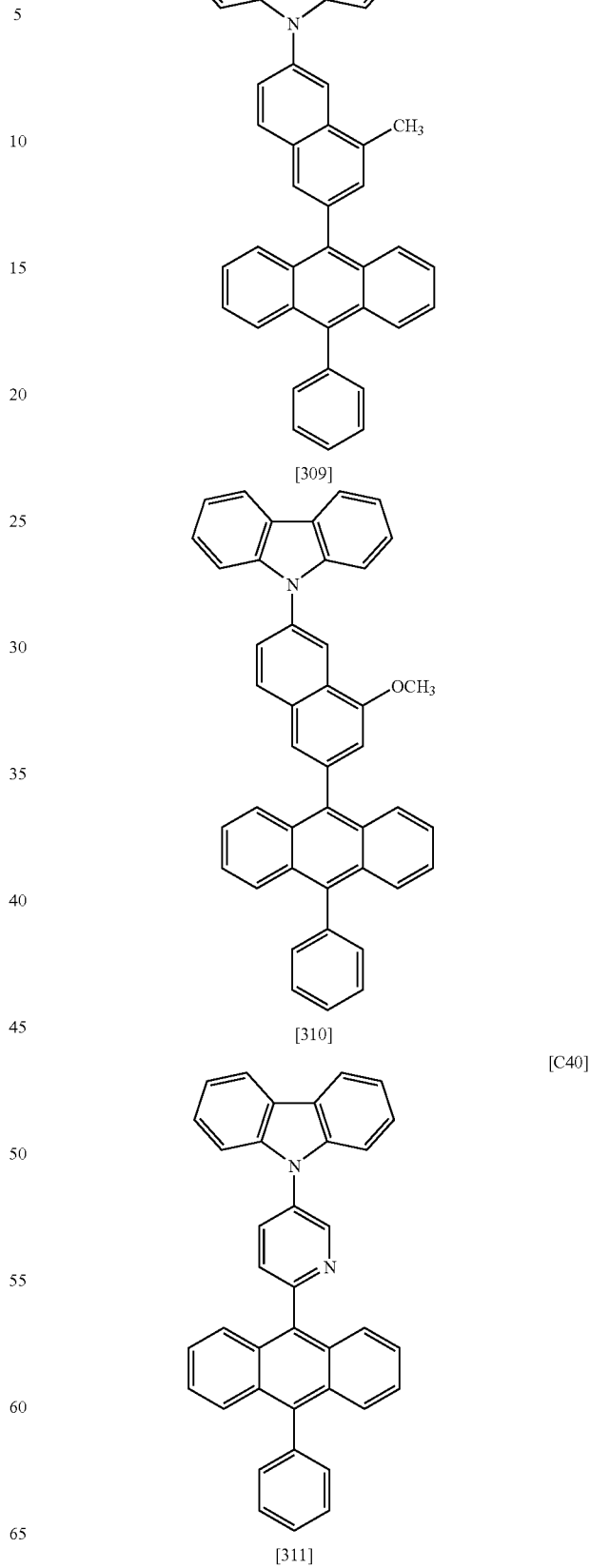

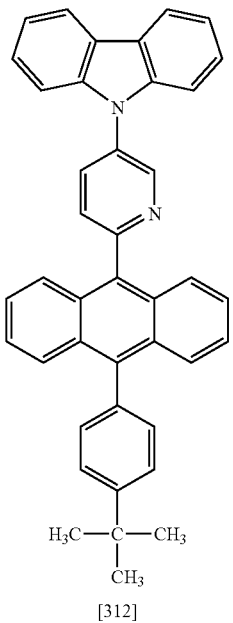
[312]
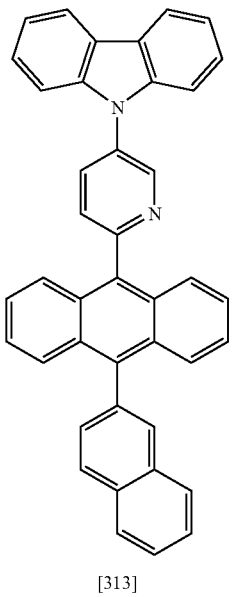
[313]
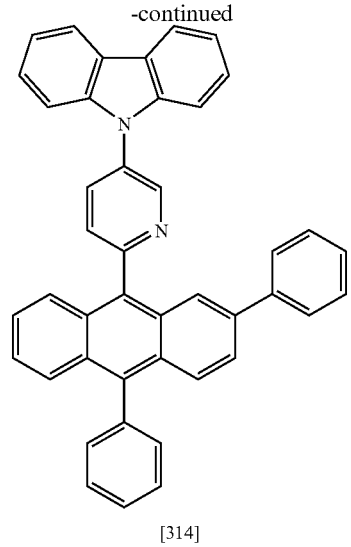
[314]
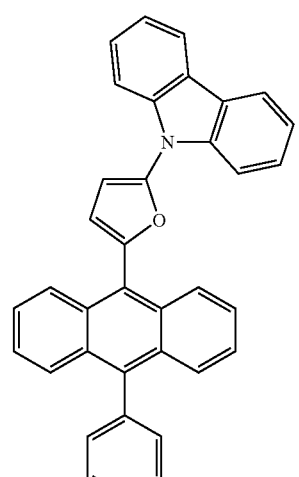
[315]
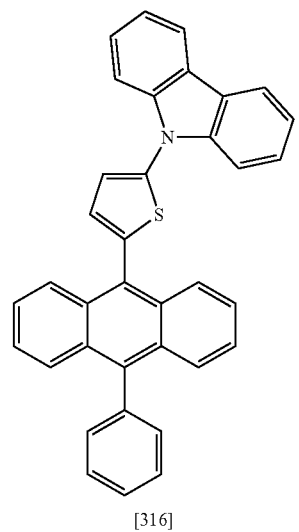
[316]

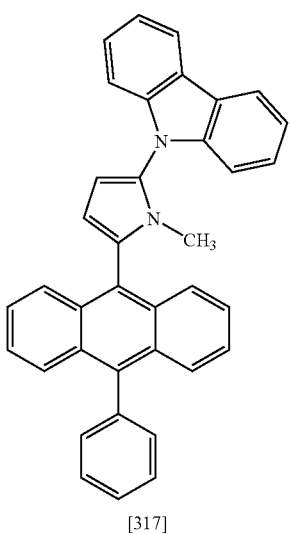
[317]
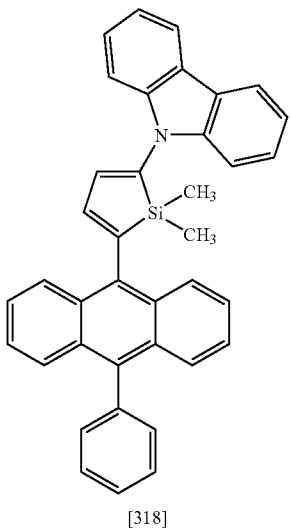
[318]
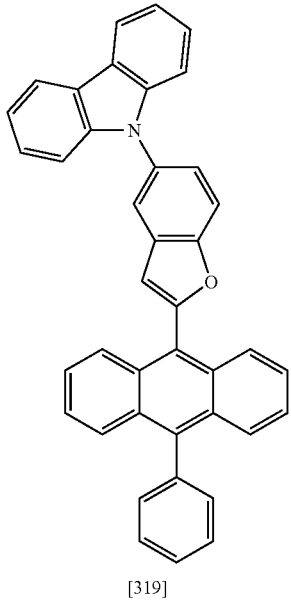
[319]
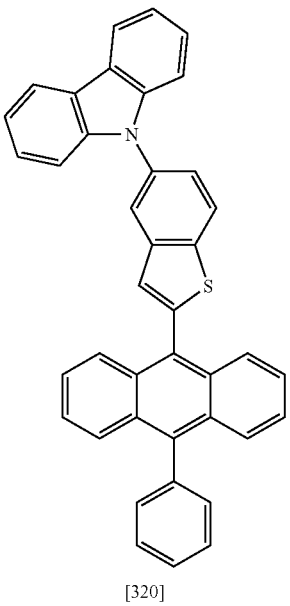
[320]
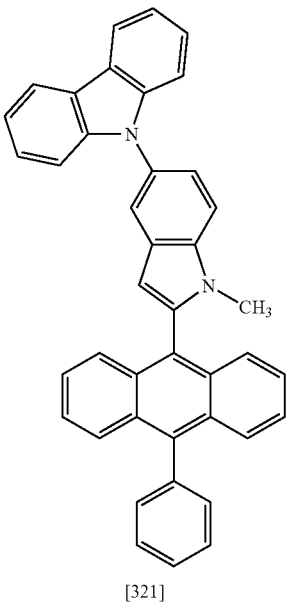
[321]

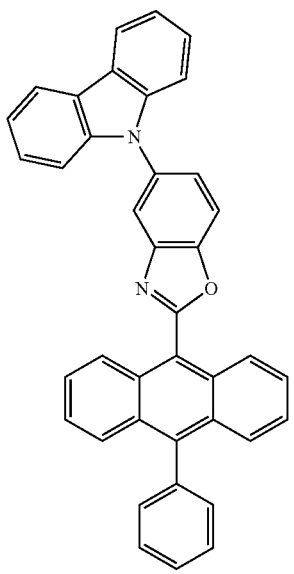
[322]
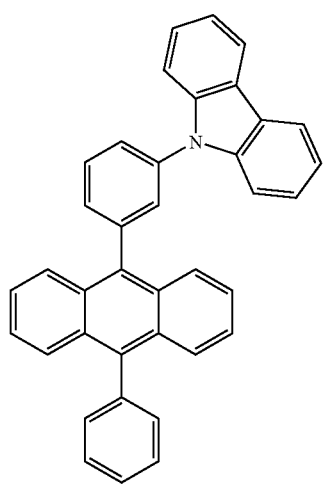
[323]
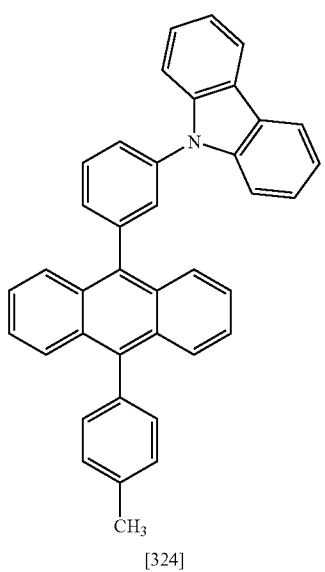
[324]
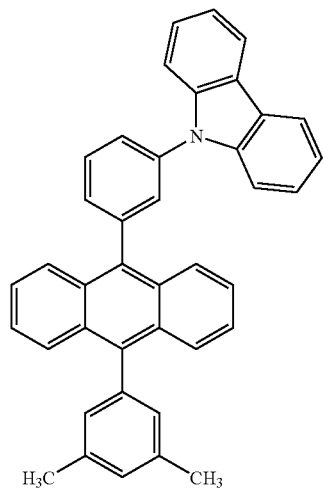
[325]
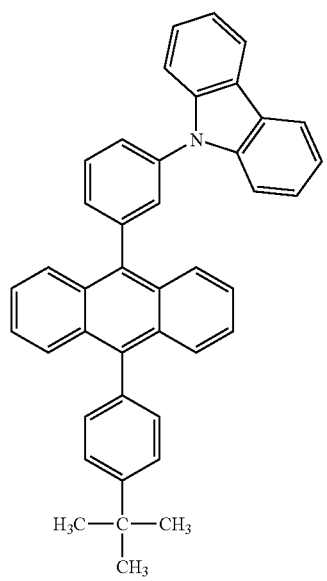
[326]
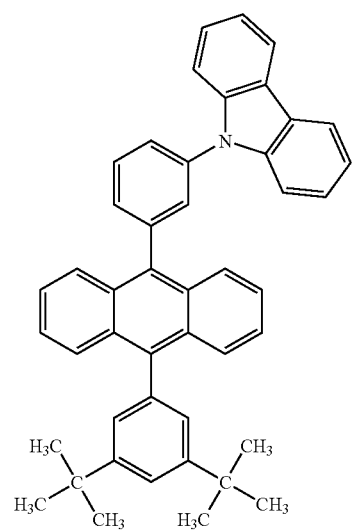
[327]

125
-continued
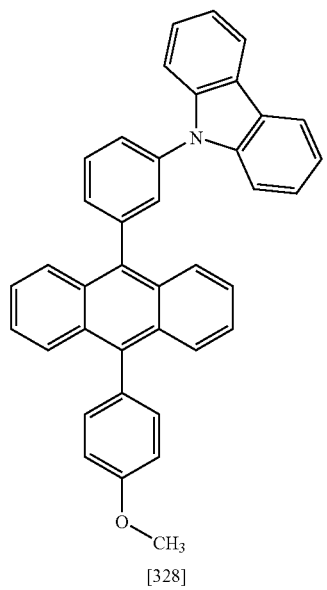
[328]
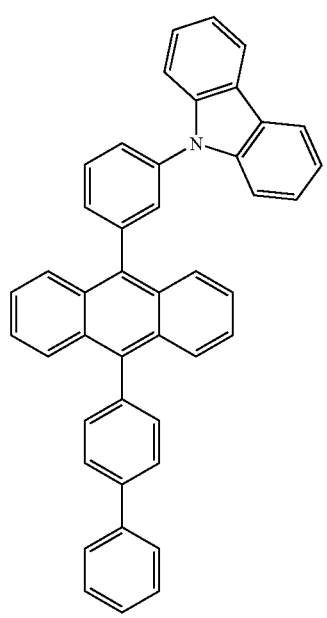
[329]
126
-continued
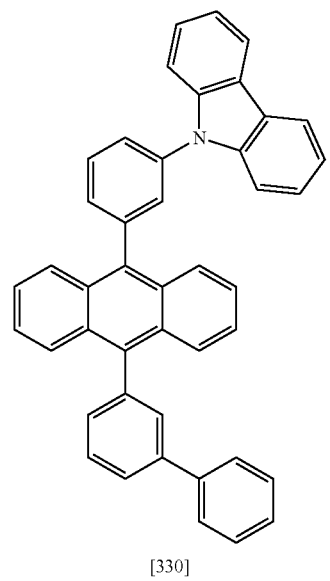
[330]
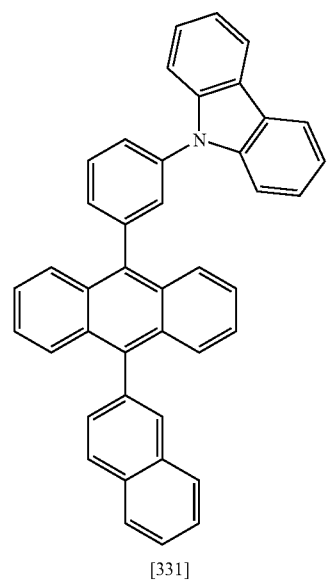
[331]

127
-continued
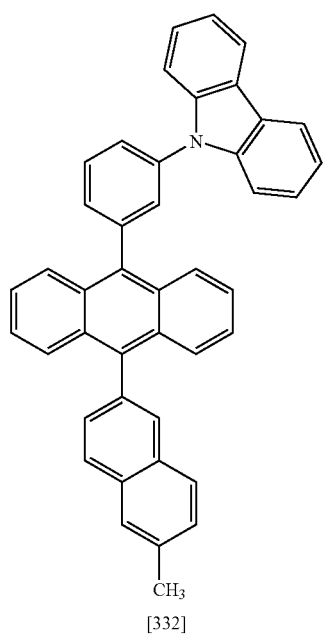
[332]
128
-continued
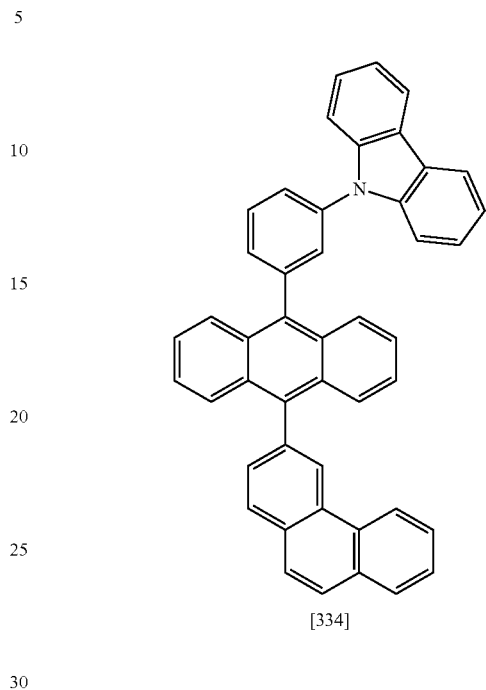
[334]
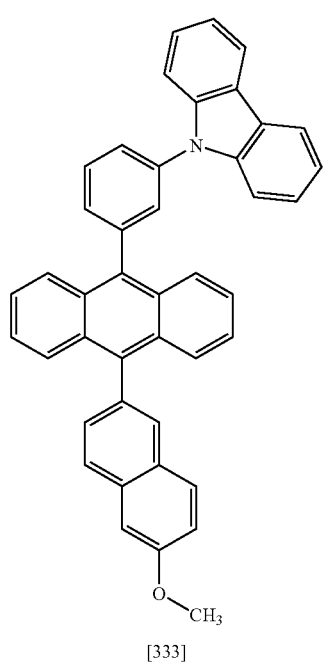
[333]
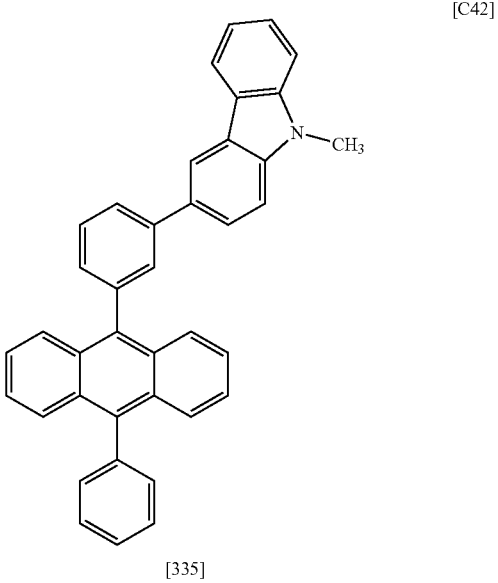
[C42]
[335]

-continued
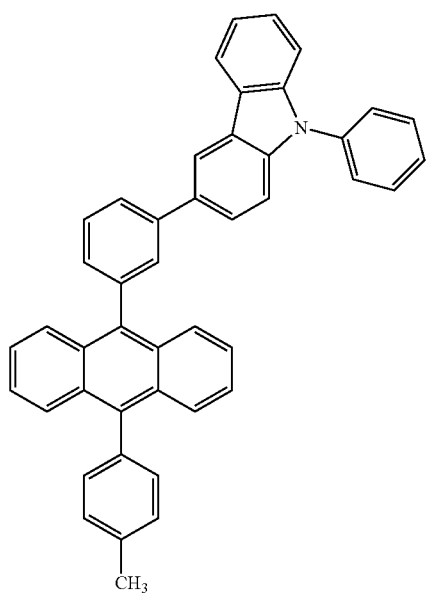
[336]
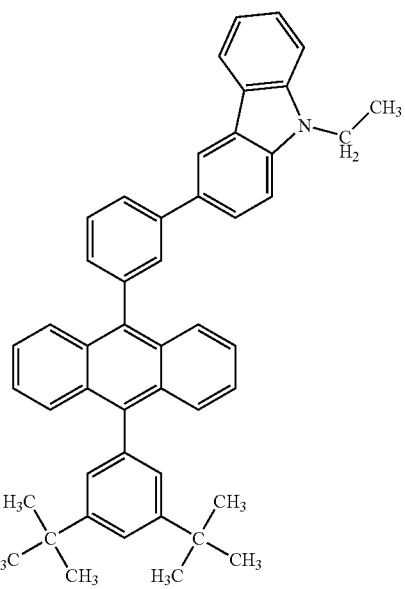
[338]
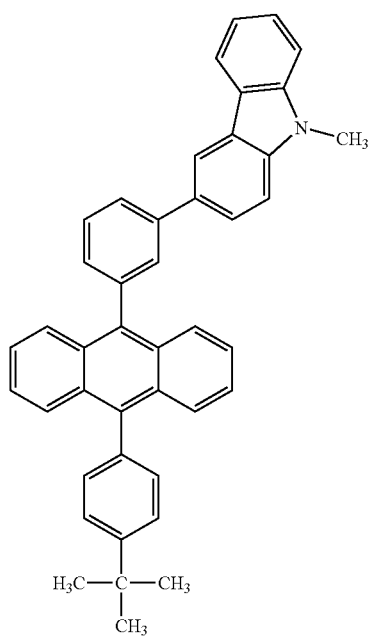
[337]
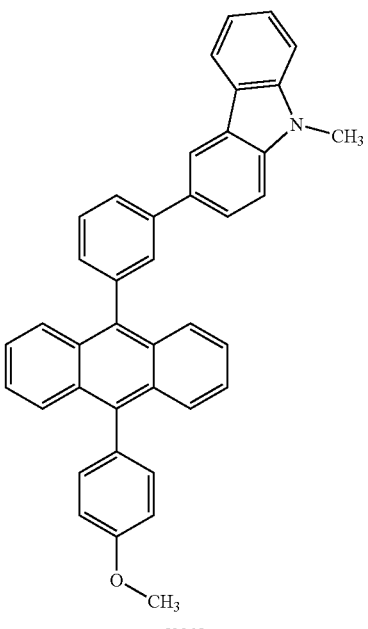
[339]

-continued
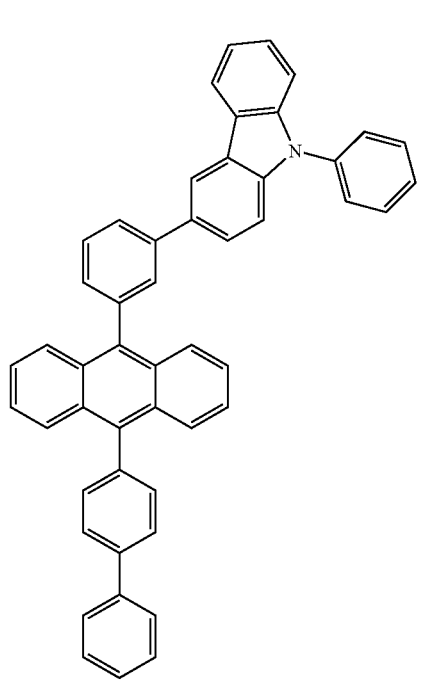
[340]
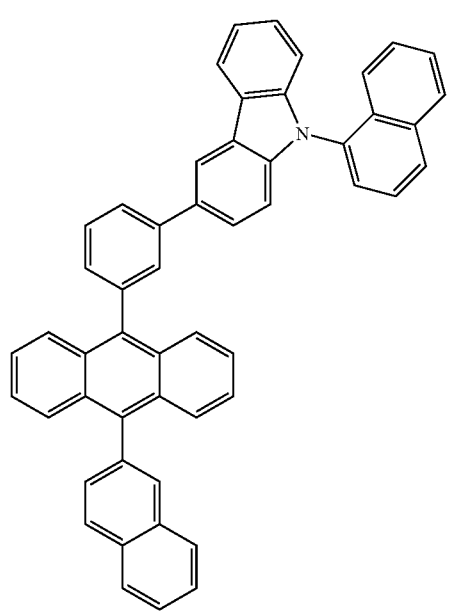
[341]
-continued
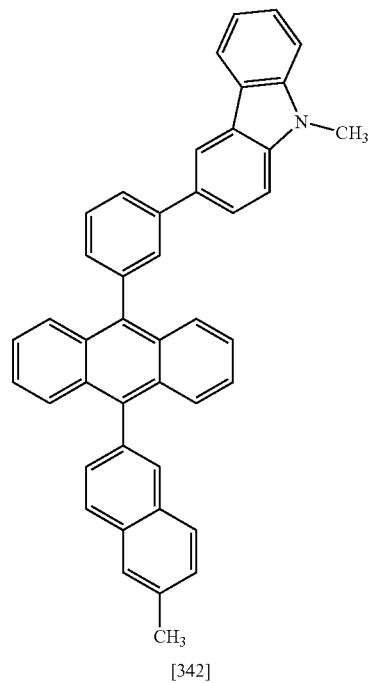
[342]
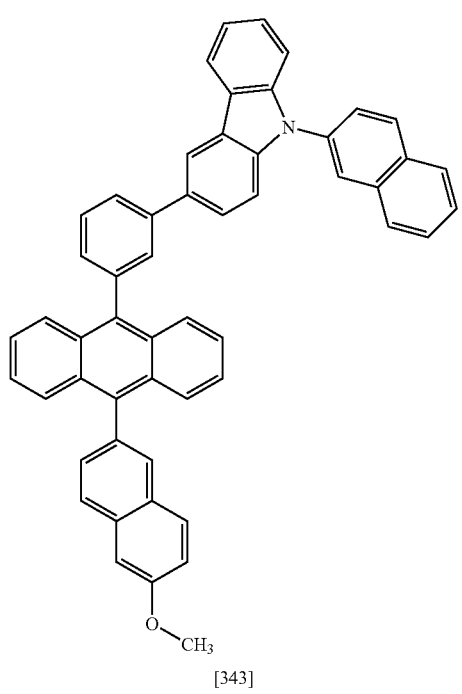
[343]

[C43]
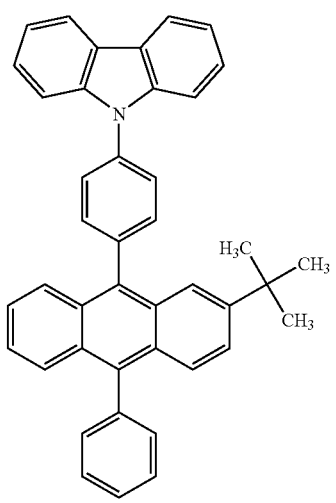
[344]
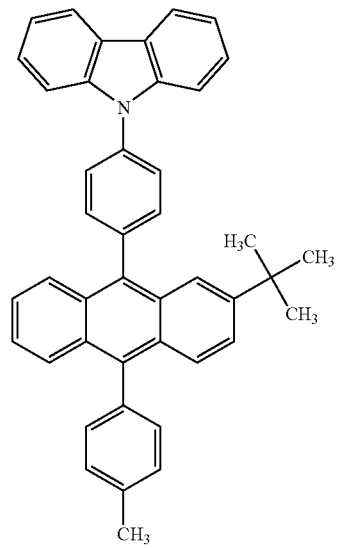
[345]
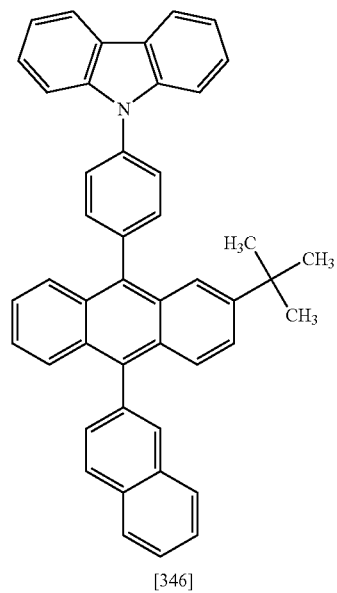
[346]
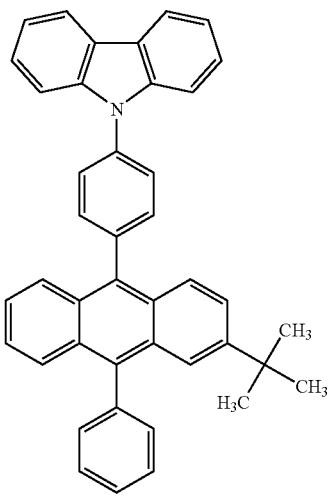
[347]
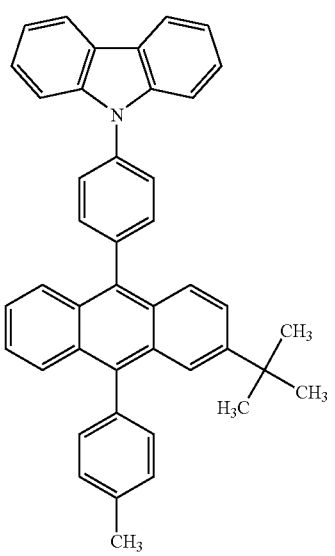
[348]
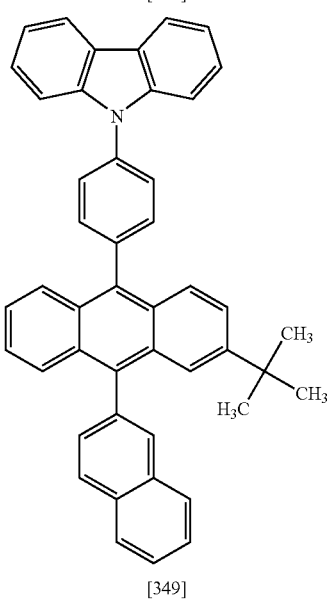
[349]

135
-continued
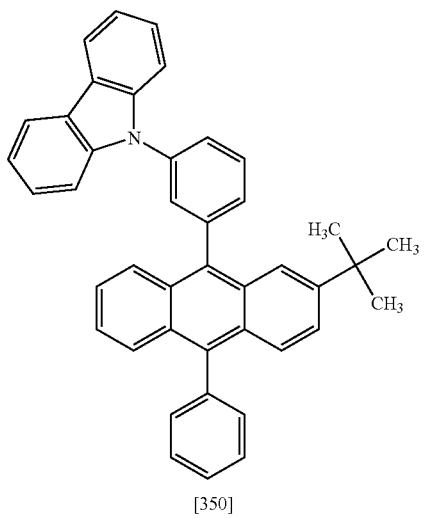
[350]
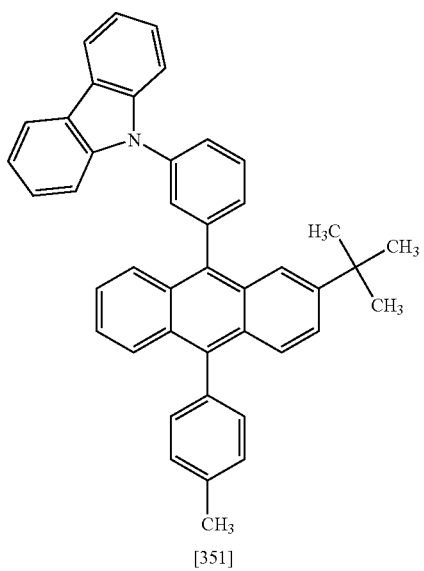
[351]
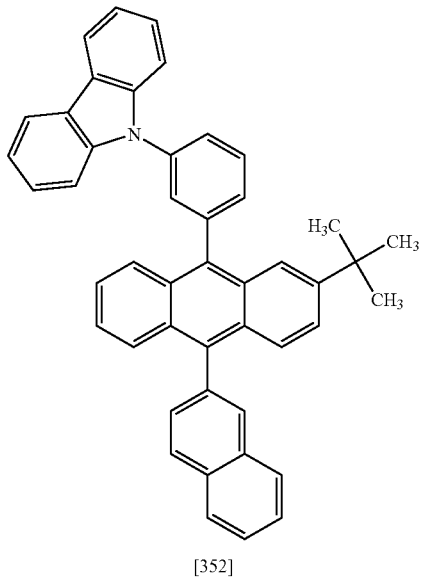
[352]
136
-continued
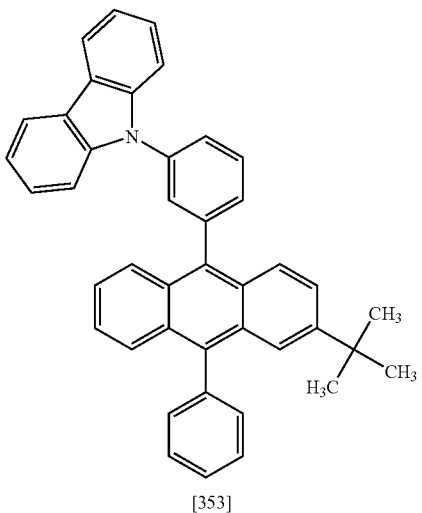
[353]
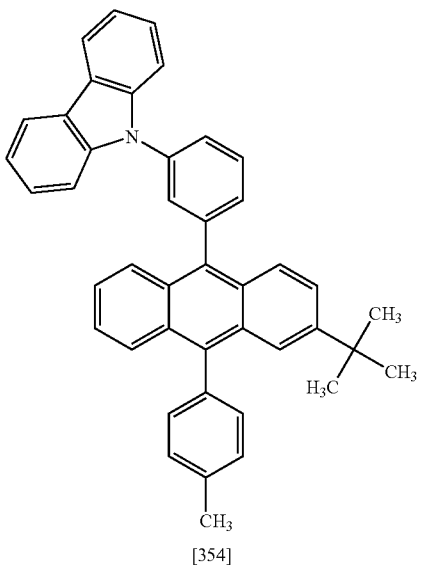
[354]
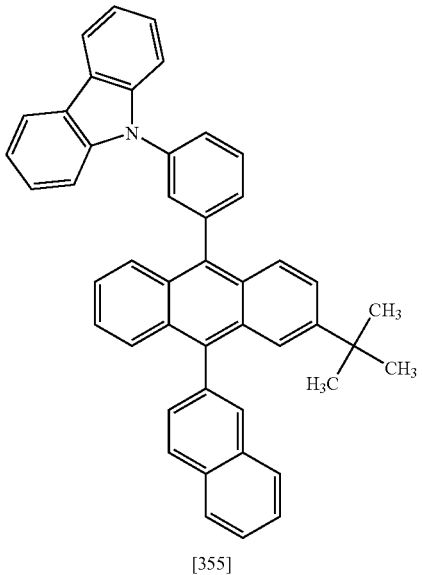
[355]

137
-continued
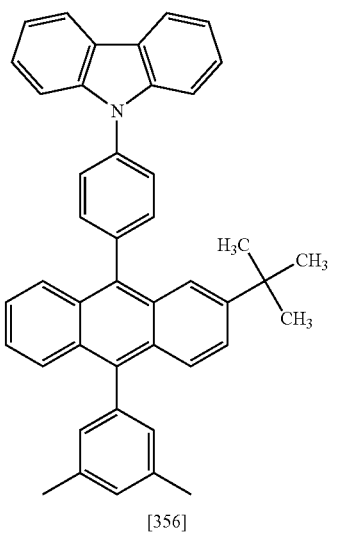
[356]
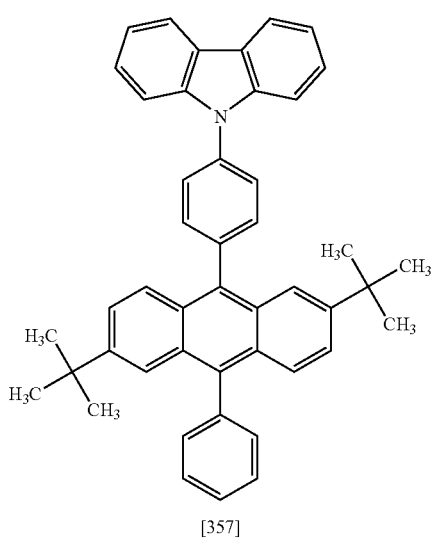
[357]
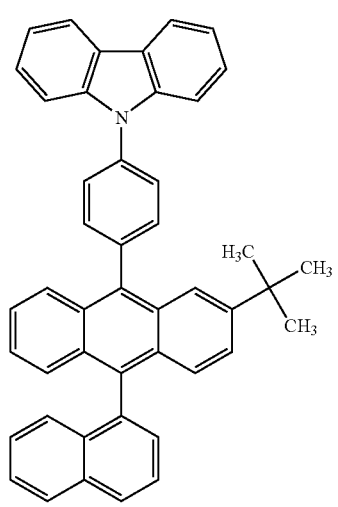
[358]
138
-continued
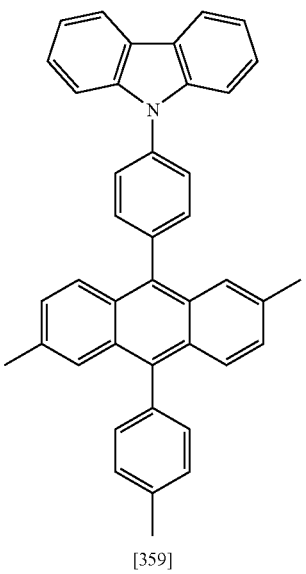
[359]
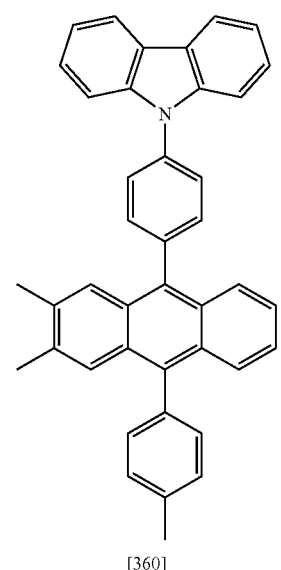
[360]
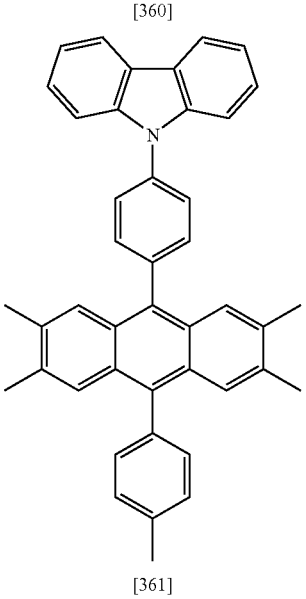
[361]

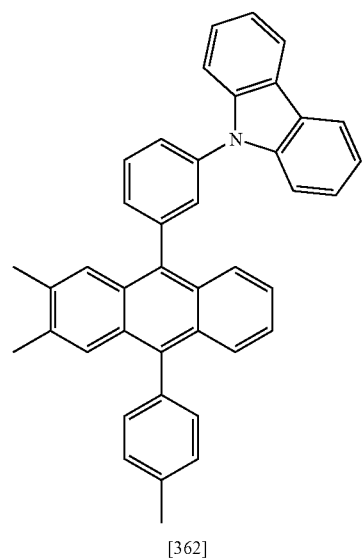
[362]
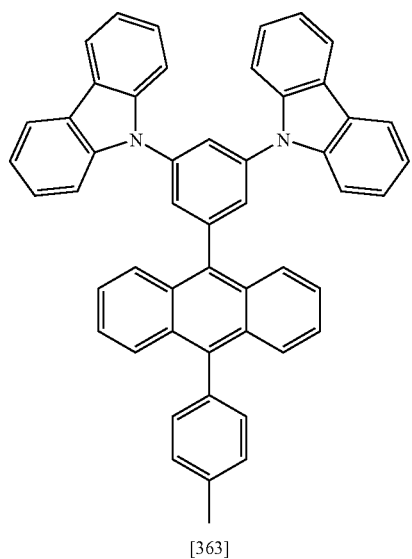
[363]
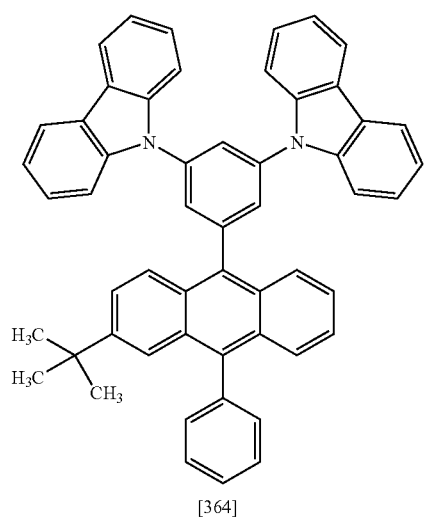
[364]
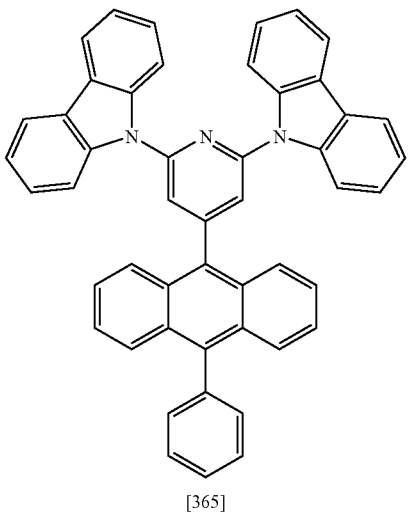
[365]
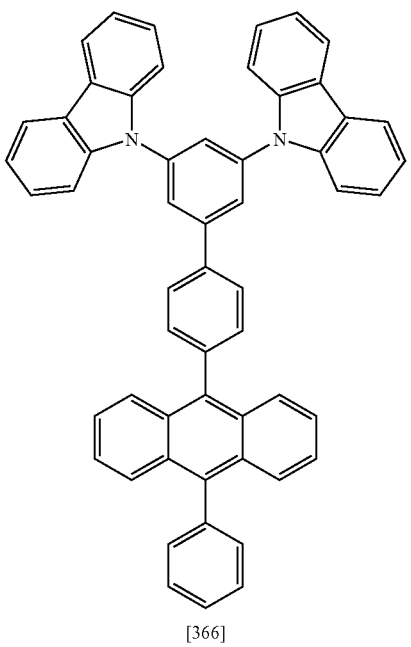
[366]
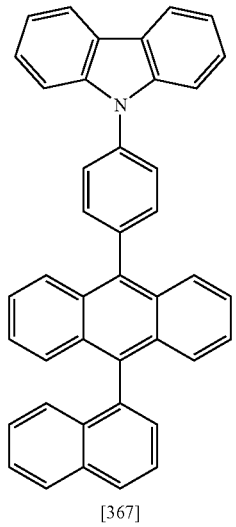
[367]

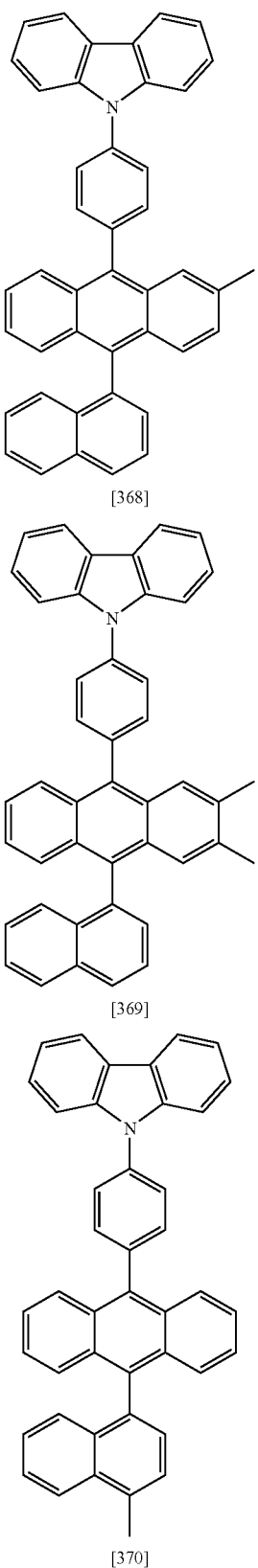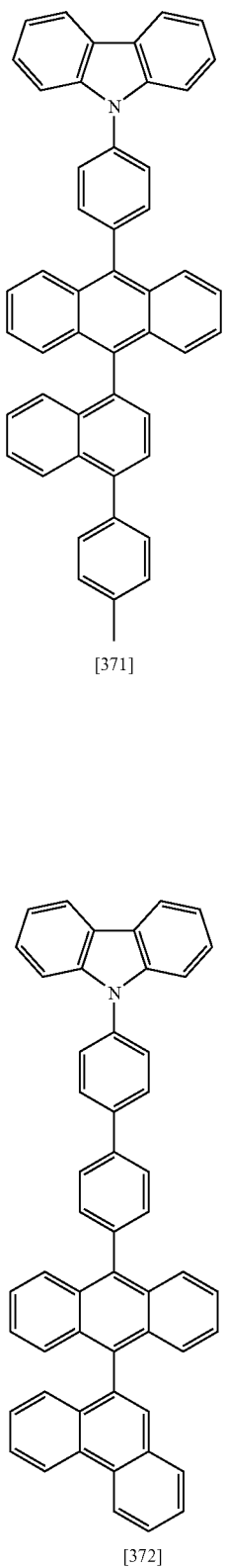

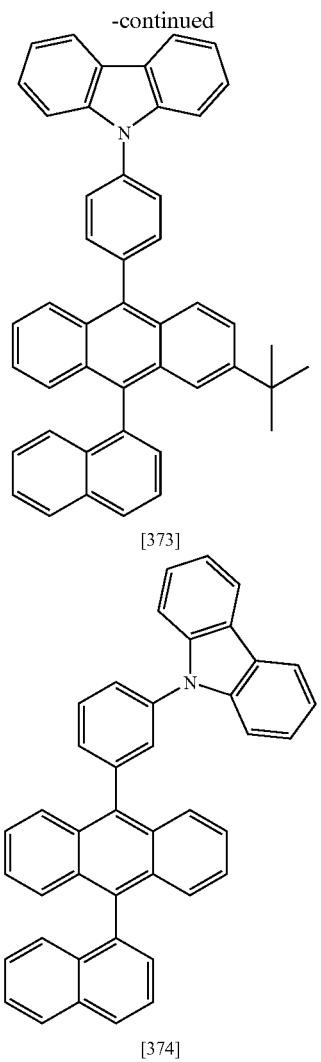

[373]

[374]

In the present invention, the electron transporting layer is a layer such as to control that an electron is injected from a cathode and further transported, and it is desirable that the electron transporting layer has high electron injection efficiency and efficiently transports the injected electron. Thus, it is required that electron affinity is high, electron mobility is high, stability is excellent, and impurities as trap are materials caused with difficulty during production and use. However, in the case of considering transportation balance between a hole and an electron, when mainly playing a role in being capable of efficiently blocking a hole from an anode from flowing to the side of a cathode without recombining, the effect of improving luminous efficiency is equal to a material with high electron transport capacity even though electron transport capacity is not so high. Accordingly, a hole hindering layer capable of efficiently blocking a hole from moving is also included as the same meaning in the electron transporting layer in the present invention.

The electron transporting material used for the electron transporting layer is not particularly limited, and examples thereof including compounds having a fused aryl ring and derivatives thereof, such as naphthalene and anthracene, a styryl-based aromatic ring derivative typified by 4,4'-bis(diphenylethenyl)biphenyl, a perylene derivative, perynone derivative, coumarin derivative, naphthalimide derivative, quinone derivatives such as anthraquinone and diphenoquinone, a phosphine oxide derivative, carbazole derivative, indole derivative, a quinolinol complex such as tris(8-quinolinolate)aluminum (III), a hydroxyazole complex such as a hydroxyphenyloxazole complex, an azomethine complex, tropolone metal complex, flavonol metal complex, and a compound comprising a heteroaryl ring with electron-accepting nitrogen.

The electron-accepting nitrogen in the present invention signifies a nitrogen atom forming a multiple bond with a neighboring atom. A nitrogen atom has high electronegativity, so that the multiple bond has electron-accepting properties. Therefore, a heteroaryl ring having electron-accepting nitrogen has high electron affinity. Examples of a heteroaryl ring having electron-accepting nitrogen include a pyridine ring, pyrazine ring, pyrimidine ring, quinoline ring, quinoxaline ring, naphthyridine ring, pyrimidopyrimidine ring, benzoquinoline ring, phenanthroline ring, imidazole ring, oxazole ring, oxadiazole ring, triazole ring, thiazole ring, thiadiazole ring, benzoxazole ring, benzothiazole ring, benzimidazole ring and phenanthroimidazole ring.

A compound comprising a heteroaryl ring having electron-accepting nitrogen of the present invention is preferably composed of an element selected from the group consisting of carbon, hydrogen, nitrogen, oxygen, silicon and phosphorus. A compound comprising a heteroaryl ring having electron-accepting nitrogen, which is composed of these elements, has so high electron transport capacity as to be capable of significantly reducing driving voltage.

Preferable examples of a compound, which comprises a heteroaryl ring having electron-accepting nitrogen and is composed of an element selected from the group consisting of carbon, hydrogen, nitrogen, oxygen, silicon and phosphorus, include a benzimidazole derivative, benzoxazole derivative, benzothiazole derivative, oxadiazole derivative, thiadiazole derivative, triazole derivative, pyrazine derivative, phenanthroline derivative, quinoxaline derivative, quinoline derivative, benzoquinoline derivative, oligopyridine derivatives such as bipyridine and terpyridine, quinoxaline derivative, and naphthyridine derivative. Above all, the following are preferably used from the viewpoint of electron transport capacity: an imidazole derivative such as tris(N-phenylbenzimidazole-2-yl)benzene, oxadiazole derivative such as 1,3-bis[(4-tert-butylphenyl)1,3,4-oxadiazolyl]phenylene, triazole derivative such as N-naphtyl-2,5-diphenyl-1,3,4-triazole, phenanthroline derivatives such as bathocuproine and 1,3-bis(2-phenyl-1,10-phenanthroline-9-yl)benzene, benzoquinoline derivative such as 2,2'-bis(benzo[h]quinoline-2-yl)-9,9'-spirobifluorene, bipyridine derivative such as 2,5-bis(6'-(2', 2"-bipyridyl))-1,1-dimethyl-3,4-diphenylsilo le, terpyridine derivative such as 1,3-bis(4'-(2,2':6'2"-terpyridinyl))benzene, and naphthyridine derivative such as bis(1-naphtyl)-4-(1,8-naphthyridine-2-yl)phenylphosphine oxide. In addition, phenanthroline dimers such as 1,3-bis(1,10-phenanthroline-9-yl)benzene, 2,7-bis(1,10-phenanthroline-9-yl)naphthalene and 1,3-bis(2-phenyl-1,10-phenanthroline-9-yl)benzene, and a bipyridine dimer such as 2,5-bis(6'-(2',2"-bipyridyl))-1,1-dimethyl-3,4-diphenylsilo le have extremely high effect of improving durability when combined with a pyrene compound represented by the general formula (1) of the present invention, and therefore are included in particularly preferable examples.

These electron transporting materials are used singly, and two kinds or more of the above-mentioned electron transporting materials may be used in mixture, or one kind or more of other electron transporting materials may be used in mixture with the above-mentioned electron transporting materials.

Metals such as alkaline metal and alkaline earth metal can also be used in mixture therewith. Ionization potential of the electron transporting layer is not particularly limited, being preferably 5.8 or higher to 8 eV or lower, more preferably 6 or higher to 7.5 eV or lower.

A method of forming each of the above-mentioned layers composing a light-emitting device is not particularly limited to heat-resistance deposition, electron beam deposition, sputtering, molecular layered method, coating method or the like, but typically, heat-resistance deposition or electron beam deposition is preferable from the viewpoint of device performance.

The thickness of the layers can not be limited by reason of depending on resistance values of luminescent substances, and yet is selected from a range of 1 to 1000 nm. The film thickness of each of the luminous layer, the electron transporting layer and the hole transporting layer is preferably 1 or more to 200 nm or less, more preferably 5 or more to 100 nm or less.

A light-emitting device of the present invention is a light-emitting device capable of converting electric energy into light. Here, electric energy mainly signifies direct current, and pulsed current and alternating current can also be used. Current values and voltage values are not particularly limited, and yet should be determined so that the highest luminance can be obtained at energy as low as possible in consideration of power consumption and lifetime of the device.

A light-emitting device of the present invention is preferably used, for example, for a display indicating in matrix and/or segment system.

A matrix system in the present invention is such that pixels for indicating are two-dimensionally disposed in lattice, mosaic and the like to indicate characters and images by an assembly of the pixels. Shapes and sizes of the pixels are determined by use thereof. For example, quadrangular pixels of 300 mm or less on a side are typically used for indicating images and characters of a personal computer, monitor and television, and pixels in the order of mm on a side are used in the case of a large-size display such as a display panel. Pixels in the same color are merely arrayed in the case of monochrome display, while pixels in red, green and blue are arrayed for indicating in the case of color display. In this case, a delta type and a stripe type are typically offered. A drive system of this matrix may be either of line-sequential system and active matrix. Line-sequential system has the advantage of being simpler in structure thereof; however, active matrix is occasionally more excellent in the case of considering operating characteristics, so that these need to be properly used in accordance with purposes.

A segment system (type) in the present invention is such that a pattern is formed so as to indicate previously determined information and a determined area is made to emit light. Examples thereof include time and temperature display in a digital clock and thermometer, operation status display of an audio instrument and electromagnetic cooker, and panel display of an automobile. The above-mentioned matrix display and segment display may coexist in the same panel.

A light-emitting device of the present invention is preferably used as a backlight of various apparatuses. A backlight is mainly used for the purpose of improving visibility of a display device that does not emit light for itself; a liquid crystal display device, clock, audio device, automobile panel, display board and mark. In particular, with regard to a backlight for a liquid crystal display device, above all, a personal computer in study of becoming thinner, abacklight using a light-emitting device in the present invention is characterized by being thinner and lighter-weight in consideration of rendering conventional types thinner with difficulty by reason of comprising fluorescent lamps and light guide plates.

EXAMPLES

The present invention is hereinafter described by referring to examples and is not limited thereto. The number of a compound in each of the following examples denotes the number of a compound described in the above-mentioned chemical formulae. An evaluation method on structural analysis is described below.

1H-NMR was measured in chloroform-d solution by using superconductive FTNMR EX-270 (manufactured by JEOL Ltd.).

Example 1

A Synthetic Method of a Compound [14]

A mixed solution of 5 g of 1-bromopyrene, 7.9 g of N-bromosuccinimide and 140 ml of dimethylformamide was stirred under nitrogen gas stream at a temperature of 80° C. for 10 hours. After cooling the mixed solution to room temperature, 400 ml of water was injected thereinto to filter the precipitate. The solid filtered off was washed with 50 ml of water, 100 ml of methanol and 200 ml of dichloromethane, and thereafter vacuum dried under a temperature of 70° C. to obtain 6.1 g of 1,3,6-tribromopyrene as pale-ocherous powder.

A mixed solution of 2 g of the above-mentioned 1,3,6-tribromopyrene, 2.5 g of 4-methylphenylboronic acid, 5.8 g of tripotassium phosphate, 0.88 g of tetrabutylammonium bromide, 61 mg of palladium acetate and 137 ml of deaerated dimethylformamide was heated while stirred under nitrogen gas stream at a temperature of 130° C. for 9 hours. After cooling the mixed solution to room temperature, 800 ml of water was injected thereinto to extract therefrom with 200 ml of dichloromethane. The organic layer was washed twice with 100 ml of water, dried by magnesium sulfate and thereafter concentrated by evaporation. The organic layer was purified by silica gel column chromatography and thereafter vacuum dried under a temperature of 70° C. to obtain 1.8 g of 1,3,6-tri(4-methylphenyl)pyrene as pale-yellow powder.

A mixed solution of 1.5 g of the above-mentioned 1,3,6-tri(4-methylphenyl)pyrene, 0.68 g of N-bromosuccinimide and 30 ml of dimethylformamide was stirred under nitrogen gas stream at a temperature of 60° C. for 6 hours. After cooling the mixed solution to room temperature, 50 ml of water was injected thereinto to extract therefrom with 100 ml of dichloromethane. The organic layer was washed twice with 50 ml of water, dried by magnesium sulfate and thereafter concentrated by evaporation. The organic layer was purified by silica gel column chromatography and thereafter vacuum dried under a temperature of 70° C. to obtain 1.5 g of 1-bromo-3,6,8-tri(4-methylphenyl)pyrene as pale-yellow powder.

A mixed solution of 400 mg of the above-mentioned 1-bromo-3,6,8-tri(4-methylphenyl)pyrene, 160 mg of 5-phenyloxazole, 355 mg of cesium carbonate, 20 mg of cuprous iodide, 9 mg of (tri-tert-butylphosphine)tetrafluoroborate, 4 mg of palladium acetate and 10 ml of dimethylformamide was heated while stirred under nitrogen gas stream at a temperature of 130° C. for 6 hours. After cooling the mixed solution to room temperature, 30 ml of water was injected thereinto and the resulting solution was filtered. The solid filtered off was washed with 30 ml of ethanol, thereafter purified by silica gel column chromatography and vacuum dried under a temperature of 70° C. to thereafter obtain 250 mg of a compound [14] as yellow powder. The results of 1H-NMR analysis of the obtained powder were as follows, and it was confirmed that the powder obtained in the above was the compound [14].

1H-NMR (CDCl3 (d=ppm)): 2.50 (ss, 9H), 7.09 (s, 1H), 7.34-7.43 (m, 17H), 8.06 (s, 1H), 8.23 (dd, 2H), 8.49 (d, 1H), 8.87 (s, 1H), 9.74 (d, 1H).

Example 2

A Synthetic Method of a Compound [17]

A mixed solution of 2 g of 1,3,6-tribromopyrene, 3.4 g of 4-methyl-1-naphthaleneboronic acid, 5.8 g of tripotassium phosphate, 0.88 g of tetrabutylammonium bromide, 61 mg of palladium acetate and 140 ml of deaerated dimethylformamide was heated while stirred under nitrogen gas stream at a temperature of 130° C. for 9 hours. After cooling the mixed solution to room temperature, 500 ml of water was injected thereinto to extract therefrom with 200 ml of dichloromethane. The organic layer was washed twice with 100 ml of water, dried by magnesium sulfate and thereafter concentrated by evaporation. The organic layer was purified by silica gel column chromatography and vacuum dried under a temperature of 70° C. to obtain 1.9 g of 1,3,6-tri(4-methylnaphthalene-1-yl)pyrene as milky-white powder.

A mixed solution of 1.9 g of the above-mentioned 1,3,6-tri(4-methylnaphthalene-1-yl)pyrene, 0.64 g of N-bromosuccinimide and 15 ml of dimethylformamide was stirred under nitrogen gas stream at a temperature of 60° C. for 6 hours. After cooling the mixed solution to room temperature, 50 ml of water was injected thereinto to extract therefrom with 100 ml of dichloromethane. The organic layer was washed twice with 50 ml of water, dried by magnesium sulfate and thereafter concentrated by evaporation. The organic layer was purified by silica gel column chromatography and thereafter vacuum dried under a temperature of 70° C. to obtain 1.5 g of 1-bromo-3,6,8-tri(4-methylnaphthalene-1-yl)pyrene as pale-yellow powder.

A mixed solution of 400 mg of the above-mentioned 1-bromo-3,6,8-tri(4-methylnaphthalene-1-yl)pyrene, 120 mg of 5-phenyloxazole, 280 mg of cesium carbonate, 16 mg of cuprous iodide, 7 mg of (tri-tert-butylphosphine)tetrafluoroborate, 3 mg of palladium acetate and 10 ml of dimethylformamide was heated while stirred under nitrogen gas stream at a temperature of 130° C. for 6 hours. After cooling the mixed solution to room temperature, 30 ml of water was injected thereinto and the resulting solution was filtered. The solid filtered off was washed with 30 ml of ethanol, thereafter purified by silica gel column chromatography and vacuum dried under a temperature of 70° C. to thereafter obtain 260 mg of a compound [17] as yellow powder. The results of 1H-NMR analysis of the obtained powder were as follows, and it was confirmed that the powder obtained in the above was a compound [17].

1H-NMR (CDCl3 (d=ppm)): 2.78 (s, 3H), 2.82 (s, 3H), 2.86 (s, 3H), 7.10 (s, 1H), 7.30-7.82 (m, 14H), 8.06-8.14 (m, 4H), 8.91 (s, 1H), 9.73 (d, 1H).

Example 3

A Synthetic Method of a Compound [68]

A mixed solution of 2 g of 1,6-dibromopyrene, 1.9 g of 4-methylphenylboronic acid, 5.9 g of tripotassium phosphate, 0.9 g of tetrabutylammonium bromide, 15 mg of palladium acetate and 30 ml of dimethylformamide was heated while stirred under nitrogen gas stream at a temperature of 130° C. for 6 hours. After cooling the mixed solution to room temperature, 30 ml of water was injected thereinto and the resulting solution was filtered. The solid filtered off was washed with 30 ml of ethanol, and thereafter recrystallized from toluene and vacuum dried to thereafter obtain 1.3 g of 1,6-bis(4-methylphenyl)pyrene.

Next, a mixed solution of 1.3 g of 1,6-bis(4-methylphenyl)pyrene, 0.6 g of N-bromosuccinimide and 30 ml of dimethylformamide was stirred under nitrogen gas stream at a temperature of 60° C. for 5 hours. After cooling the mixed solution to room temperature, 30 ml of water was injected thereinto to extract therefrom with 100 ml of dichloromethane. The organic layer was washed twice with 50 ml of water, dried by magnesium sulfate and thereafter evaporated. The organic layer was recrystallized from toluene and vacuum dried to thereafter obtain 0.7 g of 3-bromo-1,6-bis(4-methylphenyl)pyrene.

Next, a mixed solution of 0.7 g of 3-bromo-1,6-bis(4-methylphenyl)pyrene, 0.22 g of benzoxazole, 0.6 g of cesium carbonate, 37 mg of cuprous iodide, 14.5 mg of triphenylphosphine, 7 mg of palladium acetate and 30 ml of dimethylformamide was heated while stirred under nitrogen gas stream at a temperature of 130° C. for 6 hours. After cooling the mixed solution to room temperature, 30 ml of water was injected thereinto and the resulting solution was filtered. The solid filtered off was washed with 30 ml of ethanol, thereafter purified by silica gel column chromatography and vacuum dried to thereafter obtain 0.35 g of a yellow crystal. The results of 1H-NMR analysis of the obtained powder were as follows, and it was confirmed that the yellow crystal obtained in the above was a compound [68].

1H-NMR (CDCl3 (d=ppm)): 2.52 (ss, 6H), 7.39-7.43 (m, 6H), 7.57-7.67 (m, 5H), 7.90 (dd, 1H), 8.05 (d, 1H), 8.13 (d, 1H), 8.23-8.28 (dd, 2H), 8.46 (d, 1H), 8.87 (s, 1H), 9.72 (d, 1H).

Example 4

A Synthetic Method of a Compound [87]

A mixed solution of 5 g of 1,6-dibromopyrene, 2.1 g of benzothiazole, 5 g of cesium carbonate, 0.31 g of cuprous iodide, 0.12 g of triphenylphosphine, 57 mg of palladium acetate and 50 ml of dimethylformamide was heated while stirred under nitrogen gas stream at a temperature of 130° C. for 6 hours. The mixed solution was cooled to room temperature, thereafter filtered and washed with 10 ml of dimethylformamide and 100 ml of dichloromethane. The filtrate was washed twice with 50 ml of water, dried by magnesium sulfate and thereafter evaporated. The filtrate was purified by silica gel column chromatography and vacuum dried to thereafter obtain 1.1 g of 6-bromo-1-(benzothiazole-2-yl)pyrene.

Next, a mixed solution of 0.3 g of 6-bromo-1-(benzothiazole-2-yl)pyrene, 0.16 g of 4-tert-butylphenylboronic acid, 0.38 g of tripotassium phosphate, 58 mg of tetrabutylammonium bromide, 1 mg of palladium acetate and 5 ml of dimethylformamide was heated while stirred under nitrogen gas stream at a temperature of 130° C. for 6 hours. The mixed solution was cooled to room temperature, thereafter washed with 10 ml of dimethylformamide, 10 ml of water and 10 ml of ethanol, and thereafter purified by silica gel column chromatography. The mixed solution was vacuum dried to thereafter obtain 0.15 g of a yellow crystal. The results of 1H-NMR analysis of the obtained powder were as follows, and it was confirmed that the yellow crystal obtained in the above was a compound [87].

1H-NMR (CDCl3 (d=ppm)): 1.46 (s, 6H), 7.51 (t, 1H), 7.57-7.63 (m, 5H), 8.01-8.07 (m, 3H), 8.22-8.36 (m, 5H), 8.44 (d, 1H), 9.32 (d, 1H).

Example 5

A Synthetic Method of a Compound [88]

A mixed solution of 0.5 g of 3-bromo-1,6-bis(4-methylphenyl)pyrene, 0.19 g of benzothiazole, 0.44 g of cesium carbonate, 27 mg of cuprous iodide, 10.5 mg of triphenylphosphine, 5 mg of palladium acetate and 20 ml of dimethylformamide was heated while stirred under nitrogen gas stream at a temperature of 130° C. for 6 hours. The mixed solution was cooled to room temperature, thereafter filtered and washed with 10 ml of dimethylformamide and 10 ml of ethanol. The filtrate was purified by silica gel column chromatography and vacuum dried to thereafter obtain 0.20 g of a yellow crystal. The results of 1H-NMR analysis of the obtained powder were as follows, and it was confirmed that the yellow crystal obtained in the above was a compound [88].

1H-NMR (CDCl3 (d=ppm)): 2.51 (ss, 6H), 7.37-7.48 (m, 5H), 7.55-7.61 (m, 5H), 8.01-8.06 (m, 2H), 8.12 (d, 1H), 8.21-8.27 (m, 3H), 8.37 (d, 1H), 8.41 (s, 1H), 9.23 (d, 1H).

Example 6

A Synthetic Method of a Compound [111]

A mixed solution of 5 g of 1,3,6-tribromopyrene, 7.84 g of 1-naphtylboronic acid, 19.4 g of tripotassiumphosphate, 2.94 g of tetrabutylammonium bromide, 205 mg of palladium acetate and 175 ml of deaerated dimethylformamide was heated while stirred under nitrogen gas stream at a temperature of 130° C. for 2 hours. After cooling the mixed solution to room temperature, 100 ml of water was injected thereinto and the resulting solution was filtered. The solid filtered off was purified by silica gel column chromatography and vacuum dried to thereafter obtain 1,3,6-tri(naphthalene-1-yl)pyrene.

Next, a mixed solution of 3.22 g of 1,3,6-tri(naphthalene-1-yl)pyrene, 1.17 g of N-bromosuccinimide and 30 ml of dimethylformamide was heated while stirred under nitrogen gas stream at a temperature of 70° C. for 2 hours. After cooling the mixed solution to room temperature, 100 ml of water was injected thereinto and the resulting solution was filtered. The solid filtered off was purified by silica gel column chromatography and vacuum dried to thereafter obtain 1-bromo-3,6,8-tri(naphthalene-1-yl)pyrene.

Next, a mixed solution of 400 mg of 1-bromo-3,6,8-tri(naphthalene-1-yl)pyrene, 145 mg of benzoxazole, 218 mg of cesium carbonate, 18 mg of cuprous bromide, 18 mg of (tri-tert-butylphosphine)tetrafluoroborate, 7 mg of palladium acetate and 10 ml of deaerated dimethylformamide was heated while stirred under nitrogen gas stream at a temperature of 150° C. for 2 hours. After cooling the mixed solution to room temperature, 50 ml of water was injected thereinto to extract therefrom with 100 ml of dichloromethane. The organic layer was washed twice with 50 ml of water, dried by magnesium sulfate and thereafter concentrated by evaporation. The organic layer was purified by silica gel column chromatography and vacuum dried to thereafter obtain a compound [111]. The results of 1H-NMR analysis of the obtained powder were as follows, and it was confirmed that the yellow crystal obtained in the above was the compound [111].

1H-NMR (CDCl3 (d=ppm)): 7.28-8.11 (m, 28H), 8.17 (s, 1H), 8.95 (s, 1H), 9.77 (d, 1H)

Example 7

A Synthetic Method of a Compound [115]

A compound [115] was obtained in the same manner as Example 6 except for replacing benzoxazole with 5-methylbenzoxazole. The results of 1H-NMR analysis of the obtained powder were as follows, and it was confirmed that the yellow crystal obtained in the above was the compound [115].

1H-NMR (CDCl3 (d=ppm)): 2.50 (s, 3H), 7.17-7.71 (m, 19H), 7.91-8.10 (m, 8H), 8.16 (s, 1H), 8.93 (s, 1H), 9.76 (d, 1H).

Example 8

A Synthetic Method of a Compound [116]

A compound [116] was obtained in the same manner as Example 6 except for replacing benzoxazole with 6-methylbenzoxazole. The results of 1H-NMR analysis of the obtained powder were as follows, and it was confirmed that the yellow crystal obtained in the above was the compound [116].

1H-NMR (CDCl3 (d=ppm)): 2.50 (s, 3H), 7.14-7.72 (m, 19H), 7.90-8.10 (m, 8H), 8.16 (s, 1H), 8.93 (s, 1H), 9.75 (d, 1H).

Example 9

A Synthetic Method of a Compound [117]

A compound [117] was obtained in the same manner as Example 1 except for replacing benzoxazole with 5-tert-butylbenzoxazole. The results of 1H-NMR analysis of the obtained powder were as follows, and it was confirmed that the yellow crystal obtained in the above was the compound [117].

1H-NMR (CDCl3 (d=ppm)): 1.40 (s, 9H), 7.30-7.70 (m, 19H), 7.87-8.10 (m, 9H), 8.17 (s, 1H), 8.94 (s, 1H).

Example 10

A glass substrate (manufactured by ASAHI GLASS CO., LTD., 15 Ohm/Square, electron beam deposition product) on which an ITO transparent conductive film was accumulated with a thickness of 150 nm was cut to a size of 30×40 mm, and etched. The obtained substrate was subject to ultrasonic cleaning with each of acetone and "SEMICOCLEAN (registered trademark) 56" (manufactured by Furuuchi Chemical Corporation) for 15 minutes, and then cleaned with ultrapure water. Subsequently, the substrate was subject to ultrasonic cleaning with isopropyl alcohol for 15 minutes, and then immersed in hot methanol for 15 minutes and dried. Immediately before producing a device, this substrate was subject to UV-ozone treatment for 1 hour and placed in a vacuum evaporator to exhaust until degree of vacuum in the evaporator became 5×10-5 Pa or less. First, through a resistance heating method, copper phthalocyanine was deposited with a thickness of 10 nm as a hole injecting material and 4,4'-bis (N-(1-naphthyl)-N-phenylamino)biphenyl was deposited with a thickness of 50 nm as a hole transporting material. Next, with regard to a luminescent material, H-1 represented below was deposited as a host material and the compound [14] was deposited as a dopant material with a thickness of 35 nm so that doping concentration became 2%. Next, E-1 represented below was laminated with a thickness of 20 nm as an electron transporting material. Next, lithium fluoride was deposited with a thickness of 0.5 nm, and thereafter aluminum was deposited with a thickness of 1000 nm to form a cathode and produce a device of 5×5 mm square. The film thickness herein was an indicated value of a crystal oscillation film thickness monitor. Blue light emission with a high luminous efficiency of 3.0 cd/A was obtained from this light-emitting device. This light-emitting device offered a luminance half-value period of 3300 hours when subject to a direct current drive of 10 mA/cm2.

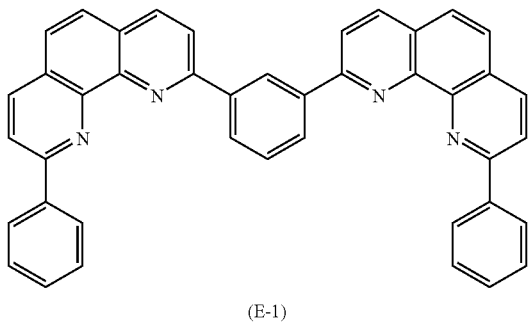

(E-1)

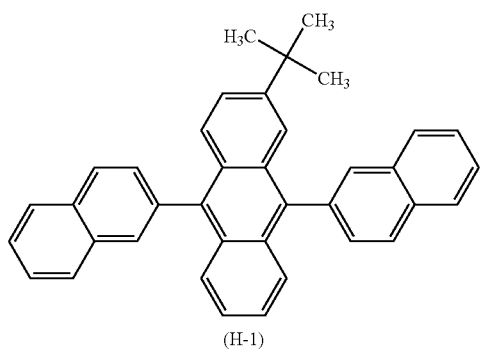

(H-1)

Examples 11 to 37

A light-emitting device was produced in the same manner as Example 10 except for using materials described in Table 1 as dopant materials. The results of each example were shown in Table 1.

TABLE 1

| | Light Emission Layer | | Electron Transporting | Color of Light | Luminous Efficiency | Brightness half-life period |
|---|---|---|---|---|---|---|
| | Host Material | Dopant Material | Layer | Emission | (cd/A) | (h) |
| Example10 | H-1 | Compound [14] | E-1 | Blue | 3.0 | 3300 |
| Example11 | H-1 | Compound [17] | E-1 | Blue | 3.1 | 3000 |
| Example12 | H-1 | Compound [2] | E-1 | Blue | 1.9 | 1500 |
| Example13 | H-1 | Compound [3] | E-1 | Blue | 2.5 | 2800 |
| Example14 | H-1 | Compound [4] | E-1 | Blue | 2.7 | 3000 |
| Example15 | H-1 | Compound [36] | E-1 | Blue | 2.8 | 2900 |
| Example16 | H-1 | Compound [43] | E-1 | Blue | 2.5 | 2800 |
| Example17 | H-1 | Compound [49] | E-1 | Blue | 2.6 | 2900 |
| Example18 | H-1 | Compound [55] | E-1 | Blue | 2.5 | 2800 |
| Example19 | H-1 | Compound [57] | E-1 | Blue | 2.4 | 2900 |
| Example20 | H-1 | Compound [64] | E-1 | Blue | 2.0 | 2500 |
| Example21 | H-1 | Compound [87] | E-1 | Blue | 2.7 | 4500 |
| Example22 | H-1 | Compound [68] | E-1 | Blue | 3.0 | 5000 |
| Example23 | H-1 | Compound [88] | E-1 | Blue | 2.5 | 4000 |
| Example24 | H-1 | Compound [111] | E-1 | Blue | 3.1 | 5000 |
| Example25 | H-1 | Compound [115] | E-1 | Blue | 3.3 | 4800 |
| Example26 | H-1 | Compound [116] | E-1 | Blue | 3.1 | 4800 |
| Example27 | H-1 | Compound [117] | E-1 | Blue | 3.2 | 4900 |
| Example28 | H-1 | Compound [131] | E-1 | Blue | 3.5 | 4800 |
| Example29 | H-1 | Compound [132] | E-1 | Blue | 3.3 | 4700 |
| Example30 | H-1 | Compound [134] | E-1 | Blue | 3.2 | 4300 |
| Example31 | H-1 | Compound [135] | E-1 | Blue | 3.0 | 4200 |
| Example32 | H-1 | Compound [137] | E-1 | Blue | 3.1 | 4400 |
| Example33 | H-1 | Compound [118] | E-1 | Blue | 3.1 | 4500 |
| Example34 | H-1 | Compound [159] | E-1 | Blue | 3.0 | 4400 |
| Example35 | H-1 | Compound [147] | E-1 | Blue | 3.0 | 4700 |
| Example36 | H-1 | Compound [146] | E-1 | Blue | 3.1 | 4600 |
| Example37 | H-1 | Compound [164] | E-1 | Blue | 3.1 | 4800 |
| Comparative Example1 | H-1 | D-1 | E-1 | Blue | 1.1 | 500 |
| Comparative Example2 | H-1 | D-2 | E-1 | Blue | 1.8 | 400 |
| Comparative Example3 | H-1 | D-3 | E-1 | Blue | 1.5 | 450 |
| Comparative Example4 | H-1 | D-4 | E-1 | Blue | 1.8 | 300 |

Comparative Example 1

A light-emitting device was produced in the same manner as Example 10 except for using D-1 represented by the following formula as a dopant material. When this light-emitting device was subject to a direct current drive of 10 mA/cm2, blue light emission with a luminous efficiency of 1.1 cd/A was obtained. When this light-emitting device was subject to continuous drive with a direct current of 10 mA/cm2, luminance was reduced by half in 500 hours.

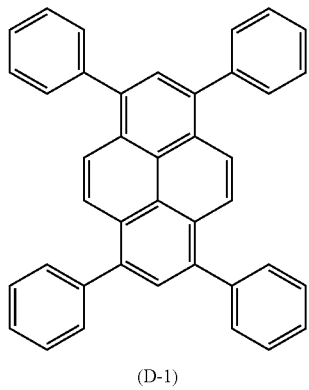

(D-1)

Comparative Example 2

A light-emitting device was produced in the same manner as Comparative Example 1 except for using D-2 represented below as a dopant material. When this light-emitting device was subject to a direct current drive of 10 mA/cm2, blue light emission with a luminous efficiency of 1.8 cd/A was obtained. When this light-emitting device was subject to continuous drive with a direct current of 10 mA/cm2, luminance was reduced by half in 400 hours.

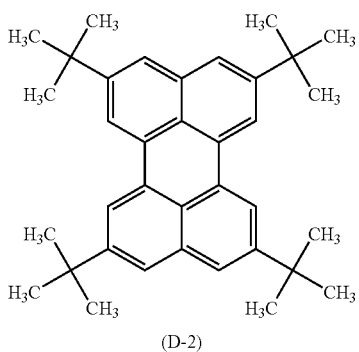

(D-2)

Comparative Example 3

A light-emitting device was produced in the same manner as Comparative Example 1 except for using D-3 represented below as a dopant material. When this light-emitting device was subject to a direct current drive of 10 mA/cm2, blue light emission with a luminous efficiency of 1.5 cd/A was obtained. When this light-emitting device was subject to continuous drive with a direct current of 10 mA/cm2, luminance was reduced by half in 450 hours.

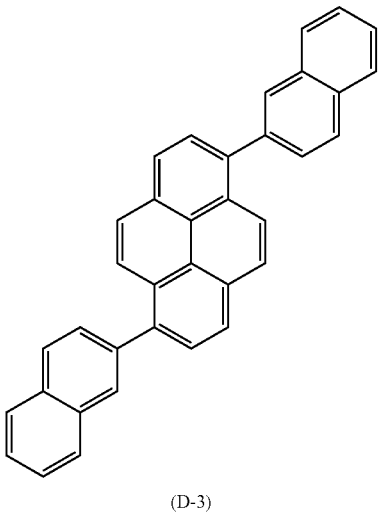

(D-3)

Comparative Example 4

A light-emitting device was produced in the same manner as Comparative Example 1 except for using D-4 represented below as a dopant material. When this light-emitting device was subject to a direct current drive of 10 mA/cm2, blue light emission with a luminous efficiency of 1.8 cd/A was obtained. When this light-emitting device was subject to continuous drive with a direct current of 10 mA/cm2, luminance was reduced by half in 300 hours.

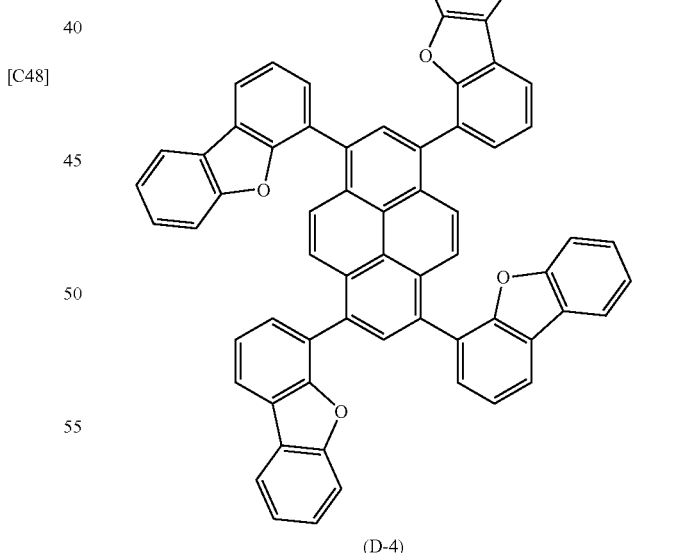

(D-4)

Example 38

A light-emitting device was produced in the same manner as Example 10 except for using H-2 represented below as a host material. When this light-emitting device was subject to a direct current drive of 10 mA/cm2, blue light emission with a high luminous efficiency of 2.7 cd/A was obtained. When this light-emitting device was subject to continuous drive with a direct current of 10 mA/cm2, a luminance half-value period was 2500 hours.

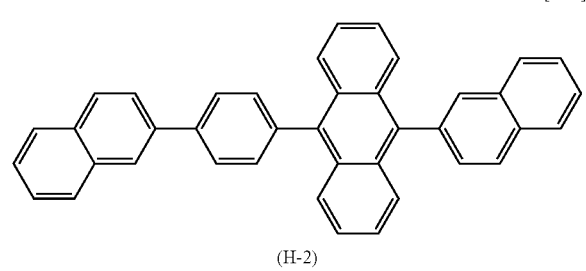

(H-2)

Examples 39 to 49

A light-emitting device was produced in the same manner as Example 38 except for using materials described in Table 2 as host materials and electron transporting materials. The results of each example were shown in Table 2. H-3 in Table 2 was a compound represented by the following formula.

Example 50

A light-emitting device was produced in the same manner as Example 10 except for using the compound [279] and E-2 represented below as a host material and an electron transporting material, respectively. When this light-emitting device was subject to a direct current drive of 10 mA/cm2, blue light emission with a high luminous efficiency of 3.2 cd/A was obtained. When this light-emitting device was subject to continuous drive with a direct current of 10 mA/cm2, a luminance half-value period was 5000 hours.

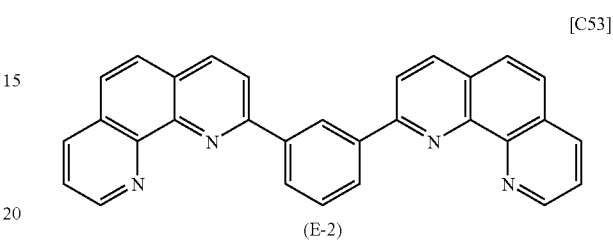

(E-2)

Examples 51 to 59

A light-emitting device was produced in the same manner as Example 50 except for using materials described in Table 3 as host materials and electron transporting materials. The results of each example were shown in Table 3. E-3, E-4, E-5 and E-6 in Table 3 were compounds represented by the following formulae.

TABLE 2

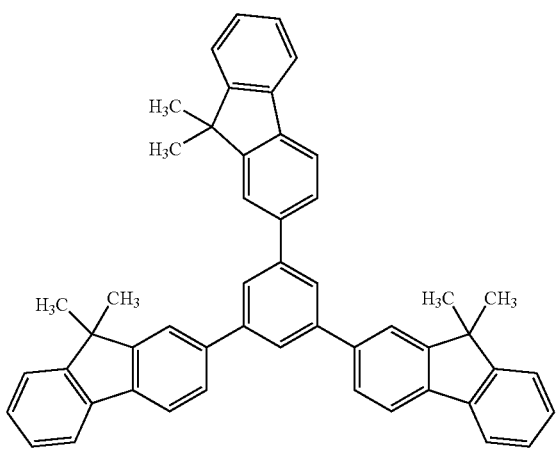

(H-3)

| | Light Emission Layer | | Electron Transporting Layer | Color of Light Emission | Luminous Efficiency (cd/A) | Brightness half-life period (h) |
|---|---|---|---|---|---|---|
| | Host Material | Dopant Material | | | | |
| Example38 | H-2 | Compound[14] | E-1 | Blue | 2.7 | 2500 |
| Example39 | H-3 | Compound [14] | E-1 | Blue | 2.6 | 2600 |
| Example40 | Compound [281] | Compound [14] | E-1 | Blue | 2.5 | 4800 |
| Example41 | Compound [326] | Compound [14] | E-1 | Blue | 3.0 | 3000 |
| Example42 | Compound [279] | Compound [14] | E-1 | Blue | 3.3 | 6000 |
| Example43 | Compound [353] | Compound [14] | E-1 | Blue | 2.8 | 4700 |
| Example44 | H-2 | Compound [68] | E-1 | Blue | 2.8 | 3500 |
| Example45 | H-3 | Compound [68] | E-1 | Blue | 2.6 | 3300 |
| Example46 | Compound [281] | Compound [68] | E-1 | Blue | 2.5 | 7000 |
| Example47 | Compound [326] | Compound [68] | E-1 | Blue | 3.2 | 3000 |
| Example48 | Compound [279] | Compound [68] | E-1 | Blue | 3.5 | 10000 |
| Example49 | Compound [353] | Compound [68] | E-1 | Blue | 2.9 | 6000 |

TABLE 3

[T3]

| | Light Emission Layer | | Electron Transporting | Color of Light | Luminous Efficiency | Brightness half life period |
|---|---|---|---|---|---|---|
| | Host Material | Dopant Material | Layer | Emission | (cd/A) | (h) |
| Example50 | Compound [279] | Compound [14] | E-2 | Blue | 3.2 | 5000 |
| Example51 | Compound [279] | Compound [14] | E-3 | Blue | 2.3 | 2000 |
| Example52 | Compound [279] | Compound [14] | E-4 | Blue | 2.8 | 4000 |
| Example53 | Compound [279] | Compound [14] | E-5 | Blue | 3.0 | 2500 |
| Example54 | Compound [279] | Compound [14] | E-6 | Blue | 2.4 | 2200 |
| Example55 | Compound [279] | Compound [68] | E-2 | Blue | 3.5 | 10000 |
| Example56 | Compound [279] | Compound [68] | E-3 | Blue | 2.6 | 4000 |
| Example57 | Compound [279] | Compound [68] | E-4 | Blue | 3.0 | 8000 |
| Example58 | Compound [279] | Compound [68] | E-5 | Blue | 3.2 | 5000 |
| Example59 | Compound [279] | Compound [68] | E-6 | Blue | 2.5 | 4200 |

[C54]

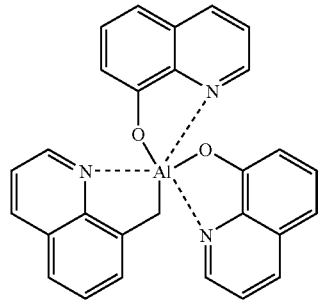

(E-3)

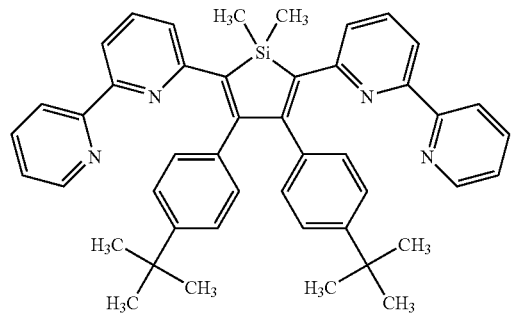

(E-4)

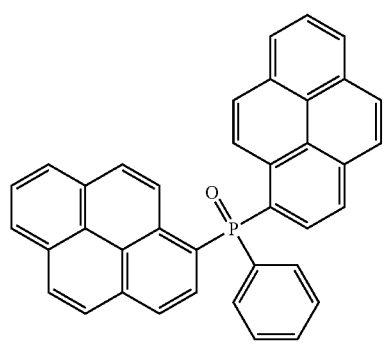

(E-5)

| | | Electron | Color of | Luminous | Brightness half |
| Light Emission Layer | | Transporting | Light | Efficiency | life period |
| Host Material | Dopant Material | Layer | Emission | (cd/A) | (h) |

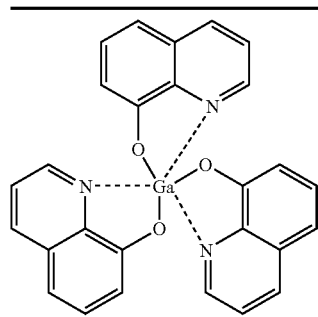

(E-6)

Example 60

A light-emitting device was produced in the same manner as Example 10 except that, with regard to a luminescent material, the compound [279] was deposited as a host material and the compound [14] was deposited as a dopant material with a thickness of 5 nm so that doping concentration became 2%, and thereafter, with regard to another luminescent material, the compound [279] was laminated as a host material and 5,6,11,12-tetraphenylnaphthacene was laminated as a dopant material with a thickness of 30 nm so that doping concentration became 1%. White light emission with a high luminous efficiency of 6.5 cd/A was obtained from this light-emitting device. This light-emitting device offered a luminance half-value period of 3500 hours when subject to a direct current drive of 10 mA/cm2.

Example 61

A light-emitting device was produced in the same manner as Example 10 except that, with regard to a luminescent material, the compound [279] was deposited as a host material and the compound [132] was deposited as a dopant material with a thickness of 5 nm so that doping concentration became 2%, and thereafter, with regard to another luminescent material, the compound [279] was laminated as a host material and 5,6,11,12-tetraphenylnaphthacene was laminated as a dopant material with a thickness of 30 nm so that doping concentration became 1%. White light emission with a high luminous efficiency of 7.0 cd/A was obtained from this light-emitting device. This light-emitting device offered a luminance half-value period of 5000 hours when subject to a direct current drive of 10 mA/cm2.

Example 62

A light-emitting device was produced in the same manner as Example 10 except that, with regard to a luminescent material, the compound [279] was deposited as a host material and the compound [131] was deposited as a dopant material with a thickness of 5 nm so that doping concentration became 2%, and thereafter, with regard to another luminescent material, the compound [279] was laminated as a host material and 5,6,11,12-tetraphenylnaphthacene was laminated as a dopant material with a thickness of 30 nm so that doping concentration became 1%. White light emission with a high luminous efficiency of 7.5 cd/A was obtained from this light-emitting device. This light-emitting device offered a luminance half-value period of 5500 hours when subject to a direct current drive of 10 mA/cm2.

Example 63

A light-emitting device was produced in the same manner as Example 10 except that, with regard to a luminescent material, the compound [279] was deposited as a host material and 1,3,5,7-tetra(4-tert-butylphenyl)-8-phenyl-4,4-difluoro-4-b ora-3a,4a-diaza-s-indacene was deposited as a dopant material with a thickness of 5 nm so that doping concentration became 1%, thereafter the compound [279] was deposited as a host material and 2,3,5,6-1H,4H-tetrahydro-9-(2'-benzothiazolyl)quinolizino[9,9a,1-gh]coumarin was deposited as a dopant material with a thickness of 5 nm so that doping concentration became 2%, and, with regard to another luminescent material, the compound [279] was laminated as a host material and the compound [111] was laminated as a dopant material with a thickness of 30 nm so that doping concentration became 2%. White light emission with a high luminous efficiency of 7.5 cd/A was obtained from this light-emitting device. This light-emitting device offered a luminance half-value period of 7000 hours when subject to a direct current drive of 10 mA/cm2.

Example 64

A glass substrate (manufactured by ASAHI GLASS CO., LTD., 15 Ohm/Square, electron beam deposition product) on which an ITO transparent conductive film was accumulated with a thickness of 150 nm was cut to a size of 30×40 mm, which ITO conductive film was patterned into a stripe of 300 mm-pitch (a residual width of 270 mm)×32 pieces by a photolithographic method. One side of the ITO stripe in a long side direction was widened to 1.27 mm-pitch (an opening width of 800 microns) in order to facilitate electrical connection to the exterior. The obtained substrate was subject to ultrasonic cleaning with each of acetone and "SEMICOCLEAN (registered trademark) 56" (manufactured by Furuuchi Chemical Corporation) for 15 minutes, and then cleaned with ultrapure water. Subsequently, the substrate was subject to ultrasonic cleaning with isopropyl alcohol for 15 minutes, and then immersed in hot methanol for 15 minutes and dried. Immediately before producing a device, this substrate was subject to UV-ozone treatment for 1 hour and placed in a vacuum evaporator to exhaust until degree of vacuum in the evaporator became 5×10-4 Pa or less. First, through a resistance heating method, 4,4'-bis(N-(1-naphthyl)-N-phenylamino)biphenyl was deposited with a thickness of 150 nm as a hole transporting material. Next, H-1 was deposited as a host material and the compound [68] was deposited as a dopant material with a thickness of 35 nm so that doping concentration became 2%. Next, E-1 was laminated with a thickness of 20 nm as an electron transporting material. The film thickness herein was an indicated value of a crystal oscillation film thickness monitor. Next, a mask such that 16 pieces of 250 microns-opening (corresponding to a residual width of 50 microns and 300 microns-pitch) were made on a Kovar plate with a thickness of 50 microns by wet etching was subject to mask exchange so as to be orthogonal to the ITO stripe in a vacuum and fixed by a magnet from the back so that the mask and the ITO substrate adhered closely. Lithium fluoride was deposited with a thickness of 0.5 nm to thereafter deposit aluminum with a thickness of 200 nm and produce a 32×16-dot matrix device. When the device was subject to matrix drive, characters were indicated without crosstalk.

INDUSTRIAL APPLICABILITY

A light-emitting device of the present invention is preferably utilizable in the fields such as display device, flat-panel display, backlight, illumination, interior, mark, signboard, electrophotographic apparatus and light signal generator.

The invention claimed is:
1. A light-emitting device material containing a pyrene compound represented by the following general formula (4):

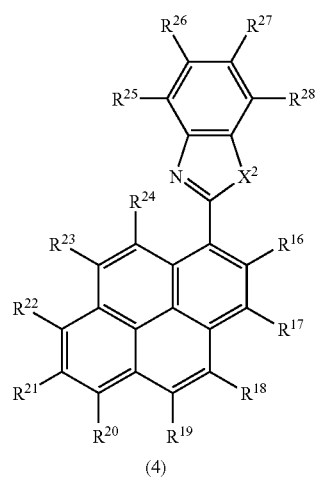

[C4]

(4)

wherein $R^{16}$ to $R^{24}$ each may be the same or different and are selected from among hydrogen, alkyl group, cycloalkyl group, heterocyclic group, alkenyl group, cycloalkenyl group, alkynyl group, alkoxy group, alkylthio group, arylether group, arylthioether group, aryl group, heteroaryl group, halogen, cyano group, carbonyl group, carboxyl group, oxycarbonyl group, carbamoyl group, amino group, phosphine oxide group and condensed ring formed between adjacent groups; $R^{25}$ to $R^{28}$ each may be the same or different and are selected from among hydrogen, alkyl group, cycloalkyl group, heterocyclic group, alkenyl group, cycloalkenyl group, alkynyl group, alkoxy group, alkylthio group, arylether group, arylthioether group, aryl group, heteroaryl group, halogen, cyano group, carbonyl group, carboxyl group, oxycarbonyl group, carbamoyl group, amino group and phosphine oxide group; and $X^2$ is selected from among groups represented by the following general formula (5):

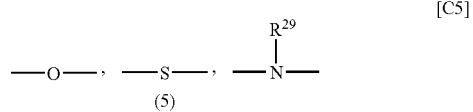

[C5]

(5)

wherein $R^{29}$ is selected from the group consisting of hydrogen, alkyl group, cycloalkyl group, heterocyclic group, alkenyl group, cycloalkenyl group, alkynyl group, aryl group, heteroaryl group, cyano group, carbonyl group, carboxyl group, oxycarbonyl group and carbamoyl group, wherein at least one of $R^{16}$ to $R^{24}$ is an aryl group or heteroaryl group.

2. A light-emitting device material containing a pyrene compound represented by the following general formula (4):

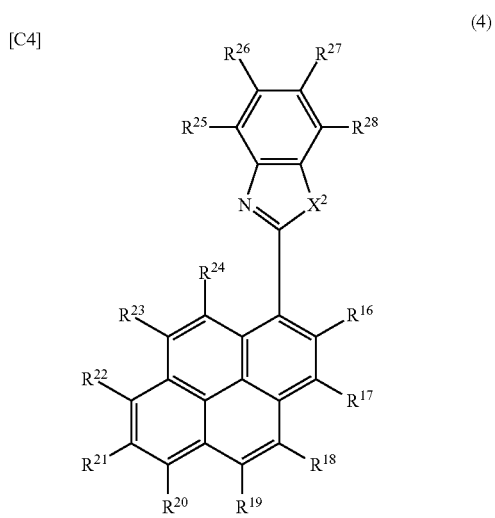

[C4]

(4)

wherein $R^{16}$ to $R^{24}$ each may be the same or different and are selected from among hydrogen, alkyl group, cycloalkyl group, heterocyclic group, alkenyl group, cycloalkenyl group, alkynyl group, alkoxy group, alkylthio group, arylether group, arylthioether group, aryl group, heteroaryl group, halogen, cyano group, carbonyl group, carboxyl group, oxycarbonyl group, carbamoyl group, amino group, phosphine oxide group and condensed ring formed between adjacent groups; $R^{25}$ to $R^{28}$ each may be the same or different and are selected from among hydrogen, alkyl group, cycloalkyl group, heterocyclic group, alkenyl group, cycloalkenyl group, alkynyl group, alkoxy group, alkylthio group, arylether group, arylthioether group, aryl group, heteroaryl group, halogen, cyano group, carbonyl group, carboxyl group, oxycarbonyl group, carbamoyl group, amino group and phosphine oxide group; and $X^2$ is selected from among groups represented by the following general formula (5):

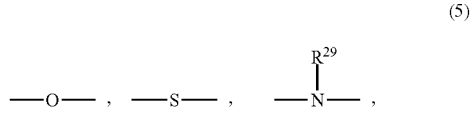

[C5]

(5)

wherein $R^{29}$ is selected from the group consisting of hydrogen, alkyl group, cycloalkyl group, heterocyclic group, alkenyl group, cycloalkenyl group, alkynyl group, aryl group, heteroaryl group, cyano group, carbonyl group, carboxyl group, oxycarbonyl group and carbamoyl group, wherein at least one of $R^{17}$, $R^{20}$ and $R^{22}$ is an aryl group or heteroaryl group.

3. A light-emitting device material containing a pyrene compound represented by the following general formula (4):

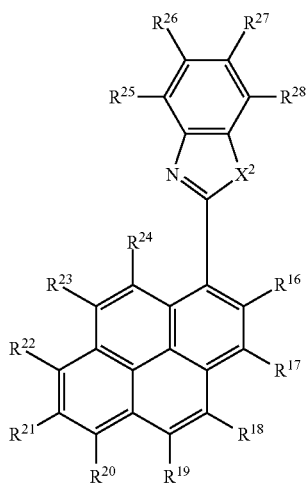

(4)

wherein $R^{16}$ to $R^{24}$ each may be the same or different and are selected from among hydrogen, alkyl group, cycloalkyl group, heterocyclic group, alkenyl group, cycloalkenyl group, alkynyl group, alkoxy group, alkylthio group, arylether group, arylthioether group, aryl group, heteroaryl group, halogen, cyano group, carbonyl group, carboxyl group, oxycarbonyl group, carbamoyl group, amino group, phosphine oxide group and condensed ring formed between adjacent groups; $R^{25}$ to $R^{28}$ each may be the same or different and are selected from among hydrogen, alkyl group, cycloalkyl group, heterocyclic group, alkenyl group, cycloalkenyl group, alkynyl group, alkoxy group, alkylthio group, arylether group, arylthioether group, aryl group, heteroaryl group, halogen, cyano group, carbonyl group, carboxyl group, oxycarbonyl) group, carbamoyl group, amino group and phosphine oxide group; and $X^2$ is selected from among groups represented by the following general formula (5):

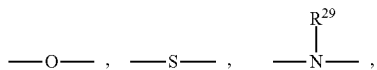

(5)

wherein $R^{29}$ is selected from the group consisting of hydrogen, alkyl group, cycloalkyl group, heterocyclic group, alkenyl group, cycloalkenyl group, alkynyl group, aryl group, heteroaryl group, cyano group, carbonyl group, carboxyl group, oxycarbonyl group and carbamoyl group, wherein $R^{17}$ and $R^{22}$ are an aryl group or heteroaryl group.

4. A light-emitting device comprising the light-emitting device material according to claim 1, wherein at least a luminous layer exists between an anode and a cathode to emit light by electric energy.

5. The light-emitting device according to claim 4, wherein the luminous layer comprises a host material and a dopant material, the dopant material comprising the light-emitting device material according to claim 1.

6. The light-emitting device according to claim 4, wherein at least an electron transporting layer exists between the luminous layer and the cathode, the electron transporting layer contains a compound having a heteroaryl ring structure having electron-accepting nitrogen, and the compound having a heteroaryl ring structure is composed of an element selected from the group consisting of carbon, hydrogen, nitrogen, oxygen, silicon and phosphorus.

7. A light-emitting device comprising the light-emitting device material according to claim 2, wherein at least a luminous layer exists between an anode and a cathode to emit light by electric energy.

8. The light-emitting device according to claim 7, wherein the luminous layer comprises a host material and a dopant material, the dopant material comprising the light-emitting device material according to claim 2.

9. The light-emitting device according to claim 7, wherein at least an electron transporting layer exists between the luminous layer and the cathode, the electron transporting layer contains a compound having a heteroaryl ring structure having electron-accepting nitrogen, and the compound having a heteroaryl ring structure is composed of an element selected from the group consisting of carbon, hydrogen, nitrogen, oxygen, silicon and phosphorus.

10. A light-emitting device comprising the light-emitting device material according to claim 3, wherein at least a luminous layer exists between an anode and a cathode to emit light by electric energy.

11. The light-emitting device according to claim 10, wherein the luminous layer comprises a host material and a dopant material, the dopant material comprising the light-emitting device material according to claim 3.

12. The light-emitting device according to claim 10, wherein at least an electron transporting layer exists between the luminous layer and the cathode, the electron transporting layer contains a compound having a heteroaryl ring structure having electron-accepting nitrogen, and the compound having a heteroaryl ring structure is composed of an element selected from the group consisting of carbon, hydrogen, nitrogen, oxygen, silicon and phosphorus.

* * * * *